US006261769B1

(12) United States Patent
Everett et al.

(10) Patent No.: US 6,261,769 B1
(45) Date of Patent: Jul. 17, 2001

(54) INTERGENIC SPACER TARGET SEQUENCE FOR DETECTING AND DISTINGUISHING CHLAMYDIAL SPECIES OR STRAINS

(75) Inventors: Karin D. E. Everett; Arthur A. Andersen, both of Ames, IA (US)

(73) Assignee: The United States of America as represented by the Secretary of Agriculture, Washington, DC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/052,333

(22) Filed: Mar. 31, 1998

(51) Int. Cl.[7] .............................. C12Q 1/68; C12P 19/34; C07H 21/04

(52) U.S. Cl. .......................... 435/6; 435/91.2; 536/24.32; 536/24.33

(58) Field of Search .................. 435/6, 91.2; 536/24.32, 536/24.33

(56) References Cited

U.S. PATENT DOCUMENTS

| | | | |
|---|---|---|---|
| 5,232,829 | 8/1993 | Longiaru | 435/6 |
| 5,512,445 | 4/1996 | Yang et al. | 435/6 |
| 5,514,551 | 5/1996 | Yang et al. | 435/6 |
| 5,693,468 | 12/1997 | Hogan et al. | 435/6 |
| 5,756,298 | 5/1998 | Burczak et al. | 435/6 |
| 5,814,490 | 9/1998 | Spears | 435/91.2 |

FOREIGN PATENT DOCUMENTS

| | | | |
|---|---|---|---|
| WO9015159 | | 12/1990 | (WO) . |
| WO9304163 | * | 3/1993 | (WO) . |
| WO9600298 | * | 1/1996 | (WO) . |
| WO9612040 | * | 4/1996 | (WO) . |

OTHER PUBLICATIONS

Wilson et al. Journal of Applied Bacteriology 80, 431–438, 1996.*

Amann et al. Applied and Environmental Microbiology, vol. 63(1), 115–121, Jan. 1997.*

Wilson et al. GenBank Accession No. Z49874, Jun. 1995.*

Goessens et al., "Comparison of Three Commercially Available Amplification Assays, AMP CT, Lcx, and COBAS AMPLICOR, for Detection of *Chlamydia trachomatis* in First–Void Urine", *Journal of Clinical Microbiology*, Oct. 97, vol. 35, No. 10, pp. 2628–2633.

Gürtler, Volker, et al., "New Approaches to typing and identification of bacteria using t he 16S–23S rDNA spacer region", *Microbiology*, 1996, 142, pp. 3–16.

Meijer, A., et al., "Species Identification of Chlamydia Isolates by Analyzing Restriction Fragment Length Polymorphism of the 16S–23S rRNA Spacer Region", *Journal of Clinical Microbiology*, May 1997, vol. 35, No. 5, pp. 1179–1183.

* cited by examiner

*Primary Examiner*—W. Gary Jones
*Assistant Examiner*—Juliet C. Einsmann
(74) *Attorney, Agent, or Firm*—M. Howard Silverstein; Curtis P. Ribando; John D. Fado

(57) ABSTRACT

The intergenic spacer between the 16S and the 23S rRNA genes and a 131-bp segment at the 3' end of Domain I of the 23S gene provides suitable target sequences for developing probes and primers useful in detecting and identifying Chlamydiaceae in laboratory and clinical samples.

12 Claims, 1 Drawing Sheet

SEQUENCE LISTING (1) GENERAL INFORMATION:

(iii) NUMBER OF SEQUENCES: 73

(2) INFORMATION FOR SEQ ID NO:1:

(i) SEQUENCE CHARACTERISTICS:
(A) LENGTH: 1283 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci
(B) STRAIN: CP3(VR 574)

(ix) FEATURE:
(A) NAME/KEY: rRNA
(B) LOCATION: 1..219
(D) OTHER INFORMATION: /note= "16S ribosomal RNA"

(ix) FEATURE:
(A) NAME/KEY: misc_RNA
(B) LOCATION: 220..442
(D) OTHER INFORMATION: /note= "intergenic spacer"

-continued (ix) FEATURE:
(A) NAME/KEY: rRNA
(B) LOCATION: 443..1063
(D) OTHER INFORMATION: /note= "Domain 1 of the 23S ribosomal RNA"

(ix) FEATURE:
(A) NAME/KEY: rRNA
(B) LOCATION: 443..1283
(D) OTHER INFORMATION: /note= "23S rRNA"

(ix) FEATURE:
(A) NAME/KEY: misc_RNA
(B) LOCATION: 1..535
(D) OTHER INFORMATION: /note= "Region A - Region of the Intergenic Spacer"

(ix) FEATURE:
(A) NAME/KEY: rRNA
(B) LOCATION: 957..1086
(D) OTHER INFORMATION: /note= "Region B - The 3' End of Domain I in the 23S rRNA"

(xi) SEQUENCE DESCRIPTION: SEQ ID NO:1:

```
CATGAAGTCG GAATTGCTAG TAATGGCGTG TCAGCTATAA CGCCGTGAAT ACGTTCCCGG     60

GCCTTGTACA CACCGCCCGT CACATCATGG GAGTTGGTTT TGCCTTAAGT CGTTGACTCA    120

ACCTGCAAAG GAGAGAGGCG CCCAAGGTGA GGCTGATGAC TGGGATGAAG TCGTAACAAG    180

GTAGCCCTAC CGGAAGGTGG GGCTGGATCA CCTCCTTTTA AGGATAAGGA TAACTGTCTT    240

AGGACGGTTT GACTAGGTTG GGCAAGCGTT TTTTAATCTT GTATTCTATT TCTTTTGCAT    300

TGTTAAGTGT TGTTTCCAAA ACATTTAGTT TACGATCAAT TATGTTATGT AAATAATATG    360

GTAACAAGTA AATTCACATA TAATAATAGA CGTTTAAGAA TATATGTCTT TAGGTGATGT    420

TAACTTGCAT GGATCAATAA TTTACAGACC AAGTTATTAA GAGCTATTGG TGGATGCCTT    480

GGCATTGACA GGCGATGAAG GATGCGTTTA CCTGCAGTAA TCTTCGGCGA GCTGGTATAA    540

AGCTATGACC CGGAGGTCTC CGAATGGGGC AACCCGGTAG ATTAATCATC TACCATTATA    600

CGTTGAATAC ATAGGCGTAT AAGGCGACAC CTGCTGAACT GAAACATCTT AGTAAGCAGA    660

GGAAAATAAA TCAAAGAGAT TCCCTAAGTA GCGGCGAGCG AAAAGGGAGA AGACCAAACC    720

ACATTTTTAA TGTGGGGTTG TAGGGTCGAT AACATGGGAT CTTAAGTTTT AGTTGAATAC    780

TTCTGGAAAG CAGAACGATA CAGGGTGATA GTCCCGTAGA CGAAAAAACA AGAGACTCTA    840

TTCGATACCT GAGTAGGGCT AGACACGTGA AACCTAGTCT GAATCTGGGG AGACCACTCT    900

CCAAGTCTAA ATACTAGTCA ATGACCTATA GTGAACCAGT ACTGTGAAGG AAAGGTGAAA    960

AGAACCCTTG TTAAGGGAGT GAAATAGAAC CTGAAACCAG TAGCTTATAA GCGGTCGAAG   1020

ACCTATAACT TCTTAGGAAG TCATGGTTGA CGGCGTGCCT TTTGCATGAT GAGCCAGGGA   1080

GTTAAGTTAA ACGGCGAGGT TAAGGGATTT ACATTCCGGA GCCGAAGCGA AAGCGAGTTT   1140

TAAAAGAGCG TTTAGTCGTT TGATTTAGAC ACGAAACCAA GTGAGCTATT TATGACCAGG   1200

TTGAAGCATG GGTAAGACCA TGTGGAGGAC CGAACCAGTA CATGTTGAAA AATGTTTGGA   1260

TGAGTTGTGA ATAGGGGTGA AAG                                           1283
```

(2) INFORMATION FOR SEQ ID NO:2:

(i) SEQUENCE CHARACTERISTICS:
(A) LENGTH: 1283 base pairs
(B) TYPE: nucleic acid
(C) STRANDEDNESS: single
(D) TOPOLOGY: linear (ii) MOLECULE TYPE: rRNA -continued (iii) HYPOTHETICAL: NO (iv) ANTI-SENSE: NO (vi) ORIGINAL SOURCE:
(A) ORGANISM: Chlamydia psittaci
(B) STRAIN: MN (VR 122)

(ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..442
(D) OTHER INFORMATION: /note= "intergenic spacer"

(ix) FEATURE:
(A) NAME/KEY: rRNA
(B) LOCATION: 443..1063
(D) OTHER INFORMATION: /note= "Domain I of the 23S rRNA"

(ix) FEATURE:
(A) NAME/KEY: rRNA
(B) LOCATION: 443..1283
(D) OTHER INFORMATION: /note= "23S rRNA"

(ix) FEATURE:
(A) NAME/KEY: misc_RNA
(B) LOCATION: 1..535
(D) OTHER INFORMATION: /note= "Region A - Region of the Intergenic Spacer"

(ix) FEATURE:
(A) NAME/KEY: rRNA
(B) LOCATION: 957..1086
(D) OTHER INFORMATION: /note= "Region B - The 3' End of Domain I in the 23S rRNA"

(xi) SEQUENCE DESCRIPTION: SEQ ID NO:2:

CATGAAGTCG GAATTGCTAG TAATGGCGTG TCAGCTATAA CGCCGTGAAT ACGTTCCCGG 60

GCCTTGTACA CACCGCCCGT CACATCATGG GAGTTGGTTT TGCCTTAAGT CGTTGACTCA 120

ACCTGCAAAG GAGAGAGGCG CCCAAGGTGA GGCTGATGAC TGGGATGAAG TCGTAACAAG 180

GTAGCCCTAC CGGAAGGTGG GGCTGGATCA CCTCCTTTTA AGGATAAGGA TAACTGTCTT 240

AGGACGGTTT GACTAGGTTG GGCAAGCGTT TTTTAATCTT GTATTCTATT TCTTTTGCAT 300

TGTTAAGTGT TGTTTCCAAA ACATTTAGTT TACGATCAAG TATGTTATGT AAATAATATG 360

GTAACAAGTA AATTCACATA TAATAATAGA CGTTTAAGAA TATATGTCTT TAGGTGATGT 420

TAACTTGCAT GGATCAATAA TTTACAGACC AAGTTATTAA GAGCTATTGG TGGATGCCTT 480

GGCATTGACA GGCGATGAAG GATGCGTTTA CCTGCAGTAA TCTTCGGCGA GCTGGTATAA 540

AGCTATGACC CGGAGGTCTC CGAATGGGGC AACCCGGTAG ATTAATCATC TACCATTATA 600

CGTTGAATAC ATAGGCGTAT AAGGCGACAC CTGCTGAACT GAAACATCTT AGTAAGCAGA 660

GGAAAATAAA TCAAAGAGAT TCCCTAAGTA GCGGCGAGCG AAAAGGGAGA AGACCAAACC 720

ACATTTTTAA TGTGGGGTTG TAGGGTCGAT AACATGGGAT CTTAAGTTTT AGTTGAATAC 780

TTCTGGAAAG CAGAACGATA CAGGGTGATA GTCCCGTAGA CGAAAAAACA AGAGACTCTA 840

TTCGATACCT GAGTAGGGCT AGACACGTGA AACCTAGTCT GAATCTGGGG AGACCACTCT 900

CCAAGTCTAA ATACTAGTCA ATGACCTATA GTGAACCAGT ACTGTGAAGG AAAGGTGAAA 960

AGAACCCTTG TTAAGGGAGT GAAATAGAAC CTGAAACCAG TAGCTTATAA GCGGTCGAAG 1020

ACCTATAACT TCTTAGGAAG TCATGGTTGA CGGCGTGCCT TTTGCATGAT GAGCCAGGGA 1080

-continued

```
GTTAAGTTAA ACGGCGAGGT TAAGGGATTT ACATTCCGGA GCCGAAGCGA AAGCGAGTTT   1140

TAAAAGAGCG TTTAGTCGTT TGATTTAGAC ACGAAACCAA GTGAGCTATT TATGACCAGG   1200

TTGAAGCATG GGTAAGACCA TGTGGAGGAC CGAACCAGTA CATGTTGAAA AATGTTTGGA   1260

TGAGTTGCGA ATAGGGGTGA AAG                                           1283
```

(2) INFORMATION FOR SEQ ID NO:3:

(i) SEQUENCE CHARACTERISTICS:
(A) LENGTH: 1283 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci
(B) STRAIN: MN Zhang (ix) FEATURE:
(A) NAME/KEY: rRNA
(B) LOCATION: 1..219
(D) OTHER INFORMATION: /note= “16S rRNA”

(ix) FEATURE:
(A) NAME/KEY: misc_RNA
(B) LOCATION: 220..442
(D) OTHER INFORMATION: /note= “intergenic spacer”

(ix) FEATURE:
(A) NAME/KEY: rRNA
(B) LOCATION: 443..1063
(D) OTHER INFORMATION: /note= “Domain I of the 23S rRNA”

(ix) FEATURE:
(A) NAME/KEY: rRNA
(B) LOCATION: 443..1283
(D) OTHER INFORMATION: /note= “23S rRNA”

(ix) FEATURE:
(A) NAME/KEY: misc_RNA
(B) LOCATION: 1..535
(D) OTHER INFORMATION: /note= “Domain A - Region of the Intergenic Spacer”

(ix) FEATURE:
(A) NAME/KEY: rRNA
(B) LOCATION: 957..1086
(D) OTHER INFORMATION: /note= “Region B - The 3' End of Domain I in the 23S rRNA”

(xi) SEQUENCE DESCRIPTION: SEQ ID NO:3:

```
CATGAAGTCG GAATTGCTAG TAATGGCGTG TCAGCTATAA CGCCGTGAAT ACGTTCCCGG     60

GCCTTGTACA CACCGCCCGT CACATCATGG GAGTTGGTTT TGCCTTAAGT CGTTGACTCA    120

ACCTGCAAAG GAGAGAGGCG CCCAAGGTGA GGCTGATGAC TGGGATGAAG TCGTAACAAG    180

GTAGCCCTAC CGGAAGGTGG GGCTGGATCA CCTCCTTTTA AGGATAAGGA TAACTGTCTT    240

AGGACGGTTT GACTAGGTTG GGCAAGCGTT TTTTAATCTT GTATTCTATT TCTTTTGCAT    300

TGTTAAGTGT TGTTTCCAAA ACATTTAGTT TACGATCAAG TATGTTATGT AAATAATATG    360

GTAACAAGTA AATTCACATA TAATAATAGA CGTTTAAGAA TATATGTCTT TAGGTGATGT    420

TAACTTGCAT GGATCAATAA TTTACAGACC AAGTTATTAA GAGCTATTGG TGGATGCCTT    480

GGCATTGACA GGCGATGAAG GATGCGTTTA CCTGCAGTAA TCTTCGGCGA GCTGGTATAA    540
```

-continued

```
AGCTATGACC CGGAGGTCTC CGAATGGGGC AACCCGGTAG ATTAATCATC TACCATTATA    600

CGTTGAATAC ATAGGCGTAT AAGGCGACAC CTGCTGAACT GAAACATCTT AGTAAGCAGA    660

GGAAAATAAA TCAAAGAGAT TCCCTAAGTA GCGGCGAGCG AAAAGGGAGA AGACCAAACC    720

ACATTTTTAA TGTGGGGTTG TAGGGTCGAT AACATGGGAT CTTAAGTTTT AGTTGAATAC    780

TTCTGGAAAG CAGAACGATA CAGGGTGATA GTCCCGTAGA CGAAAAAACA AGAGACTCTA    840

TTCGATACCT GAGTAGGGCT AGACACGTGA AACCTAGTCT GAATCTGGGG AGACCACTCT    900

CCAAGTCTAA ATACTAGTCA ATGACCTATA GTGAACCAGT ACTGTGAAGG AAAGGTGAAA    960

AGAACCCTTG TTAAGGGAGT GAAATAGAAC CTGAAACCAG TAGCTTATAA GCGGTCGAAG   1020

ACCTATAACT TCTTAGGAAG TCATGGTTGA CGGCGTGCCT TTTGCATGAT GAGCCAGGGA   1080

GTTAAGTTAA ACGGCGAGGT TAAGGGATTT ACATTCCGGA GCCGAAGCGA AAGCGAGTTT   1140

TAAAAGAGCG TTTAGTCGTT TGATTTAGAC ACGAAACCAA GTGAGCTATT TATGACCAGG   1200

TTGAAGCATG GGTAAGACCA TGTGGAGGAC CGAACCAGTA CATGTTGAAA AATGTTTGGA   1260

TGAGTTGTGA ATAGGGGTGA AAG                                           1283
```

(2) INFORMATION FOR SEQ ID NO:4:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci
(B) STRAIN: 6BC (VR 125)

(ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..443
(D) OTHER INFORMATION: /note= "intergenic spacer"

(ix) FEATURE:
(A) NAME/KEY: rRNA
(B) LOCATION: 444..1064
(D) OTHER INFORMATION: /note= "Domain I of the 23S rRNA"

(ix) FEATURE:
(A) NAME/KEY: rRNA
(B) LOCATION: 444..1284
(D) OTHER INFORMATION: /note= "23S rRNA"

(ix) FEATURE:
(A) NAME/KEY: misc_RNA
(B) LOCATION: 1..536
(D) OTHER INFORMATION: /note= "Region A - Region of the Intergenic Spacer"

(ix) FEATURE:
(A) NAME/KEY: rRNA
(B) LOCATION: 958..1087
(D) OTHER INFORMATION: /note= "Region B - The 3' End of Domain I in the 23S rRNA"

(xi) SEQUENCE DESCRIPTION: SEQ ID NO:4:

-continued

```
CATGAAGTCG GAATTGCTAG TAATGGCGTG TCAGCTATAA CGCCGTGAAT ACGTTCCCGG     60
GCCTTGTACA CACCGCCCGT CACATCATGG GAGTTGGTTT TGCCTTAAGT CGTTGACTCA    120
ACCTGCAAAG GAGAGAGGCG CCCAAGGTGA GGCTGATGAC TGGGATGAAG TCGTAACAAG    180
GTAGCCCTAC CGGAAGGTGG GGCTGGATCA CCTCCTTTTA AGGATAAGGA TAACTGTCTT    240
AGGACGGTTT GACTAGGTTG GGCAAGCGTT TTTTTAATCT TGTATTCTAT TTCTTTTGCA    300
TTGTTAAGCG TTGTTTCCAA AACATTTAGT TTACGATCAA GTATGTTATG TAAATAATAT    360
GGTAACAAGT AAATTCACAT ATAATAATAG ACGTTTAAGA ATATATGTCT TTAGGTGATG    420
TTAACTTGCA TGGATCAATA ATTTACAGAC CAAGTTATTA AGAGCTATTG GTGGATGCCT    480
TGGCATTGAC AGGCGATGAA GGATGCGTTT ACCTGCAGTA ATCTTCGGCG AGCTGGTATA    540
AAGCTATGAC CCGGAGGTCT CCGAATGGGG CAACCCGGTA GATTAATCAT CTACCATTAT    600
ACGTTGAATA CATAGGCGTA TAAGGCGACA CCTGCTGAAC TGAAACATCT TAGTAAGCAG    660
AGGAAAATAA ATCAAAGAGA TTCCCTAAGT AGCGGCGAGC GAAAGGGGAG AAGACCAAAC    720
CACATTTTTA ATGTGGGGTT GTAGGGTCGA TAACATGGGA TCTTAAGTTT TAGTTGAATA    780
CTTCTGGAAA GTAGAACGAT ACAGGGTGAT AGTCCCGTAG ACGAAAAAAC AAGAGACTCT    840
ATTCGATACC TGAGTAGGGC TAGACACGTG AAACCTAGTC TGAATCTGGG GAGACCACTC    900
TCCAAGTCTA AATACTAGTC AATGACCTAT AGTGAACCAG TACTGTGAAG GAAAGGTGAA    960
AAGAACCCTT GTTAAGGGAG TGAAATAGAA CCTGAAACCA GTAGCTTATA AGCGGTCGAA   1020
GACCTATAAC TTCTTAGGAA GTCATGGTTG ACGGCGTGCC TTTTGCATGA TGAGCCAGGG   1080
AGTTAAGTTA AACGGCGAGG TTAAGGGATT TACATTCCGG AGCCGAAGCG AAAGCGAGTT   1140
TTAAAAGAGC GTTTAGTCGT TTGATTTAGA CACGAAACCA AGTGAGCTAT TTATGACCAG   1200
GTTGAAGCAT GGGTAAGACC TTGTGGAGGA CCGAACCAGT ACATGTTGAA AAATGTTTGG   1260
ATGAGTTGTG AATAGGGGTG AAAG                                           1284
```

(2) INFORMATION FOR SEQ ID NO:5:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci
(B) STRAIN: M56

(ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..443
(D) OTHER INFORMATION: /note= "intergenic spacer"

(ix) FEATURE:
(A) NAME/KEY: rRNA
(B) LOCATION: 444..1064
(D) OTHER INFORMATION: /note= "Domain I of the 23S rRNA"

(ix) FEATURE:

-continued (A) NAME/KEY: rRNA
(B) LOCATION: 444..1284
(D) OTHER INFORMATION: /note= "23S rRNA"

(ix) FEATURE:
(A) NAME/KEY: misc_RNA
(B) LOCATION: 1..536
(D) OTHER INFORMATION: /note= "Region A - Region of the Intergenic Spacer"

(ix) FEATURE:
(A) NAME/KEY: rRNA
(B) LOCATION: 958..1087
(D) OTHER INFORMATION: /note= "Region B - The 3' End of Domain I in the 23S rRNA"

(xi) SEQUENCE DESCRIPTION: SEQ ID NO:5:

```
CATGAAGTCG GAATTGCTAG TAATGGCGTG TCAGCTATAA CGCCGTGAAT ACGTTCCCGG     60

GCCTTGTACA CACCGCCCGT CACATCATGG GAGTTGGTTT TGCCTTAAGT CGTTGACTCA    120

ACCTGTAAAG GAGAGAGGCG CCCAAGGTGA GGCTGATGAC TGGGATGAAG TCGTAACAAG    180

GTAGCCCTAC CGGAAGGTGG GGCTGGATCA CCTCCTTTTA AGGATAAGGA TAACTGTCTT    240

AGGACGGTTT GACTAGGTTG GGCAAGCGTT TTTTTAATCT TGTATTCTAT TTCTTTTGCA    300

TTGTTAAGCG TTGTTTCCAA AACATTTAGT TTACGATCAA GTATGTTATG TAAATAATAT    360

GGTAACAAGT AAATTCACAT ATAATAATAG ACGTTTAAGA ATATATGTCT TTAGGTGATG    420

TTAACTTGCA TGGATCAATA ATTTACAGAC CAAGTTATTA AGAGCTATTG GTGGATGCCT    480

TGGCATTGAC AGGCGATGAA GGATGCGTTT ACCTGCAGTA ATCTTCGGCG AGCTGGTATA    540

AAGCTGTGAC CCGGAGGTCT CCGAATGGGG CAACCCGGTA GATTAATCAT CTACCATTAT    600

ACGTTGAATA CATAGGCGTA TAAGGCGACA CCTGCTGAAC TGAAACATCT TAGTAAGCAG    660

AGGAAAATAA ATCAAAGAGA TTCCCTAAGT AGCGGCGAGC GAAAGGGGAG AAGACCAAAC    720

CACATTTTTA ATGTGGGGTT GTAGGGTCGA TAACATGGGA TCTTAAGTTT TAGTTGAATA    780

CTTCTGGAAA GTAGAACGAT ACAGGGTGAT AGTCCCGTAG ACGAAAAAAC AAGAGACTCT    840

ATTCGATACC TGAGTAGGGC TAGACACGTG AAACCTAGTC TGAATCTGGG GAGACCACTC    900

TCCAAGTCTA AATACTAGTC AATGACCTAT AGTGAACCAG TACTGTGAAG GAAAGGTGAA    960

AAGAACCCTT GTTAAGGGAG TGAAATAGAA CCTGAAACCA GTAGCTTATA AGCGGTCGAA   1020

GACCTATAAC TTCTTAGGAA GTCATGGTTG ACGGCGTGCC TTTTGCATGA TGAGCCAGGG   1080

AGTTAAGTTA AACGGCGAGG TTAAGGGATT TACATTCCGG AGCCGAAGCG AAAGTGAGTT   1140

TTAAAAGAGC GTTTAGTCGT TTGATTTAGA CACGAAACCA AGTGAGCTAT TTATGACCAG   1200

GTTGAAGCAT GGGTAAGACC TTGTGGAGGA CCGAACCAGT ACATGTTGAA AAATGTTTGG   1260

ATGAGTTGTG AATAGGGGTG AAAG                                          1284
```

(2) INFORMATION FOR SEQ ID NO:6:

(i) SEQUENCE CHARACTERISTICS:
(A) LENGTH: 2751 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci -continued (B) STRAIN: NJ1

(ix) FEATURE:
(A) NAME/KEY: rRNA
(B) LOCATION: 1..564
(D) OTHER INFORMATION: /note= "16S rRNA"

(ix) FEATURE:
(A) NAME/KEY: misc_RNA
(B) LOCATION: 565..788
(D) OTHER INFORMATION: /note= "intergenic spacer"

(ix) FEATURE:
(A) NAME/KEY: rRNA
(B) LOCATION: 789..1409
(D) OTHER INFORMATION: /note= "Domain I of the 23S rRNA"

(ix) FEATURE:
(A) NAME/KEY: rRNA
(B) LOCATION: 789..2751
(D) OTHER INFORMATION: /note= "23S rRNA"

(ix) FEATURE:
(A) NAME/KEY: misc_RNA
(B) LOCATION: 346..881
(D) OTHER INFORMATION: /note= "Region A - Region of the Intergenic Spacer"

(ix) FEATURE:
(A) NAME/KEY: rRNA
(B) LOCATION: 1303..1432
(D) OTHER INFORMATION: /note= "Region B - The 3' End of Domain I in the 23S rRNA"

(xi) SEQUENCE DESCRIPTION: SEQ ID NO:6:

```
TTACCTGGGC TTGACATGTA TTTGACCGCG ACAGAAATGT CGTTTTCCGC AAGGACGGAT     60

ACACAGGTGC TGCATGGCTG TCGTCAGCTC GTGCCGTGAG GTGTTGGGTT AAGTCCCGCA    120

ACGAGCGCAA CCCTTATCGT TAGTTGCCAA CACTTAGGGT GGGAACTCTA ACGAGACTGC    180

CTGGGTTAAC CAGGAGGAAG GCGAGGATGA CGTCAAGTCA GCATGGCCCT TATGCCCAGG    240

GCTACACACG TGCTACAATG GCCAGTACAG AAGGTAGCAA TATCGTGAGA TGGAGCAAAT    300

CCTCAAAGCT GGCCCCAGTT CGGATTGTAG TCTGCAACTC GACTACATGA AGTCGGAATT    360

GCTAGTAATG GCGTGTCAGC TATAACGCCG TGAATACGTT CCCGGGCCTT GTACACACCG    420

CCCGTCACAT CATGGGAGTT GGTTTTGCCT TAAGTCGTTG ACTCAACCTG TAAAGGAGAG    480

AGGCGCCCAA GGTGAGGCTG ATGACTGGGA TGAAGTCGTA ACAAGGTAGC CCTACCGGAA    540

GGTGGGGCTG GATCACCTCC TTTTAAGGAT AAGGATAACT GTCTTAGGAC GGTTTGACTA    600

GGTTGGGCAA GCGTTTTTTT AATCTTGTAT TCTATTTCTT TTGCATTGTT AAGCGTTGTT    660

TCCAAAACAT TTAGTTTACG ATCAAGTATG TTATGTAAAT AATATGGTAA CAAGTAAATT    720

CACATATAAT AATAGACGTT TAAGAATATA TGTCTTTAGG TGAAGTTAAC TTGCGTGGAT    780

CAATAATTTA CAGACCAAGT TATTAAGAGC TATTGGTGGA TGCCTTGGCA TTGACAGGCG    840

ATGAAGGATG CGTTTACCTG CAGTAATCTT CGGCGAGCTG GTATAAAGCT ATGACCCGGA    900

GGTCTCCGAA TGGGGCAACC CGGTAGATTA ATCATCTATC ATTATACGTT GAATACATAG    960

GCGTATAAGG CGACACCTGC TGAACTGAAA CATCTTAGTA AGCAGAGGAA AATAAATCAA   1020

AGAGATTCCC TAAGTAGCGG CGAGCGAAAG GGGAGAAGAC CAAACCGCAT TTTTAATGTG   1080

GGGTTGTAGG GTCGATAACA TGGGATCTTA AGTTTTAGTT GAATACTTCT GGAAAGTAGA   1140

ACGATACAGG GTGATAGTCC CGTAGACGAA AAAACAAGAG ACTCTATTCG ATACCTGAGT   1200

AGGGCTAGAC ACGTGAAACC TAGTCTGAAT CTGGGGAGAC CACTCTCCAA GTCTAAATAC   1260

TAGTCAATGA CCTATAGTGA ACCAGTACTG TGAAGGAAAG GTGAAAAGAA CCCTTGTTAA   1320
```

-continued

```
GGGAGTGAAA TAGAACCTGA AACCAGTAGC TTATAAGCGG TCGAAGACCT ATAACTTCTT   1380

AGGAAGTCAT GGTTGACGGC GTGCCTTTTG CATGATGAGC CAGGGAGTTA AGTTAAACGG   1440

CGAGGTTAAG GGATCTACAT TCCGGAGCCG AAGCGAAAGC GAGTTTTAAA AGAGCGTTTA   1500

GTCGTTTGAT TTAGACACGA AACCAAGTGA GCTATTTATG ACCAGGTTGA AGCATGGGTA   1560

AGACCTTGTG GAGGACCGAA CCAGTACATG TTGAAAAATG TTTGGATGAG TTGTGAATAG   1620

GGGTGAAAGG CCAATCAAAC TTGGAGATAT CTTGTTCTCT CCGAAATAAC TTTAGGGTTA   1680

GCCTCGGATA TTAAGCTTTT GGGGGTAGAG CACTGAATTC TAGCGGGGGC CTACCGGCTT   1740

ACCAAAGGAA ATCAAACTCC GAATACCAAA AGTGAGTCCG GGAGATAGAC AGCGGGGGCT   1800

AAGCTTCGTT GTCGAGAGGG GAACAGCCCA GACCGCCGAT TAAGGTCCCA AATTTTATGC   1860

TAAGTGAGTA AGGAAGTGAT GATTCTAAGA CAGTTGGAAT GTTGGCTTAG AGGCAGCAAT   1920

CATTTAAAGA GTGCGTAACA GCTCACCAAT CGAGAATCAT TGCGCCAATA ATAATCGGGG   1980

CTCAAGCATA AAACCGAAAT CGCGGGTGTA TATTTATATA TACGCGGTAG GAGAGCGTAG   2040

TATTCAGCAG TGAAGGTATA CCGTAAGGAG TGCTGGAGCG GATACTAGTG AAGATCCATG   2100

GCATAAGTAA CGATAAAGGA AGTGAAAATC TTCCTCGCCG TAAGCACAAG GTTTCCAGGG   2160

TCAAGCTCGT CTTCCCTGGG TTAGTCGGCC CCTAAGTCGA GGCACAAATG CGTAGACGAT   2220

GGAGCAACAG GTTAAATATT CCTGTACCAC CTAAAACTTT AGCAATGGAA TGACGGAGTA   2280

CGTTAAGCAC GCGGACGATT GGAAATGTCC GTATCACAAT GAGACCGGTT AGTAGGCAAA   2340

TCCGCTAACA TAAGGTTAGG TTGTGGTTAA GGGAAATCTT CGGAGGAACT GATAGTGTGG   2400

CGCAAGGCTT TCAAGAAATA ATTTCTAGCT GTTGATGGTG ACCGTACCTA AACCGACACA   2460

GGTGTGCGAG ATGAGTATTC TAAGGCGCGC GAGATAACTT TCGTTAAGGA ACTCGGCAAA   2520

TTATCCCCGT AACTTCGGAA GAAGGGGAGC CTCTTAGGGT GATTGCCTTT ACGGCATGAG   2580

CTCCGGGGGG CCGCAGAGAA ATGGCCCAGG CGACTGTTTA ACAAAAACAC AGCACTATGC   2640

AAACCTCTAA GGGGAAGTAT ATGGTGTGAC GCCTGCCCAA TGCCAAAAGG TTAAAGGGAT   2700

ATGTCAGCCG CAAGGCAAAG CATTGAACCC AAGCCCTGGT GAATGGCCGC C            2751
```

(2) INFORMATION FOR SEQ ID NO:7:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci
(B) STRAIN: CT1

(ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..443
(D) OTHER INFORMATION: /note= "intergenic spacer"

(ix) FEATURE:

-continued (A) NAME/KEY: rRNA
(B) LOCATION: 444..1064
(D) OTHER INFORMATION: /note= "Domain I of the 23S rRNA"

(ix) FEATURE:
(A) NAME/KEY: rRNA
(B) LOCATION: 444..1284
(D) OTHER INFORMATION: /note= "23S rRNA"

(ix) FEATURE:
(A) NAME/KEY: misc_RNA
(B) LOCATION: 1..536
(D) OTHER INFORMATION: /note= "Region A - Region of the Intergenic Spacer"

(ix) FEATURE:
(A) NAME/KEY: rRNA
(B) LOCATION: 958..1087
(D) OTHER INFORMATION: /note= "Region B - The 3' End of Domain I in the 23S rRNA"

(xi) SEQUENCE DESCRIPTION: SEQ ID NO:7:

```
CATGAAGTCG GAATTGCTAG TAATGGCGTG TCAGCTATAA CGCCGTGAAT ACGTTCCCGG     60

GCCTTGTACA CACCGCCCGT CACATCATGG GAGTTGGTTT TGCCTTAAGT CGTTGACTCA    120

ACCTGCAAAG GAGAGAGGCG CCCAAGGTGA GGCTGATGAC TGGGATGAAG TCGTAACAAG    180

GTAGCCCTAC CGGAAGGTGG GGCTGGATCA CCTCCTTTTA AGGATAAGGA TAACTGTCTT    240

AGGACGGTTT GACTAGGTTG GGCAAGCGTT TTTTTAATCT TGTATTCTAT TTCTTTTGCA    300

TTGTTAAGCG TTGTTTCCAA AACATTTAGT TTACGATCAA GTATGTTATG TAAATAATAT    360

GGTAACAAGT AAATTCACAT ATAATAATAG ACGTTTAAGA ATATATGTCT TTAGGTGAAG    420

TTAACTTGCA TGGATCAATA ATTTACAGAC CAAGTTATTA AGAGCTATTG GTGGATGCCT    480

TGGCATTGAC AGGCGATGAA GGATGCGTTT ACCTGCAGTA ATCTTCGGCG AGCTGGTATA    540

AAGCTATGAC CCGGAGGTCT CCGAATGGGG CAACCCGGTA GATTAATCAT CTACCATTAT    600

ACGTTGAATA CATAGACGTA TAAGGCGACA CCTGCTGAAC TGAAACATCT TAGTAAGCAG    660

AGGAAAATAA ATCAAAGAGA TTCCCTGAGT AGCGGCGAGC GAAAGGGGAG AAGACCAAAC    720

CACATTTTTA ATGTGGGGTT GTAGGGTCGA TAACATGGGA TCTTAAGTTT TAGTTGAATA    780

CTTCTGGAAA GTAGAACGAT ACAGGGTGAT AGTCCCGTAG ACGAAAAAAC AAGAGACTCT    840

ATTCGATACC TGAGTAGGGC TAGACACGTG AAACCTAGTC TGAATCTGGG GAGACCACTC    900

TCCAAGTCTA AATACTAGTC AATGACCTAT AGTGAACCAG TACTGTGAAG GAAAGGTGAA    960

AAGAACCCTT GTTAAGGGAG TGAAATAGAA CCTGAAACCA GTAGCTTATA AGCGGTCGAA   1020

GACCTATAAC TTCTTAGGAA GTCATGGTTG ACGGCGTGCC TTTTGCATGA TGAGCCAGGG   1080

AGTTAAGTTA AACGGCGAGG TTAAGGGATC TACATTCCGG AGCCGAAGCG AAAGCGAGTT   1140

TTAAAAGAGC GTTTAGTCGT TTGATTTAGA CACGAAACCA AGTGAGCTAT TTATGACCAG   1200

GTTGAAGCAT GGGTAAGACC TTGTGGAGGA CCGAACCAGT ACATGTTGAA AAATGTTTGG   1260

ATGAGTTGTG AATAGGGGTG AAAG                                          1284
```

(2) INFORMATION FOR SEQ ID NO:8:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO -continued (iv) ANTI-SENSE: NO (vi) ORIGINAL SOURCE:
(A) ORGANISM: Chlamydia psittaci
(B) STRAIN: GD (ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..443
(D) OTHER INFORMATION: /note= "intergenic spacer"

(ix) FEATURE:
(A) NAME/KEY: rRNA
(B) LOCATION: 444..1064
(D) OTHER INFORMATION: /note= "Domain I of the 23S rRNA"

(ix) FEATURE:
(A) NAME/KEY: rRNA
(B) LOCATION: 444..1284
(D) OTHER INFORMATION: /note= "23S rRNA"

(ix) FEATURE:
(A) NAME/KEY: misc_RNA
(B) LOCATION: 1..536
(D) OTHER INFORMATION: /note= "Region A - Region of the Intergenic Spacer"

(ix) FEATURE:
(A) NAME/KEY: rRNA
(B) LOCATION: 958..1087
(D) OTHER INFORMATION: /note= "Region B - The 3' End of Domain I in the 23S rRNA"

(xi) SEQUENCE DESCRIPTION: SEQ ID NO:8:

```
CATGAAGTCG GAATTGCTAG TAATGGCGTG TCAGCTATAA CGCCGTGAAT ACGTTCCCGG     60

GCCTTGTACA CACCGCCCGT CACATCATGG GAGTTGGTTT TGCCTTAAGT CGTTGACTCA    120

ACCTGCAAAG GAGAGAGGCG CCCAAGGTGA GGCTGATGAC TGGGATGAAG TCGTAACAAG    180

GTAGCCCTAC CGGAAGGTGG GGCTGGATCA CCTCCTTTTA AGGATAAGGA TAACTGTCTT    240

AGGACGGTTT GACTAGGTTG GGCAAGCGTT TTTTTAATCT TGTATTCTAT TTCTTTTGCA    300

TTGTTAAGCG TTGTTTCCAA AACATTTAGT TTACGATCAA GTATGTTATG TAAATAATAT    360

GGTAACAAGT AAATTCACAT ATAATAATAG ACGTTTAAGA ATATATGTCT TTAGGTGAAG    420

TTAACTTGCA TGGATCAATA ATTTACAGAC CAAGTTATTA AGAGCTATTG GTGGATGCCT    480

TGGCATTGAC AGGCGATGAA GGATGCGTTT ACCTGCAGTA ATCTTCGGCG AGCTGGTATA    540

AAGCTATGAC CCGGAGGTCT CCGAATGGGG CAACCCGGTA GATTAATCAT CTACCATTAT    600

ACGTTGAATA CATAGACGTA TAAGGCGACA CCTGCTGAAC TGAAACATCT TAGTAAGCAG    660

AGGAAAATAA ATCAAAGAGA TTCCCTGAGT AGCGGCGAGC GAAAGGGGAG AAGACCAAAC    720

CACATTTTTA ATGTGGGGTT GTAGGGTCGA TAACATGGGA TCTTAAGTTT TAGTTGAATA    780

CTTCTGGAAA GTAGAACGAT ACAGGGTGAT AGTCCCGTAG ACGAAAAAAC AAGAGACTCT    840

ATTCGATACC TGAGTAGGGC TAGACACGTG AAACCTAGTC TGAATCTGGG GAGACCACTC    900

TCCAAGTCTA AATACTAGTC AATGACCTAT AGTGAACCAG TACTGTGAAG GAAAGGTGAA    960

AAGAACCCTT GTTAAGGGAG TGAAATAGAA CCTGAAACCA GTAGCTTATA AGCGGTCGAA   1020

GACCTATAAC TTCTTAGGAA GTCATGGTTG ACGGCGTGCC TTTTGCATGA TGAGCCAGGG   1080

AGTTAAGTTA AACGGCGAGG TTAAGGGATC TACATTCCGG AGCCGAAGCG AAAGCGAGTT   1140
```

-continued

```
TTAAAAGAGC GTTTAGTCGT TTGATTTAGA CACGAAACCA AGTGAGCTAT TTATGACCAG   1200

GTTGAAGCAT GGGTAAGACC TTGTGGAGGA CCGAACCAGT ACATGTTGAA AAATGTTTGG   1260

ATGAGTTGTG AATAGGGGTG AAAG                                          1284
```

(2) INFORMATION FOR SEQ ID NO:9:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci
(B) STRAIN: Par1

(ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..443
(D) OTHER INFORMATION: /note= "intergenic spacer"

(ix) FEATURE:
(A) NAME/KEY: rRNA
(B) LOCATION: 444..1064
(D) OTHER INFORMATION: /note= "Domain I of the 23S rRNA"

(ix) FEATURE:
(A) NAME/KEY: rRNA
(B) LOCATION: 444..1284
(D) OTHER INFORMATION: /note= "23S rRNA"

(ix) FEATURE:
(A) NAME/KEY: misc_RNA
(B) LOCATION: 1..536
(D) OTHER INFORMATION: /note= "Region A - Region of the Intergenic Spacer"

(ix) FEATURE:
(A) NAME/KEY: rRNA
(B) LOCATION: 958..1087
(D) OTHER INFORMATION: /note= "Region B - The 3' End of Domain I in the 23S rRNA"

(xi) SEQUENCE DESCRIPTION: SEQ ID NO:9:

```
CATGAAGTCG GAATTGCTAG TAATGGCGTG TCAGCTATAA CGCCGTGAAT ACGTTCCCGG     60

GCCTTGTACA CACCGCCCGT CACATCATGG GAGTTGGTTT TGCCTTAAGT CGTTGACTCA    120

ACCTGCAAAG GAGAGAGGCG CCCAAGGTGA GGCTGATGAC TGGGATGAAG TCGTAACAAG    180

GTAGCCCTAC CGGAAGGTGG GGCTGGATCA CCTCCTTTTA AGGATAAGGA TAACTGTCTT    240

AGGACGGTTT GACTAGGTTG GGCAAGCGTT TTTTTAATCT TGTATTCTAT TTCTTTTGCA    300

TTGTTAAGCG TTGTTTCCAA AACATTTAGT TTACGATCAA GTATGTTATG TAAATAATAT    360

GGTAACAAGT AAATTCACAT ATAATAATAG ACGTTTAAGA ATATATGTCT TTAGGTGAAG    420

TTAACTTGCA TGGATCAATA ATTTACAGAC CAAGTTATTA AGAGCTATTG GTGGATGCCT    480

TGGCATTGAC AGGCGATGAA GGATGCGTTT ACCTGCAGTA ATCTTCGGCG AGCTGGTATA    540

AAGCTATGAC CCGGAGGTCT CCGAATGGGG CAACCCGGTA GATTAATCAT CTACCATTAT    600
```

-continued

```
ACGTTGAATA CATAGACGTA TAAGGCGACA CCTGCTGAAC TGAAACATCT TAGTAAGCAG    660

AGGAAAATAA ATCAAAGAGA TTCCCTGAGT AGCGGCGAGC GAAAGGGGAG AAGACCAAAC    720

CACATTTTTA ATGTGGGGTT GTAGGGTCGA TAACATGGGA TCTTAAGTTT TAGTTGAATA    780

CTTCTGGAAA GTAGAACGAT ACAGGGTGAT AGTCCCGTAG ACGAAAAAAC AAGAGACTCT    840

ATTCGATACC TGAGTAGGGC TAGACACGTG AAACCTAGTC TGAATCTGGG GAGACCACTC    900

TCCAAGTCTA AATACTAGTC AATGACCTAT AGTGAACCAG TACTGTGAAG GAAAGGTGAA    960

AAGAACCCTT GTTAAGGGAG TGAAATAGAA CCTGAAACCA GTAGCTTATA AGCGGTCGAA   1020

GACCTATAAC TTCTTAGGAA GTCATGGTTG ACGGCGTGCC TTTTGCATGA TGAGCCAGGG   1080

AGTTAAGTTA AACGGCGAGG TTAAGGGATC TACATTCCGG AGCCGAAGCG AAAGCGAGTT   1140

TTAAAAGAGC GTTTAGTCGT TTGATTTAGA CACGAAACCA AGTGAGCTAT TTATGACCAG   1200

GTTGAAGCAT GGGTAAGACC TTGTGGAGGA CCGAACCAGT ACATGTTGAA AAATGTTTGG   1260

ATGAGTTGTG AATAGGGGTG AAAG                                          1284
```

(2) INFORMATION FOR SEQ ID NO:10:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamytia psittaci
(B) STRAIN: WC (ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..443
(D) OTHER INFORMATION: /note= "intergenic spacer"

(ix) FEATURE:
(A) NAME/KEY: rRNA
(B) LOCATION: 444..1064
(D) OTHER INFORMATION: /note= "Domain I of the 23S rRNA"

(ix) FEATURE:
(A) NAME/KEY: rRNA
(B) LOCATION: 444..1284
(D) OTHER INFORMATION: /note= "23S rRNA"

(ix) FEATURE:
(A) NAME/KEY: misc_RNA
(B) LOCATION: 1..536
(D) OTHER INFORMATION: /note= "Region A - Region of the Intergenic Spacer"

(ix) FEATURE:
(A) NAME/KEY: rRNA
(B) LOCATION: 958..1087
(D) OTHER INFORMATION: /note= "Region B - The 3' End of Domain I in the 23S rRNA"

(xi) SEQUENCE DESCRIPTION: SEQ ID NO:10:

```
CATGAAGTCG GAATTGCTAG TAATGGCGTG TCAGCTATAA CGCCGTGAAT ACGTTCCCGG     60
```

-continued

```
GCCTTGTACA CACCGCCCGT CACATCATGG GAGTTGGTTT TGCCTTAAGT CGTTGACTCA    120

ACCTGCAAAG GAGAGAGGCG CCCAAGGTGA GGCTGATGAC TGGGATGAAG TCGTAACAAG    180

GTAGCCCTAC CGGAAGGTGG GGCTGGATCA CCTCCTTTTA AGGATAAGGA TAACTGTCTT    240

AGGACGGTTT GACTAGGTTG GGCAAGCGTT TTTTTAATCT TGTATTCTAT TTCTTTTGCA    300

TTGTTAAGCG TTGTTTCCAA AACATTTAGT TTACGATCAA GTATGTTATG TAAATAATAT    360

GGTAACAAGT AAATTCACAT ATAATAATAG ACGTTTAAGA ATATATGTCT TTAGGTGAAG    420

TTAACTTGCA TGGATCAATA ATTTACAGAC CAAGTTATTA AGAGCTATTG GTGGATGCCT    480

TGGCATTGAC AGGCGATGAA GGATGCGTTT ACCTGCAGTA ATCTTCGGCG AGCTGGTATA    540

AAGCTATGAC CCGGAGGTCT CCGAATGGGG CAACCCGGTA GATTAATCAT CTACCATTAT    600

ACGTTGAATA CATAGACGTA TAAGGCGACA CCTGCTGAAC TGAAACATCT TAGTAAGCAG    660

AGGAAAATAA ATCAAAGAGA TTCCCTGAGT AGCGGCGAGC GAAAGGGGAG AAGACCAAAC    720

CACATTTTTA ATGTGGGGTT GTAGGGTCGA TAACATGGGA TCTTAAGTTT TAGTTGAATA    780

CTTCTGGAAA GTAGAACGAT ACAGGGTGAT AGTCCCGTAG ACGAAAAAAC AAGAGACTCT    840

ATTCGATACC TGAGTAGGGC TAGACACGTG AAACCTAGTC TGAATCTGGG GAGACCACTC    900

TCCAAGTCTA AATACTAGTC AATGACCTAT AGTGAACCAG TACTGTGAGG GAAAGGTGAA    960

AAGAACCCTT GTTAAGGGAG TGAAATAGAA CCTGAAACCA GTAGCTTATA AGCGGTCGAA   1020

GACCTATAAC TTCTTAGGAA GTCATGGTTG ACGGCGTGCC TTTTGCATGA TGAGCCAGGG   1080

AGTTAAGTTA AACGGCGAGG TTAAGGGATC TACATTCCGG AGCCGAAGCG AAAGCGAGTT   1140

TTAAAAGAGC GTTTAGTCGT TTGATTTAGA CACGAAACCA AGTGAGCTAT TTATGACCAG   1200

GTTGAAGCAT GGGTAAGACC TTGTGGAGGA CCGAACCAGT ACATGTTGAA AAATGTTTGG   1260

ATGAGTTGTG AATAGGGGTG AAAG                                          1284
```

(2) INFORMATION FOR SEQ ID NO:11:

(i) SEQUENCE CHARACTERISTICS:
(A) LENGTH: 1282 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci
(B) STRAIN: EBA (ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..441
(D) OTHER INFORMATION: /note= "intergenic spacer"

(ix) FEATURE:
(A) NAME/KEY: rRNA
(B) LOCATION: 442..1062
(D) OTHER INFORMATION: /note= "Domain I of the 23S rRNA"

(ix) FEATURE:
(A) NAME/KEY: rRNA
(B) LOCATION: 442..1282

-continued (D) OTHER INFORMATION: /note= "23S rRNA"

(ix) FEATURE:
(A) NAME/KEY: misc_RNA
(B) LOCATION: 1..534
(D) OTHER INFORMATION: /note= "Region A - Region of the Intergenic Spacer"

(ix) FEATURE:
(A) NAME/KEY: rRNA
(B) LOCATION: 956..1085
(D) OTHER INFORMATION: /note= "Region B - The 3' End of Domain I in the 23S rRNA"

(xi) SEQUENCE DESCRIPTION: SEQ ID NO:11:

```
CATGAAGTCG GAATTGCTAG TAATGGCGTG TCAGCTATAA CGCCGTGAAT ACGTTCCCGG     60

GCCTTGTACA CACCGCCCGT CACATCATGG GAGTTGGTTT TGCCTTAAGT CGTTGACTCA    120

ACCTGCAAAG GAGAGAGGCG CCCAAGGTGA GGCTGATGAC TGGGATGAAG TCGTAACAAG    180

GTAGCCCTAC CGGAAGGTGG GGCTGGATCA CCTCCTTTTA AGGATAAGGA TAACTGTCTT    240

AGGACGGTTT GACTAGGTTG GGCAAGCATT TTTTAATCTT GTATTCTATT TCTTTTGCAT    300

TGTTAAGCGT TGTTTCCAAA ACATTTAGTT TACGATCAAG TATGTTATGT AAATAATATG    360

GTAACAAGTA AATTCACATA TAATAATAGA CGTTTAAGAA TATCTGTCTT TGGTGAAGTT    420

AATTTGCATG GATCAATAAT TTACAGACCA AGTTATTAAG AGTTATTGGT GGATGCCTTG    480

GCATTGACAG GCGATGAAGG ATGCGTTTAC CTGCAGTAAT CTTCGGCGAG CTGGTATAAA    540

GCTATGACCC GGAGGTCTCC GAATGGGGCA ACCCGATAGA TTAATCATCT ATCATTGTAC    600

GCTGAATACA TAGGCGTATA AGGCGATACC TGCTGAACTG AAACATCTTA GTAAGCAGAG    660

GAAAATAAAT CAAAGAGATT CCCTGAGTAG CGGCGAGCGA AAGGGGAGAA GACCAAACCA    720

CATTTTTAAT GTGGGGTTGT AGGGTCGATA ACATGGGATC TTAAGTTTTA GTCGAATACT    780

TCTGGAAAGT AGAACGATAC AGGGTGATAG TCCCGTAGAC GAAAAAACAA GAGACTCTAT    840

TCGATACCTG AGTAGGGCTA GACACGTGAA ACCTAGTCTG AATCTGGGGA GACCACTCTC    900

CAAGTCTAAA TACTAGTCAA TGACCTATAG TGAACCAGTA CTGTGAAGGA AAGGTGAAAA    960

GAACCCTTGT TAAGGGAGTG AAATAGAACC TGAAACCAGT AGCTTATAAG CGGTCGAAGA   1020

CCTATAACTT CTTCGGAAGT CATGGTTGAC GGCGTGCCTT TTGCATGATG AGCCAGGGAG   1080

TTAAGTTAAA CGGCGAGGTT AAGGGATCTA CATTCCGGAG CCGAAGCGAA AGCGAGTTTT   1140

AAAAGAGCGT TTAGTCGTTT GATTTAGACA CGAAACCAAG TGAGCTATTT ATGACCAGGT   1200

TGAAGCATGG GTAAGACCTT GTGGAGGACC GAACCAGTAC ATGTTGAAAA ATGTTTGGAT   1260

GAGTTGTGAA TAGGGGTGAA AG                                            1282
```

(2) INFORMATION FOR SEQ ID NO:12:

(i) SEQUENCE CHARACTERISTICS:
(A) LENGTH: 1282 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci
(B) STRAIN: A22

-continued (ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..441
(D) OTHER INFORMATION: /note= "intergenic spacer"

(ix) FEATURE:
(A) NAME/KEY: rRNA
(B) LOCATION: 442..1062
(D) OTHER INFORMATION: /note= "Domain I of the 23S rRNA"

(ix) FEATURE:
(A) NAME/KEY: rRNA
(B) LOCATION: 442..1282
(D) OTHER INFORMATION: /note= "23S rRNA"

(ix) FEATURE:
(A) NAME/KEY: misc_RNA
(B) LOCATION: 1..534
(D) OTHER INFORMATION: /note= "Region A - Region of the Intergenic Spacer"

(ix) FEATURE:
(A) NAME/KEY: rRNA
(B) LOCATION: 956..1085
(D) OTHER INFORMATION: /note= "Region B - The 3' End of Domain I in the 23S rRNA"

(xi) SEQUENCE DESCRIPTION: SEQ ID NO:12:

```
CATGAAGTCG GAATTGCTAG TAATGGCGTG TCAGCTATAA CGCCGTGAAT ACGTTCCCGG     60

GCCTTGTACA CACCGCCCGT CACATCATGG GAGTTGGTTT TGCCTTAAGT CGTTGACTCA    120

ACCTGCAAAG GAGAGAGGCG CCCAAGGTGA GGCTGATGAC TGGGATGAAG TCGTAACAAG    180

GTAGCCCTAC CGGAAGGTGG GGCTGGATCA CCTCCTTTTA AGGATAAGGA TAACTGTCTT    240

AGGACGGTTT GACTAGGTTG GGCAAGCATT TTTTAATCTT GTATTCTATT TCTTTTGCAT    300

TGTTAAGCGT TGTTTCCAAA ACATTTAGTT TACGATCAAG TATGTTATGT AAATAATATG    360

GTAACAAGTA AATTCACATA TAATAATAGA CGTTTAAGAA TATCTGTCTT TGGTGAAGTT    420

AATTTGCATG GATCAATAAT TTACAGACCA AGTTATTAAG AGTTATTGGT GGATGCCTTG    480

GCATTGACAG GCGATGAAGG ATGCGTTTAC CTGCAGTAAT CTTCGGCGAG CTGGTATAAA    540

GCTATGACCC GGAGGTCTCC GAATGGGGCA ACCCGATAGA TTAATCATCT ATCATTGTAC    600

GCTGAATACA TAGGCGTATA AGGCGATACC TGCTGAACTG AAACATCTTA GTAAGCAGAG    660

GAAAATAAAT CAAAGAGATT CCCTGAGTAG CGGCGAGCGA AAGGGGAGAA GACCAAACCA    720

CATTTTTAAT GTGGGGTTGT AGGGTCGATA ACATGGGATC TTAAGTTTTA GTCGAATACT    780

TCTGGAAAGT AGAACGATAC AGGGTGATAG TCCCGTAGAC GAAAAAACAA GAGACTCTAT    840

TCGATACCTG AGTAGGGCTA GACACGTGAA ACCTAGTCTG AATCTGGGGA GACCACTCTC    900

CAAGTCTAAA TACTAGTCAA TGACCTATAG TGAACCAGTA CTGTGAAGGA AAGGTGAAAA    960

GAACCCTTGT TAAGGGAGTG AAATAGAACC TGAAACCAGT AGCTTATAAG CGGTCGAAGA   1020

CCTATAACTT CTTCGGAAGT CATGGTTGAC GGCGTGCCTT TTGCATGATG AGCCAGGGAG   1080

TTAAGTTAAA CGGCGAGGTT AAGGGATCTA CATTCCGGAG CCGAAGCGAA AGCGAGTTTT   1140

AAAAGAGCGT TTAGTCGTTT GATTTAGACA CGAAACCAAG TGAGCTATTT ATGACCAGGT   1200

TGAAGCATGG GTTAGACCTT GTGGAGGACC GAACCAGTAC ATGTTGAAAA ATGTTTGGAT   1260

GAGTTGTGAA TAGGGGTGAA AG                                             1282
```

-continued (2) INFORMATION FOR SEQ ID NO:13:

(i) SEQUENCE CHARACTERISTICS:
(A) LENGTH: 1282 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci
(B) STRAIN: B577 (VR 656)

(ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..441
(D) OTHER INFORMATION: /note= "intergenic spacer"

(ix) FEATURE:
(A) NAME/KEY: rRNA
(B) LOCATION: 442..1062
(D) OTHER INFORMATION: /note= "Domain I of the 23S rRNA"

(ix) FEATURE:
(A) NAME/KEY: rRNA
(B) LOCATION: 442..1282
(D) OTHER INFORMATION: /note= "23S rRNA"

(ix) FEATURE:
(A) NAME/KEY: misc_RNA
(B) LOCATION: 1..534
(D) OTHER INFORMATION: /note= "Region A - Region of the Intergenic Spacer"

(ix) FEATURE:
(A) NAME/KEY: rRNA
(B) LOCATION: 956..1085
(D) OTHER INFORMATION: /note= "Region B - The 3' End of Domain I in the 23S rRNA"

(xi) SEQUENCE DESCRIPTION: SEQ ID NO:13:

CATGAAGTCG GAATTGCTAG TAATGGCGTG TCAGCTATAA CGCCGTGAAT ACGTTCCCGG 60

GCCTTGTACA CACCGCCCGT CACATCATGG GAGTTGGTTT TGCCTTAAGT CGTTGACTCA 120

ACCTGCAAAG GAGAGAGGCG CCCAAGGTGA GGCTGATGAC TGGGATGAAG TCGTAACAAG 180

GTAGCCCTAC CGGAAGGTGG GACTGGATCA CCTCCTTTTA AGGATAAGGA TAACTGTCTT 240

AGGACGGTTT GACTAGGTTG GGCAAGCATT TTTTAATCTT GTATTCTATT TCTTTTGCAT 300

TGTTAAGCGT TGTTTCCAAA ACATTTAGTT TACGATCAAG TATGTTATGT AAATAATATG 360

GTAACAAGTA AATTCACATA TAATAATAGA CGTTTAAGAA TATCTGTCTT TGGTGAAGTT 420

AATTTGCATG GATCAATAAT TTACAGACCA AGTTATTAAG AGTTATTGGT GGATGCCTTG 480

GCATTGACAG GCGATGAAGG ATGCGTTTAC CTGCAGTAAT CTTCGGCGAG CTGGTATAAA 540

GCTATGACCC GGAGGTCTCC GAATGGGGCA ACCCGATAGA TTAATCATCT ATCATTGTAC 600

GCTGAATACA TAGGCGTATA AGGCGATACC TGCTGAACTG AAACATCTTA GTAAGCAGAG 660

GAAAATAAAT CAAAGAGATT CCCTGAGTAG CGGCGAGCGA AAGGGGAGAA GACCAAACCA 720

CATTTTTAAT GTGGGGTTGT AGGGTCGATA ACATGGGATC TTAAGTTTTA GTCGAATACT 780

TCTGGAAAGT AGAACGATAC AGGGTGATAG TCCCGTAGAC GAAAAAACAA GAGACTCTAT 840

-continued

```
TCGATACCTG AGTAGGGCTA GACACGTGAA ACCTAGTCTG AATCTGGGGA GACCACTCTC    900

CAAGTCTAAA TACTAGTCAA TGACCTATAG TGAACCAGTA CTGTGAAGGA AAGGTGAAAA    960

GAACCCTTGT TAAGGGAGTG AAATAGAACC TGAAACCAGT AGCTTATAAG CGGTCGAGGA   1020

CCTATAACTT CTTCGGAAGT CATGGTTGAC GGCGTGCCTT TTGCATGATG AGCCAGGGAG   1080

TTAAGTTAAA CGGCGAGGTT AAGGGATCTA CATTCCGGAG CCGAAGCGAA AGCGAGTTTT   1140

AAAAGAGCGT TTAGTCGTTT GATTTAGACA CGAAACCAAG TGAGCTATTT ATGACCAGGT   1200

TGAAGCATGG GTAAGACCTT GTGGAGGACC GAACCAGTAC ATGTTGAAAA ATGTCTGGAT   1260

GAGTTGTGAA TAGGGGCGAA AG                                              1282
```

(2) INFORMATION FOR SEQ ID NO:14:

(i) SEQUENCE CHARACTERISTICS:
(A) LENGTH: 1282 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci
(B) STRAIN: OSP (ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..441
(D) OTHER INFORMATION: /note= "intergenic spacer"

(ix) FEATURE:
(A) NAME/KEY: rRNA
(B) LOCATION: 442..1062
(D) OTHER INFORMATION: /note= "Domain I of the 23S rRNA"

(ix) FEATURE:
(A) NAME/KEY: rRNA
(B) LOCATION: 442..1282
(D) OTHER INFORMATION: /note= "23S rRNA"

(ix) FEATURE:
(A) NAME/KEY: misc_RNA
(B) LOCATION: 1..534
(D) OTHER INFORMATION: /note= "Region A - Region of the Intergenic Spacer"

(ix) FEATURE:
(A) NAME/KEY: rRNA
(B) LOCATION: 956..1085
(D) OTHER INFORMATION: /note= "Region B - The 3' End of Domain I in the 23S rRNA"

(xi) SEQUENCE DESCRIPTION: SEQ ID NO:14:

```
CATGAAGTCG GAATTGCTAG TAATGGCGTG TCAGCTATAA CGCCGTGAAT ACGTTCCCGG     60

GCCTTGTACA CACCGCCCGT CACATCATGG GAGTTGGTTT TGCCTTAAGT CGATGATTCA    120

ACCTGCAAAG GAGAGAGGCG CCCAAGGTGA GGCTGATGAC TGGGATGAAG TCGTAACAAG    180

GTAGCCCTAC CGGAAGGTGG GGCTGGATCA CCTCCTTTTA AGGATAAGGA TAACTGTCTT    240

AGGACGGTTT GACTAGGTTG GGCAAGCATT TTTTAATCTT GTATTCTATT TCTTTTGCAT    300
```

-continued

```
TGTTAAGCGT TGTTTCCAAA ACATTTAGTT TACGATCAAG TATGTTATGT AAATAATATG    360

GTAACAAGTA AATTCACATA TAATAATAGA CGTTTAAGAA TATCTGTCTT TGGTGAAGTT    420

AATTTGCATG GATCAATAAT TTACAGACCA AGTTATTAAG AGTTATTGGT GGATGCCTTG    480

GCATTGACAG GCGATGAAGG ATGCGTTTAC CTGCAGTAAT CTTCGGCGAG CTGGTATAAA    540

GCTATGACCC GGAGGTCTCC GAATGGGGCA ACCCGATAGA TTAATCATCT ATCATTGTAC    600

GCTGAATACA TAGGCGTATA AGGCGATACC TGCTGAACTG AAACATCTTA GTAAGCAGAG    660

GAAAATAAAT CAAAGAGATT CCCTGAGTAG CGGCGAGCGA AAGGGGAGAA GACCAAACCA    720

CATTTTTAAT GTGGGGTTGT AGGGTCGATA ACATGGGATC TTAAGTTTTA GTCGAATACT    780

TCTGGAAAGT AGAACGATAC AGGGTGATAG TCCCGTAGAC GAAAAAACAA GAGACTCTAT    840

TCGATACCTG AGTAGGGCTA GACACGTGAA ACCTAGTCTG AATCTGGGGA GACCACTCTC    900

CAAGTCTAAA TACTAGTCAA TGACCTATAG TGAACCAGTA CTGTGAAGGA AAGGTGAAAA    960

GAACCCTTGT TAAGGGAGTG AAATAGAACC TGAAACCAGT AGCTTATAAG CGGTCGAAGA   1020

CCTATAACTT CTTCGGAAGT CATGGTTGAC GGCGTGCCTT TTGCATGATG AGCCAGGGAG   1080

TTAAGTTAAA CGGCGAGGTT AAGGGATCTA CATTCCGGAG CCGAAGCGAA AGCGAGTTTT   1140

AAAAGAGCGT TTAGTCGTTT GATTTAGACA CGAAACCAAG TGAGCTATTT ATGACCAGGT   1200

TGAAGCATGG GTAAGACCTT GTGGAGGACC GAACCAGTAC ATGTTGAAAA ATGTTTGGAT   1260

GAGTTGTGAA TAGGGGTGAA AG                                            1282
```

(2) INFORMATION FOR SEQ ID NO:15:

(i) SEQUENCE CHARACTERISTICS:
(A) LENGTH: 1285 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci
(B) STRAIN: FP (VR 120)

(ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..443
(D) OTHER INFORMATION: /note= "intergenic spacer"

(ix) FEATURE:
(A) NAME/KEY: rRNA
(B) LOCATION: 444..1065
(D) OTHER INFORMATION: /note= "Domain I of the 23S rRNA"

(ix) FEATURE:
(A) NAME/KEY: rRNA
(B) LOCATION: 444..1285
(D) OTHER INFORMATION: /note= "23S rRNA"

(ix) FEATURE:
(A) NAME/KEY: misc_RNA
(B) LOCATION: 1..536
(D) OTHER INFORMATION: /note= "Region A - Region of the Intergenic Spacer"

-continued (ix) FEATURE:
(A) NAME/KEY: rRNA
(B) LOCATION: 958..1088
(D) OTHER INFORMATION: /note= "Region B - The 3' End of Domain I in the 23S rRNA"

(xi) SEQUENCE DESCRIPTION: SEQ ID NO:15:

```
CATGAAGTCG GAATTGCTAG TAATGGCGTG TCAGCTATAA CGCCGTGAAT ACGTTCCCGG     60
GCCTTGTACA CACCGCCCGT CACATCATGG GAGTTGGTTT TGCCTTAAGT CGTTGACTCA    120
ACCTGCAAAG GAGAGAGGCG CCCAAGGTGA GGCTGATGAC TGGGATGAAG TCGTAACAAG    180
GTAGCCCTAC CGGAAGGTGG GGCTGGATCA CCTCCTTTTA AGGATAAGGA TAACCGTTTT    240
AGGACGGTTT GACTAGGTTG GGCAAGCATT TTTGAAAACT TGTATTCTAT TTCTTTTGCG    300
TTGTTAAGCG TGGGTTACAA AACATTCAGT TTACGATCAA GTATGTTATG TAAATAATAT    360
GGTAACAAGT AAATTCACAT ATAATAATAG ACGTTTAAGA ATATATGTCT TTAGGTGAAG    420
TTAACTTGCA TGGATCAATA ATTTACAGAC CAAGTTAGTA AGAGCTATTG GCGGATGCCT    480
TGGCATTGAC AGGCGATGAA GGATGCGTTT ACCTGCAGTA ATCTTCGGCG AGCTGGTATA    540
AAGCTATGAC CCGGAGGTCT CCGAATGGGG CAACCCGGTA GATTAATCAT CTACCATTAT    600
ATGCTGAATA CATAGGCATA TAAAGCGACA CCTGCTGAAC TGAAACATCT TAGTAAGCAG    660
AGGAAAAGAA ATCAAAGAGA TTCCCTGAGT AGCGGCGAGC GAAAGGGGAT TAGACCAAAC    720
CACGTTTTTA ATGTGGGGTT GTAGGGTCGA TAACATGGGA TCTTAAGTTT TAGTTGAATA    780
CTTCTGGAAA GTAGAACGAC ACAGGGTGAT AGTCCCGTAA ACGAAAAAAC AAGAGACTCT    840
ATTCGATACC TGAGTAGGGC TAGACACGTG AAACCTAGTC TGAATCTGGG GAGACCACTC    900
TCCAAGTCTA AATACTAGTC AATGACCTAT AGTGAACCAG TACTGTGAAG GAAAGGTGAA    960
AAGAACCCTT GTTAAGGGAG TGAAATAGAA CCTGAAACCA ATAGCTTATA AGCGGTCGAA   1020
GACCTATTAG CTTTTTCGAA AGCAATGGTT GACGGCGTGC CTTTTGCATG ATGAGCCAGG   1080
GAGTTAAGTT AAACGGCGAG GTTAAGGGAT TTACATTCCG GAGCCGAAGC GAAAGCGAGT   1140
TTTAATAGAG CGTTTAGTCG TTTAATTTAG ACACGAAACC AAGTGAGCTA TTTATGACCA   1200
GGTTGAAGCG TGGGTAAGAC CTTGTGGAGG ACCGAACCAG TACATGTTGA AAAATGTTTG   1260
GATGAGTTGT GAATAGGGGT GAAAG                                          1285
```

(2) INFORMATION FOR SEQ ID NO:16:

(i) SEQUENCE CHARACTERISTICS:
(A) LENGTH: 1285 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psitacci
(B) STRAIN: FP Cello (ix) FEATURE:
(A) NAME/KEY: rRNA
(B) LOCATION: 1..221
(D) OTHER INFORMATION: /note= "16S rRNA"

(ix) FEATURE:
(A) NAME/KEY: misc_RNA

-continued (B) LOCATION: 222..443
(D) OTHER INFORMATION: /note= "intergenic spacer"

(ix) FEATURE:
(A) NAME/KEY: rRNA
(B) LOCATION: 444..1065
(D) OTHER INFORMATION: /note= "Domain I of the 23S rRNA"

(ix) FEATURE:
(A) NAME/KEY: rRNA
(B) LOCATION: 444..1285
(D) OTHER INFORMATION: /note= "23S rRNA"

(ix) FEATURE:
(A) NAME/KEY: misc_RNA
(B) LOCATION: 1..536
(D) OTHER INFORMATION: /note= "Region A - Region of the Intergenic Spacer"

(ix) FEATURE:
(A) NAME/KEY: rRNA
(B) LOCATION: 958..1088
(D) OTHER INFORMATION: /note= "Region B - The 3' End of Domain I in the 23S rRNA"

(xi) SEQUENCE DESCRIPTION: SEQ ID NO:16:

```
CATGAAGTCG GAATTGCTAG TAATGGCGTG TCAGCTATAA CGCCGTGAAT ACGTTCCCGG     60

GCCTTGTACA CACCGCCCGT CACATCATGG GAGTTGGTTT TGCCTTAAGT CGTTGACTCA    120

ACCTGCAAAG GAGAGAGGCG CCCAAGGTGA GGCTGATGAC CGGGATGAAG TCGTAACAAG    180

GTAGCCCTAC CGGAAGGTGG GGCTGGATCA CCTCCTTTTA AGGATAAGGA TAACCGTTTT    240

AGGACGGTTT GACTAGGTTG GGCAAGCATT TTTGAAAACT TGTATTCTAT TTCTTTTGCG    300

TTGTTAAGCG TGGGTTACAA AACATTCAGT TTACGATCAA GTATGTTATG TAAATAATAT    360

GGTAACAAGT AAATTCACAT ATAATAATAG ACGTTTAAGA ATATATGTCT TTAGGTGAAG    420

TTAACTTGCA TGGATCAATA ATTTACAGAC CAAGTTAGTA AGAGCTATTG GCGGATGCCT    480

TGGCATTGAC AGGCGATGAA GGATGCGTTT ACCTGCAGTA ATCTTCGGCG AGCTGGTATA    540

AAGCTATGAC CCGGAGGTCT CCGAATGGGG CAACCCGGTA GATTAATCAT CTACCATTAT    600

ATGCTGAATA CATAGGCATA TAAAGCGACA CCTGCTGAAC TGAAACATCT TAGTAAGCAG    660

AGGAAAAGAA ATCAAAGAGA TTCCCTGAGT AGCGGCGAGC GAAAGGGGAT TAGACCAAAC    720

CACGTTTTTA ATGTGGGGTT GTAGGGTCGA TAACATGGGA TCTTAAGTTT TAGTTGAATA    780

CTTCTGGAAA GTAGAACGAC ACAGGGTGAT AGTCCCGTAA ACGAAAAAAC AAGAGACTCT    840

ATTCGATACC TGAGTAGGGC TAGACACGTG AAACCTAGTC TGAATCTGGG GAGACCACTC    900

TCCAAGTCTA AATACTAGTC AATGACCTAT AGTGAACCAG TACTGTGAAG GAAAGGTGAA    960

AAGAACCCTT GTTAAGGGAG TGAAATAGAA CCTGAAACCA ATAGCTTATA AGCGGTCGAA   1020

GACCTATTAG CTTTTTCGAA AGCAATGGTT GACGGCGTGC CTTTTGCATG ATGAGCCAGG   1080

GAGTTAAGTT AAACGGCGAG GTTAAGGGAT TTACATTCCG GAGCCGAAGC GAAAGCGAGT   1140

TTTAATAGAG CGTTTAGTCG TTTGATTTAG ACACGAAACC AAGTGAGCTA TTTATGACCA   1200

GGTTGAAGCG TGGGTAAGAC CTTGTGGAGG ACCGAACCAG TACATGTTGA AAAATGTTTG   1260

GATGAGTTGT GAATAGGGGT GAAAG                                         1285
```

(2) INFORMATION FOR SEQ ID NO:17:

(i) SEQUENCE CHARACTERISTICS:
(A) LENGTH: 1285 base pairs
(B) TYPE: nucleic acid
(C) STRANDEDNESS: single
(D) TOPOLOGY: linear -continued (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci
(B) STRAIN: FP Vaccine (ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..443
(D) OTHER INFORMATION: /note= "intergenic spacer"

(ix) FEATURE:
(A) NAME/KEY: rRNA
(B) LOCATION: 444..1065
(D) OTHER INFORMATION: /note= "Domain I of the 23S rRNA"

(ix) FEATURE:
(A) NAME/KEY: rRNA
(B) LOCATION: 444..1285
(D) OTHER INFORMATION: /note= "23S rRNA"

(ix) FEATURE:
(A) NAME/KEY: misc_RNA
(B) LOCATION: 1..536
(D) OTHER INFORMATION: /note= "Region A - Region of the Intergenic Spacer"

(ix) FEATURE:
(A) NAME/KEY: rRNA
(B) LOCATION: 958..1088
(D) OTHER INFORMATION: /note= "Region B - The 3' End of Domain I in the 23S rRNA"

(xi) SEQUENCE DESCRIPTION: SEQ ID NO:17:

CATGAAGTCG GAATTGCTAG TAATGGCGTG TCAGCTATAA CGCCGTGAAT ACGTTCCCGG 60

GCCTTGTACA CACCGCCCGT CACATCATGG GAGTTGGTTT TGCCTTAAGT CGTTGACTCA 120

ACCTGCAAAG GAGAGAGGCG CCCAAGGTGA GGCTGATGAC TGGGATGAAG TCGTAACAAG 180

GTAGCCCTAC CGGAAGGTGG GGCTGGATCA CCTCCTTTTA AGGATAAGGA TAACCGTTTT 240

AGGACGGTTT GACTAGGTTG GGCAAGCATT TTTGAAAACT TGTATTCTAT TTCTTTTGCG 300

TTGTTAAGCG TGGGTTACAA AACATTCAGT TTACGATCAA GTATGTTATG TAAATAATAT 360

GGTAACAAGT AAATTCACAT ATAATAATAG ACGTTTAAGA ATATATGTCT TTAGGTGAAG 420

TTAACTTGCA TGGATCAATA ATTTACAGAC CAAGTTAGTA AGAGCTATTG GCGGATGCCT 480

TGGCATTGAC AGGCGATGAA GGATGCGTTT ACCTGCAGTA ATCTTCGGCG AGCTGGTATA 540

AAGCTATGAC CCGGAGGTCT CCGAATGGGG CAACCCGGTA GATTAATCAT CTACCATTAT 600

ATGCTGAATA CATAGGCATA TAAAGCGACA CCTGATGAAC TGAAACATCT TAGTAAGCAG 660

AGGAAAAGAA ATCAAAGAGA TTCCCTGAGT AGCGGCGAGC GAAAGGGGAT TAGACCAAAC 720

CACGTTTTTA ATGTGGGGTT GTAGGGTCGA TAACATGGGA TCTTAAGTTT TAGTTGAATA 780

CTTCTGGAAA GTAGAACGAC ACAGGGTGAT AGTCCCGTAA ACGAAAAAAC AAGAGACTCT 840

ATTCGATACC TGAGTAGGGC TAGACACGTG AAACCTAGTC TGAATCTGGG GAGACCACTC 900

TCCAAGTCTA AATACTAGTC AATGACCTAT AGTGAACCAG TACTGTGAAG GAAAGGTGAA 960

AAGAACCCTT GTTAAGGGAG TGAAATAGAA CCTGAAACCA ATAGCTTATA AGCGGTCGAA 1020

-continued

GACCTATTAG CTTTTTCGAA AGCAATGGTT GACGGCGTGC CTTTTGCATG ATGAGCCAGG 1080

GAGTTAAGTT AAACGGCGAG GTTAAGGGAT TTACATTCCG GAGCCGAAGC GAAAGCGAGT 1140

TTTAATAGAG CGTTTAGTCG TTTGATTTAG ACACGAAACC AAGTGAGCTA TTTATGACCA 1200

GGTTGAAGCG TGGGTAAGAC CTTGTGGAGG ACCGAACCAG TACATGTTGA AAAATGTTTG 1260

GATGAGTTGT GAATAGGGGT GAAAG 1285

(2) INFORMATION FOR SEQ ID NO:18:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia psittaci
(B) STRAIN: GPIC (VR 813)

(ix) FEATURE:
(A) NAME/KEY: rRNA
(B) LOCATION: 1..219
(D) OTHER INFORMATION: /note= "16s rRNA"

(ix) FEATURE:
(A) NAME/KEY: misc_RNA
(B) LOCATION: 220..443
(D) OTHER INFORMATION: /note= "intergenic spacer"

(ix) FEATURE:
(A) NAME/KEY: rRNA
(B) LOCATION: 444..1064
(D) OTHER INFORMATION: /note= "Domain I of the 23S rRNA"

(ix) FEATURE:
(A) NAME/KEY: rRNA
(B) LOCATION: 444..1284
(D) OTHER INFORMATION: /note= "23S rRNA"

(ix) FEATURE:
(A) NAME/KEY: misc_RNA
(B) LOCATION: 1..536
(D) OTHER INFORMATION: /note= "Region A - Region of the Intergenic Spacer"

(ix) FEATURE:
(A) NAME/KEY: rRNA
(B) LOCATION: 958..1087
(D) OTHER INFORMATION: /note= "Region B - The 3' End of Domain I in the 23S rRNA"

(xi) SEQUENCE DESCRIPTION: SEQ ID NO:18:

CATGAAGTCG GAATTGCTAG TAATGGCGTG TCAGCTATAA CGCCGTGAAT ACGTTCCCGG 60

GCCTTGTACA CACCGCCCGT CACATCATGG GAGTTGGTTT TGCCTTAAGT CGTTGACTCA 120

ACCTGCAAAG GAGAGAGGCG CCCAAGGTGA GGCTGATGAC TGGGATGAAG TCGTAACAAG 180

GTAGCCCTAC CGGAAGGTGG GGCTGGATCA CCTCCTTTTA AGGATAAGGA TGGCCGTCTT 240

AGGATGGTTT GACTAGGTTG GGCAAGCGTC TTTGAAAACT TGTATTCTAT TTCTTTTGCA 300

TTGTTAAGCG CTCGTTTCCA AAACATTCAG TTTACGATCA AGTATGTTAT GTAAATAATA 360

TGGTAACAAG TAAATTCACA TATAATAATA GACGTTTAAG AATATCTGTC TTTGGTGAAG 420

TTAACTTGCA TGGATCAATA ATTTACAGAC CAAGTTGTTA AGAGCTATTG GCGGATGCCT 480

-continued

```
TGGCATTGAC AGGCGATGAA GGATGCGTTT ACCTGCAGTA ATCTTCGGCG AGCTGGTATA    540

AAGCTATGAC CCGGAGGTAT CCGAATGGGG TAACCCGGTA GATTAATCGT CTACCATTAT    600

ATACTGAATA CATAGGTATA TAAAGCGACA CCTGCTGAAC TGAAACATCT TAGTAAGCAG    660

AGGAAAATAA ATCAAAGAGA TTCCCTAAGT AGCGGCGAGC GAAAGGGGAG AAGACCAAAC    720

CACGCCTTTG GTGTGGGGTT GTAGGGTCGA TAACATGAGA TCTTAAGTTT TAGTTGAATA    780

CTTCTGGAAA GTAGAACGAT ACAGGGTGAT AGTCCCGTAA ACGAAAGAAC AAGAGACTCT    840

ATTCGATGCC TGAGTAGGGC TAGACACGTG AAACCTAGTC TGAATCTGGG GAGACCACTC    900

TCCAAGTCTA AATACTAGTC AATGACCTAT AGTGAACCAG TACTGTGAAG GAAAGGTGAA    960

AAGAACCCTT GTTAAGGGAG TGAAATAGAA CCTGAAACCA GTAGCTTATA AGCGGTCGGA   1020

GACCTATAGC TTCCTCGGAA GCCATGGTTG ACGGCGTGCC TTTTGCATGA TGAGCCAGGG   1080

AGTTAAGTTA AACGGCGAGG TTAAGGGATC TACATTCCGG AGCCGAAGCG AAAGCGAGTT   1140

TTAATAGAGC GTATAGTCGT TTGATTTAGA CACGAAACCA AGTGAGCTAT TTATGACCAG   1200

GTTGAAGCAT GGGTAAGACC TTGTGGAGGA CCGAACCAGT ACATGTTGAA AAATGTTTGG   1260

ATGAGTTGTG AATAGGGGTG AAAG                                          1284
```

(2) INFORMATION FOR SEQ ID NO:19:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia pecorum
(B) STRAIN: 1710S (ix) FEATURE:
(A) NAME/KEY: rRNA
(B) LOCATION: 1..221
(D) OTHER INFORMATION: /note= "16S rRNA"

(ix) FEATURE:
(A) NAME/KEY: misc_RNA
(B) LOCATION: 222..446
(D) OTHER INFORMATION: /note= "intergenic spacer"

(ix) FEATURE:
(A) NAME/KEY: rRNA
(B) LOCATION: 447..1065
(D) OTHER INFORMATION: /note= "Domain I of the 23S rRNA"

(ix) FEATURE:
(A) NAME/KEY: rRNA
(B) LOCATION: 447..1284
(D) OTHER INFORMATION: /note= "23S rRNA"

(ix) FEATURE:
(A) NAME/KEY: misc_RNA
(B) LOCATION: 1..539
(D) OTHER INFORMATION: /note= "Region A - Region of the Intergenic Spacer"

(ix) FEATURE:
(A) NAME/KEY: rRNA
(B) LOCATION: 961..1088
(D) OTHER INFORMATION: /note= "Region B - The 3' End of Domain I in the 23S"

-continued (xi) SEQUENCE DESCRIPTION: SEQ ID NO:19:

```
CATGAAGTCG GAATTGCTAG TAATGGCGTG TCAGCCATAA CGCCGTGAAT ACGTTCCCGG     60
GCCTTGTACA CACCGCCCGT CACATCATGG GAGTTGGTTT CACCTTAAGT CGTTGACTCA    120
ACCTATTTTT AGGAGGGAGG CGCCCAAGGT GAGGCTGATG ACTGGGATGA AGTCGTAACA    180
AGGTAGCCCT ACCGGAAGGT GGGGCTGGAT CACCTCCTTT TAAGGATAAG GAAAGCTATC    240
AATTGTATAG CTTGACTAGG TTGGGCAAGC ATTTTGCTGT GTATTCTATT TCTTTTGCTT    300
TGTTAAGAGT GGTTTTCGTT ACATTTAGTA TTAATGATCA AGTATGTTAT GTAAATAATC    360
ATGGTAACAA GTATATTTTC ACATATAATA ATAGACGTTT AAGAATATCT GTCTTTGGTG    420
AAGTTATCTT GCATGGATCA AAAATTTACA GACCAAGTTA GTAAGAGCTA TTGGTGGATG    480
CCTTGGCATT GAAAGGCGAT GAAGGATGCG TTTACCTGCA TTAATCTTCG GCGAGCTGGT    540
ATAAAGCTAT GACCCGGAGG TTTCCGAATG GGAAAACCCG ATAGATTAAT AGTCTATCAT    600
TATACGCTGA ATCCATAGGC GTATAAGGCG AAACCTACTG AACTGAAACA TCTTAGTAAG    660
TAGAGGAAAA GAAATCAAAG AGATTCCCTG TGTAGCGGCG AGCGAAAGGG GAACAGTCTA    720
AACCATATTT TTAATATGGG GTTGTAGGGT CGATAACGTG AGATCTTAAG TTTTAGTTGA    780
ATATTTCTGG AAAGTTGAAC GATACAGGGT GATAGTCCCG TAAACGAAAA AACAAAAGAC    840
TCTATTCGAT TCCTGAGTAG AACTAGACAC GTGAAACCTA GTTTGAATCT GGGGAGACCA    900
CTCTCCAAGA CTAAATACTA ATCAATGACC TATAGTGAAC CAGTACTGTA AAGGAAAGGT    960
GAAAAGAACC CTTGTTAAGG GAGTGAAATA GAACCTGAAA CCAGTAGCTT ATAAGCGGTC   1020
GAAGACCTAT AACTCTTCGG AGTGATGGTT GACGGCGTGC CTTTTGCATG ATGAGCCAGG   1080
GAGTTAAGTT AAACGGCGAG GTTAAGGGAT TTACATTCCG GAGCCGAAGC GAAAGCGAGT   1140
TTTAAAAGAG CGTTTAGTCG TTTGATTTAG ACACGAAACC AAGTGATCTA TTTATGACCA   1200
GGTTGAAGCA TTGGTAAGAC TTTGTGGAGG ACCGAACTAG TACCTGTTGA AAAAGGTTTG   1260
GATGAGTTGT GAATAGGGTG AAAG                                          1284
```

(2) INFORMATION FOR SEQ ID NO:20:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia pecorum
(B) STRAIN: BP-1

(ix) FEATURE:
(A) NAME/KEY: rRNA
(B) LOCATION: 1..221
(D) OTHER INFORMATION: /note= "16S rRNA"

(ix) FEATURE:
(A) NAME/KEY: misc_RNA
(B) LOCATION: 222..446
(D) OTHER INFORMATION: /note= "intergenic spacer"

(ix) FEATURE:
(A) NAME/KEY: rRNA
(B) LOCATION: 447..1065
(D) OTHER INFORMATION: /note= "Domain I of the 23S rRNA"

-continued (ix) FEATURE:
(A) NAME/KEY: rRNA
(B) LOCATION: 447..1284
(D) OTHER INFORMATION: /note= "23S rRNA"

(ix) FEATURE:
(A) NAME/KEY: misc_RNA
(B) LOCATION: 1..539
(D) OTHER INFORMATION: /note= "Region A - Region of the Intergenic Spacer"

(ix) FEATURE:
(A) NAME/KEY: rRNA
(B) LOCATION: 961..1088
(D) OTHER INFORMATION: /note= "Region B - The 3' End of Domain I in the 23S rRNA"

(xi) SEQUENCE DESCRIPTION: SEQ ID NO:20:

```
CATGAAGTCG GAATTGCTAG TAATGGCGTG TCAGCCATAA CGCCGTGAAT ACGTTCCCGG     60
GCCTTGTACA CACCGCCCGT CACATCATGG GAGTTGGTTT CACCTTAAGT CGTTGACTCA    120
ACCTATTTTT AGGAGGGAGG CGCCCAAGGT GAGGCTGATG ACTGGGATGA AGTCGTAACA    180
AGGTAGCCCT ACCGGAAGGT GGGGCTGGAT CACCTCCTTT TAAGGATAAG GAAAGCTATC    240
AATTGTATAG CTTGACTAGG TTGGGCAAGC ATTTTGCTGT GTATTCTATT TCTTTTGCTT    300
TGTTAAGAGT GGTTTTCGTT ACATTTAGTA TTAATGATCA AGTATGTTAT GTAAATAATC    360
ATGGTAACAA GTATATTTTC ACATATAATA ATAGACGTTT AAGAATATCT GTCTTTGGTG    420
AAGTTATCTT GCATGGATCA AAAATTTACA GACCAAGTTA GTAAGAGCTA TTGGTGGATG    480
CCTTGGCATT GAAAGGCGAT GAAGGATGCG TTTACCTGCA TTAATCTTCG GCGAGCTGGT    540
ATAAAGCTAT GACCCGGAGG TTTCCGAATG GGAAAACCCG ATAGATTAAT AGTCTATCAT    600
TATACGCTGA ATCCATAGGC GTATAAGGCG AAACCTACTG AACTGAAACA TCTTAGTAAG    660
TAGAGGAAAA GAAATCAAAG AGATTCCCTG TGTAGCGGCG AGCGAAAGGG GAACAGTCTA    720
AACCATATTT TTAATATGGG GTTGTAGGGT CGATAACGTG AGATCTTAAG TTTTAGTTGA    780
ATATTTCTGG AAAGTTGAAC GATACAGGGT GATAGTCCCG TAAACGAAAA AACAAAAGAC    840
TCTATTCGAT TCCTGAGTAG AACTAGACAC GTGAAGCCTA GTTTGAATCT GGGGAGACCA    900
CTCTCCAAGA CTAAATACTA ATCAATGACC TATAGTGAAC CAGTCCTGTA AAGGAAAGGT    960
GAAAAGAACC CTTGTTAAGG GAGTGAAATA GAACCTGAAA CCAGTAGCTT ATAAGCGGTC   1020
GAAGACCTAT AACTCTTCGG AGTGATGGTT GACGGCGTGC CTTTTGCATG ATGAGCCAGG   1080
GAGTTAAGTT AAACGGCGAG GTTAAGGGAT TTACATTCCG GAGCCGAAGC GAAAGCGAGT   1140
TTTAAAAGAG CGTTTAGTCG TTTGATTTAG ACACGAAACC AAGTGATCTA TTTATGACCA   1200
GGTTGAAGCA TTGGTAAGAC TTTGTGGAGG ACCGAACTAG TACCTGTTGA AAAAGGTTTG   1260
GATGAGTTGT GAATAGGGTG AAAG                                          1284
```

(2) INFORMATION FOR SEQ ID NO:21:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO -continued (vi) ORIGINAL SOURCE:
(A) ORGANISM: Chlamydia pecorum
(B) STRAIN: E58

(ix) FEATURE:
(A) NAME/KEY: rRNA
(B) LOCATION: 1..221
(D) OTHER INFORMATION: /note= "16S rRNA"

(ix) FEATURE:
(A) NAME/KEY: misc_RNA
(B) LOCATION: 222..446
(D) OTHER INFORMATION: /note= "intergenic spacer"

(ix) FEATURE:
(A) NAME/KEY: rRNA
(B) LOCATION: 447..1065
(D) OTHER INFORMATION: /note= "Domain I of the 23S rRNA"

(ix) FEATURE:
(A) NAME/KEY: rRNA
(B) LOCATION: 447..1284
(D) OTHER INFORMATION: /note= "23S rRNA"

(ix) FEATURE:
(A) NAME/KEY: misc_RNA
(B) LOCATION: 1..539
(D) OTHER INFORMATION: /note= "Region A - Region of the Intergenic Spacer"

(ix) FEATURE:
(A) NAME/KEY: rRNA
(B) LOCATION: 961..1088
(D) OTHER INFORMATION: /note= "Region B - The 3' End of Domain I in the 23S rRNA"

(xi) SEQUENCE DESCRIPTION: SEQ ID NO:21:

CATGAAGTCG GAATTGCTAG TAATGGCGTG TCAGCCATAA CGCCGTGAAT ACGTTCCCGG 60

GCCTTGTACA CACCGCCCGT CACATCATGG GAGTTGGTTT CACCTTAAGT CGTTGACTCA 120

ACCTATTTTT AGGAGGGAGG CGCCCAAGGT GAGGCTGATG ACTGGGATGA AGTCGTAACA 180

AGGTAGCCCT ACCGGAAGGT GGGGCTGGAT CACCTCCTTT TAAGGATAAG GAAAGCTATC 240

AATTGTATAG CTTGACTAGG TTGGGCAAGC ATTTTGCTGT GTATTCTATT TCTTTTGCTT 300

TGTTAAGAGT GGTTTTCGTT ACATTTAGTA TTAATGATCA AGTATGTTAT GTAAATAATC 360

ATGGTAACAA GTATATTTTC ACATATAATA ATAGACGTTT AAGAATATCT GTCTTTGGTG 420

AAGTTATCTT GCATGGATCA AAAATTTACA GACCAAGTTA GTAAGAGCTA TTGGTGGATG 480

CCTTGGCATT GAAAGGCGAT GAAGGATGCG TTTACCTGCA TTAATCTTCG GCGAGCTGGT 540

ATAAAGCTAT GACCCGGAGG TTTCCGAATG GGAAAACCCG ATAGATTAAT AGTCTATCAT 600

TATACGCTGA ATCCATAGGC GTATAAGGCG AAACCTACTG AACTGAAACA TCTTAGTAAG 660

TAGAGGAAAA GAAATCAAAG AGATTCCCTG TGTAGCGGCG AGCGAAAGGG GAACAGTCTA 720

AACCATATTT TTAATATGGG GTTGTAGGGT CGATAACGTG AGATCTTAAG TTTTAGTTGA 780

ATATTTCTGG AAAGTTGAAC GATACAGGGT GATGGTCCCG TAAACGAAAA AACAAAAGAC 840

TCTATTCGAT TCCTGAGTAG AACTAGACAC GTGAAACCTA GTTTGAATCT GGGGAGACCA 900

CTCTCCAAGA CTAAATACTA ATCAATGACC TATAGTGAAC CAGTACTGTA AAGGAAAGGT 960

GAAAAGAACC CTTGTTAAGG GAGTGAAATA GAACCTGAAA CCAGTAGCTT ATAAGCGGTC 1020

GAAGACCTAT AACTCTTCGG AGTGATGGTT GACGGCGTGC CTTTTGCATG ATGAGCCAGG 1080

GAGTTAAGTT AAACGGCGAG GTTAAGGGAT TTACATTCCG GAGCCGAAGC GAAAGCGAGT 1140

TTTAAAAGAG CGTTTAGTCG TTTGATTTAG ACACGAAACC AAGTGATCTA TTTATGACCA 1200

GGTTGAAGCA TTGGTAAGAC TTTGTGGAGG ACCGAACTAG TACCTGTTGA AAAAGGTTTG 1260

-continued

GATGAGTTGT GAATAGGGTG AAAG 1284

(2) INFORMATION FOR SEQ ID NO:22:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia pecorum
(B) STRAIN: IPA (ix) FEATURE:
(A) NAME/KEY: rRNA
(B) LOCATION: 1..221
(D) OTHER INFORMATION: /note= “16S rRNA”

(ix) FEATURE:
(A) NAME/KEY: misc_RNA
(B) LOCATION: 222..446
(D) OTHER INFORMATION: /note= “intergenic spacer”

(ix) FEATURE:
(A) NAME/KEY: rRNA
(B) LOCATION: 447..1065
(D) OTHER INFORMATION: /note= “Domain I of the 23S rRNA”

(ix) FEATURE:
(A) NAME/KEY: rRNA
(B) LOCATION: 447..1284
(D) OTHER INFORMATION: /note= “23S rRNA”

(ix) FEATURE:
(A) NAME/KEY: misc_RNA
(B) LOCATION: 1..539
(D) OTHER INFORMATION: /note= “Region A - Region of the Intergenic Spacer”

(ix) FEATURE:
(A) NAME/KEY: rRNA
(B) LOCATION: 961..1088
(D) OTHER INFORMATION: /note= “Region B - The 3' End of Domain I in the 23S rRNA”

(xi) SEQUENCE DESCRIPTION: SEQ ID NO:22:

CATGAAGTCG GAATTGCTAG TAATGGCGTG TCAGCCATAA CGCCGTGAAT ACGTTCCCGG 60

GCCTTGTACA CACCGCCCGT CACATCATGG GAGTTGGTTT CACCTTAAGT CGTTGACTCA 120

ACCTATTTTT AGGAGGGAGG CGCCCAAGGT GAGGCTGATG ACTGGGATGA AGTCGTAACA 180

AGGTAGCCCT ACCGGAAGGT GGGGCTGGAT CACCTCCTTT TAAGGATAAG GAAAGCTATC 240

AATTGTATAG CTTGACTAGG TTGGGCAAGC ATTTTGCTGT GTATTCTATT TCTTTTGCTT 300

TGTTAAGAGT GGTTTTCGTT ACATTTAGTA TTAATGATCA AGTATGTTAT GTAAATAATC 360

ATGGTAACAA GTATATTTTC ACATATAATA ATAGACGTTT AAGAATATCT GTCTTTGGTG 420

AAGTTATCTT GCATGGATCA AAAATTTACA GACCAAGTTA GTAAGAGCTA TTGGTGGATG 480

CCTTGGCATT GAAAGGCGAT GAAGGATGCG TTTACCTGCA TTAATCTTCG GCGAGCTGGT 540

ATAAAGCTAT GACCCGGAGG TTTCCGAATG GGAAAACCCG ATAGATTAAT AGTCTATCAT 600

TATACGCTGA ATCCATAGGC GTATAAGGCG AAACCTACTG AACTGAAACA TCTTAGTAAG 660

TAGAGGAAAA GAAATCAAAG AGATTCCCTG TGTAGCGGCG AGCGAAAGGG GAACAGTCTA 720

-continued

```
AACCATATTT TTAATATGGG GTTGTAGGGT CGATAACGTG AGATCTTAAG TTTTAGTTGA    780

ATATTTCTGG AAAGTTGAAC GATACAGGGT GATAGTCCCG TAAACGAAAA AACAAAAGAC    840

TCTATTCGAT TCCTGAGTAG AACTAGACAC GTGAAACCTA GTTTGAATCT GGGGAGACCA    900

CTCTCCAAGA CTAAATACTA ATCAATGACC TATAGTGAAC CAGTACTGTA AAGGAAAGGT    960

GAAAAGAACC CTTGTTAAGG GAGTGAAATA GAACCTGAAA CCAGTAGCTT ATAAGCGGTC   1020

GAAGACCTAT AACTCTTCGG AGTGATGGTT GACGGCGTGC CTTTTGCATG ATGAGCCAGG   1080

GAGTTAAGTT AAACGGCGAG GTTAAGGGAT TTACATTCCG GAGCCGAAGC GAAAGCGAGT   1140

TTTAAAAGAG CGTTTAGTCG TTTGATTTAG ACACGAAACC AAGTGATCTA TTTATGACCA   1200

GGTTGAAGCA TTGGTAAGAC TTTGTGGAGG ACCGAACTAG TACCTGTTGA AAAAGGTTTG   1260

GATGAGTTGT GAATAGGGTG AAAG                                          1284
```

(2) INFORMATION FOR SEQ ID NO:23:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia pecorum
(B) STRAIN: L71

(ix) FEATURE:
(A) NAME/KEY: rRNA
(B) LOCATION: 1..221
(D) OTHER INFORMATION: /note= "16S rRNA"

(ix) FEATURE:
(A) NAME/KEY: misc_RNA
(B) LOCATION: 222..446
(D) OTHER INFORMATION: /note= "intergenic spacer"

(ix) FEATURE:
(A) NAME/KEY: rRNA
(B) LOCATION: 447..1065
(D) OTHER INFORMATION: /note= "Domain I of the 23S rRNA"

(ix) FEATURE:
(A) NAME/KEY: rRNA
(B) LOCATION: 447..1284
(D) OTHER INFORMATION: /note= "23S rRNA"

(ix) FEATURE:
(A) NAME/KEY: misc_RNA
(B) LOCATION: 1..539
(D) OTHER INFORMATION: /note= "Region A - Region of the Intergenic Spacer"

(ix) FEATURE:
(A) NAME/KEY: rRNA
(B) LOCATION: 961..1088
(D) OTHER INFORMATION: /note= "Region B - The 3' End of Domain I in the 23S rRNA"

(xi) SEQUENCE DESCRIPTION: SEQ ID NO:23:

```
CATGAAGTCG GAATTGCTAG TAATGGCGTG TCAGCCATAA CGCCGTGAAT ACGTTCCCGG     60

GCCTTGTACA CACCGCCCGT CACATCATGG GAGTTGGTTT CACCTTAAGT CGTTGACTCA    120

ACCTATTTTT AGGAGGGAGG CGCCCAAGGT GAGGCTGATG ACTGGGATGA AGTCGTAACA    180
```

-continued

```
AGGTAGCCCT ACCGGAAGGT GGGGCTGGAT CACCTCCTTT TAAGGATAAG GAAAGCTATC    240

AATTGTATAG CTTGACTAGG TTGGGCAAGC ATTTTGCTGT GTATTCTATT TCTTTTGCTT    300

TGTTAAGAGT GGTTTTCGTT ACATTTAGTA TTAATGATCA AGTATGTTAT GTAAATAATC    360

ATGGTAACAA GTATATTTTC ACATATAGTA ATAGACGTTT AAGAATATCT GTCTTTGGTG    420

AAGTTATCTT GCATGGATCA AAAATTTACA GACCAAGTTA GTAAGAGCTA TTGGTGGATG    480

CCTTGGCATT GAAAGGCGAT GAAGGATGCG TTTACCTGCA TTAATCTTCG GCGAGCTGGT    540

ATAAAGCTAT GACCCGGAGG TTTCCGAATG GGAAAACCCG ATAGATTAAT AGTCTATCAT    600

TATACGCTGA ATCCATAGGC GTATAAGGCG AAACCTACTG AACTGAAACA TCTTAGTAAG    660

TAGAGGAAAA GAAATCAAAG AGATTCCCTG TGTAGCGGCG AGCGAAAGGG GAACAGTCTA    720

AACCATATTT TTAATATGGG GTTGTAGGGT CGATAACGTG AGATCTTAAG TTTTAGTTGA    780

ATATTTCTGG AAAGTTGAAC GATACAGGGT GATAGTCCCG TAAACGAAAA AACAAAAGAC    840

TCTATTCGAT TCCTGAGTAG AACTAGACAC GTGAAACCTA GTTTGAATCT GGGGAGACCA    900

CTCTCCAAGA CTAAATACTA ATCAATGACC TATAGTGAAC CAGTACTGTA AAGGAAAGGT    960

GAAAAGAACC CTTGTTAAGG GAGTGAAATA GAACCTGAAA CCAGTAGCTT ATAAGCGGTC   1020

GAAGACCTAT AACTCTTCGG AGTGATGGTT GACGGCGTGC CTTTTGCATG ATGAGCCAGG   1080

GAGTTAAGTT AAACGGCGAG GTTAAGGGAT TTACATTCCG GAGCCGAAGC GAAAGCGAGT   1140

TTTAAAAGAG CGTTTAGTCG TTTGATTTAG ACACGAAACC AAGTGATCTA TTTATGACCA   1200

GGTTGAAGCA TTGGTAAGAC TTTGTGGAGG ACCGAACTAG TACCTGTTGA AAAAGGTTTG   1260

GATGAGTTGT GAATAGGGTG AAAG                                          1284
```

(2) INFORMATION FOR SEQ ID NO:24:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia pecorum
(B) STRAIN: Z (ix) FEATURE:
(A) NAME/KEY: rRNA
(B) LOCATION: 1..221
(D) OTHER INFORMATION: /note= "16S rRNA"

(ix) FEATURE:
(A) NAME/KEY: misc_RNA
(B) LOCATION: 222..446
(D) OTHER INFORMATION: /note= "intergenic spacer"

(ix) FEATURE:
(A) NAME/KEY: rRNA
(B) LOCATION: 447..1065
(D) OTHER INFORMATION: /note= "Domain I of the 23S rRNA"

(ix) FEATURE:
(A) NAME/KEY: rRNA
(B) LOCATION: 447..1284
(D) OTHER INFORMATION: /note= "23S rRNA"

(ix) FEATURE:

-continued (A) NAME/KEY: misc_RNA
(B) LOCATION: 1..539
(D) OTHER INFORMATION: /note= "Region A - Region of the Intergenic Spacer"

(ix) FEATURE:
(A) NAME/KEY: rRNA
(B) LOCATION: 961..1088
(D) OTHER INFORMATION: /note= "Region B - The 3' End of Domain I in the 23S rRNA"

(xi) SEQUENCE DESCRIPTION: SEQ ID NO:24:

```
CATGAAGTCG GAATTGCTAG TAATGGCGTG TCAGCCATAA CGCCGTGAAT ACGTTCCCGG     60

GCCTTGTACA CACCGCCCGT CACATCATGG GAGTTGGTTT CACCTTAAGT CGTTGACTCA    120

ACCTATTTTT AGGAGGGAGG CGCCCAAGGT GAGGCTGATG ACTGGGATGA AGTCGTAACA    180

AGGTAGCCCT ACCGGAAGGT GGGGCTGGAT CACCTCCTTT TAAGGATAAG GAAAGCTATC    240

AATTGTATAG CTTGACTAGG TTGGGCAAGC ATTTTGCTGT GTATTCTATT TCTTTTGCTT    300

TGTTAAGAGT GGTTTTCGTT ACATTTAGTA TTAATGATCA AGTATGTTAT GTAAATAATC    360

ATGGTAACAA GTATATTTTC ACATATAATA ATAGACGTTT AAGAATATCT GTCTTTGGTG    420

AAGTTATCTT GCATGGATCA AAAATTTACA GACCAAGTTA GTAAGAGCTA TTGGTGGATG    480

CCTTGGCATT GAAAGGCGAT GAAGGATGCG TTTACCTGCA TTAATCTTCG GCGAGCTGGT    540

ATAAAGCTAT GACCCGGAGG TTTCCGAATG GGAAAACCCG ATAGATTAAT AGTCTATCAT    600

TATACGCTGA ATCCATAGGC GTATAAGGCG AAACCTACTG AACTGAAACA TCTTAGTAAG    660

TAGAGGAAAA GAAATCAAAG AGATTCCCTG TGTAGCGGCG AGCGAAAGGG GAACAGTCTA    720

AACCATATTT TTAATATGGG GTTGTAGGGT CGATAACGTG AGATCTTAAG TTTTAGTTGA    780

ATATTTCTGG AAAGTTGAAC GATACAGGGT GATAGTCCCG TAAACGAAAA AACAAAAGAC    840

TCTATTCGAT TCCTGAGTAG AACTAGACAC GTGAAACCTA GTTTGAATCT GGGGAGACCA    900

CTCTCCAAGA CTAAATACTA ATCAATGACC TATAGTGAAC CAGTACTGTA AAGGAAAGGT    960

GAAAAGAACC CTTGTTAAGG GAGTGAAATA GAACCTGAAA CCAGTAGCTT ATAAGCGGTC   1020

GAAGACCTAT AACTCTTCGG AGTGATGGTT GACGGCGTGC CTTTTGCATG ATGAGCCAGG   1080

GAGTTAAGTT AAACGGCGAG GTTAAGGGAT TTACATTCCG GAGCCGAAGC GAAAGCGAGT   1140

TTTAAAAGAG CGTTTAGTCG TTTGATTTAG ACACGAAACC AAGTGATCTA TTTATGACCA   1200

GGTTGAAGCA TTGGTAAGAC TTTGTGGAGG ACCGAACTAG TACCTGTTGA AAAAGGTTTG   1260

GATGAGTTGT GAATAGGGTG AAAG                                          1284
```

(2) INFORMATION FOR SEQ ID NO:25:

(i) SEQUENCE CHARACTERISTICS:
(A) LENGTH: 1282 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia pneumoniae
(B) STRAIN: CM-1

(ix) FEATURE:
(A) NAME/KEY: rRNA
(B) LOCATION: 1..220

-continued (D) OTHER INFORMATION: /note= "16S rRNA"

(ix) FEATURE:
(A) NAME/KEY: misc_RNA
(B) LOCATION: 221..442
(D) OTHER INFORMATION: /note= "intergenic spacer"

(ix) FEATURE:
(A) NAME/KEY: rRNA
(B) LOCATION: 443..1061
(D) OTHER INFORMATION: /note= "Domain I of the 23S rRNA"

(ix) FEATURE:
(A) NAME/KEY: rRNA
(B) LOCATION: 443..1282
(D) OTHER INFORMATION: /note= "23S rRNA"

(ix) FEATURE:
(A) NAME/KEY: misc_RNA
(B) LOCATION: 1..535
(D) OTHER INFORMATION: /note= "Region A - Region of the Intergenic Spacer"

(ix) FEATURE:
(A) NAME/KEY: rRNA
(B) LOCATION: 957..1084
(D) OTHER INFORMATION: /note= "Region B - The 3' End of Domain I in the 23S rRNA"

(xi) SEQUENCE DESCRIPTION: SEQ ID NO:25:

CATGAAGTCG GAATTGCTAG TAATGGCGTG TCAGCTATAA CGCCGTGAAT ACGTTCCCGG 60

GCCTTGTACA CACCGCCCGT CACATCATGG GAGTTGGTTT TGCCTTAAGT CGTTGACTCA 120

ACCTGCAAAG GAGAGAGGCG CCCAAGGTGA GGCTGATGAC TGGGATGAAG TCGTAACAAG 180

GTAGCCCTAC CGGAAGGTGG GGCTGGATCA CCTCCTTTTT AAGGACAAGG AAGGTTGTTT 240

TTAACAACCC GACTAGGTTG GGCAAGTATT TTATATTCCG CATTCTATTT CTTTTGCATT 300

GTTAAGGTTG TTTTCAAAAC ATTCAGTATA TGATCAAGTA TGTTATGTAA ATAATCATGG 360

TAACAAGTAT TTTTCACATA TAATAATAGA CGTTTAAGAA TATCTGTCTT TAGGTGAAGT 420

TAACTTGCAT GGATCAAAAA TTTACAGACC AAGTTGTTAA GAGCTATTGG CGGATGCCTT 480

GGCATTGACA GGCGATGAAG GATGCGTTTA CCTGCAGTAA TCTTCGGTGA GCTGGTATAG 540

AGCTATGACC CGGAGGTATC CGAATGGGGC AACCCGATAG ACTAATAGTC TATCATTATA 600

TGTTGAATAC ATAGGCATAT AAGGCGACAC CCGCTGAACT GAAACATCTT AGTAAGCGGA 660

GGAAAAGAAA TCAAAGAGAT TCCCTGTGTA GCGGCGAGCG AAAGGGGAAC AGCCTAAACC 720

ATATTTTTAA TATGGGGTTG TAGGGTCGAT AACATGGGAT CTTAAGTTTT AGTTGAATAC 780

TTCTGGAAAG TTGAACGATA CAGGGTGATA GTCCCGTAAA CGAAAAAACA AAAGACGCTA 840

ATCGATACCT GAGTAGGGCT AGACACGTGA AACCTAGTCT GAATCTGGGG AGACCACTCT 900

CCAAGGCTAA ATACTAGTCA ATGACCTATA GTGAACCAGT ACTGTGAAGG AAAGGTGAAA 960

AGAACCCTTG TTAAGGGAGT GAAATAGAAC CTGAAACCAG TAGCTTATAA GCGGTCGGAG 1020

ACCTATAACT CTTCGGAGTA ATGGTTGACG GCGTGCCTTT TGCATGATGA GCCAGGGAGT 1080

TAAGTTAAAC GGCGAGATTA AGGGATTTAC ATTCCGGAGT CGAAGCGAAA GCGAGTTTTA 1140

AAAGAGCGTT TTAGTCGTTT GATTTAGACA CGAAACCAAG TGAGCTATTT ATGACCAGGT 1200

TGAAGCATTG GTAAGACTTT GTGGAGGACC GAACCAGTAC ATGTTGAAAA ATGTTTGGAT 1260

GAGTTGTGAA TAGGGGTGAA AG 1282

(2) INFORMATION FOR SEQ ID NO:26:

(i) SEQUENCE CHARACTERISTICS:

-continued (A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia pneumoniae
(B) STRAIN: CWL-029

(ix) FEATURE:
(A) NAME/KEY: rRNA
(B) LOCATION: 1..221
(D) OTHER INFORMATION: /note= "16S rRNA"

(ix) FEATURE:
(A) NAME/KEY: misc_RNA
(B) LOCATION: 222..444
(D) OTHER INFORMATION: /note= "intergenic spacer"

(ix) FEATURE:
(A) NAME/KEY: rRNA
(B) LOCATION: 445..1063
(D) OTHER INFORMATION: /note= "Domain I of the 23S rRNA"

(ix) FEATURE:
(A) NAME/KEY: rRNA
(B) LOCATION: 445..1284
(D) OTHER INFORMATION: /note= "23S rRNA"

(ix) FEATURE:
(A) NAME/KEY: misc_RNA
(B) LOCATION: 1..537
(D) OTHER INFORMATION: /note= "Region A - Region of the Intergenic Spacer"

(ix) FEATURE:
(A) NAME/KEY: rRNA
(B) LOCATION: 959..1086
(D) OTHER INFORMATION: /note= "Region B - The 3' End of Domain I in the 23S rRNA"

(xi) SEQUENCE DESCRIPTION: SEQ ID NO:26:

CATGAAGTCG GAATTGCTAG TAATGGCGTG TCAGCCATAA CGCCGTGAAT ACGTTCTCGG 60

GCCTTGTACA CACCGCCCGT CACATCATGG GAGTTGGTTT TACCTTAAGT CGTTGACTCA 120

ACCTATTTAT AGGAGAGAGG CGCCCAAGGT GAGGCTGATG ACTGGGATGA AGTCGTAACA 180

AGGTAGCCCT ACCGGAAGGT GGGGCTGGAT CACCTCCTTT TTAAGGACAA GGAAGGTTGT 240

TTTTAACAAC CCGACTAGGT TGGGCAAGTA TTTTATATTC CGCATTCTAT TTCTTTTGCA 300

TTGTTAAGGT TGTTTTCAAA ACATTCAGTA TATGATCAAG TATGTTATGT AAATAATCAT 360

GGTAACAAGT ATTTTTCACA TATAATAATA GACGTTTAAG AATATCTGTC TTTAGGTGAA 420

GTTAACTTGC ATGGATCAAA AATTTACAGA CCAAGTTGTT AAGAGCTATT GGCGGATGCC 480

TTGCCATTGA CAGGCGATGA AGGATGCGTT TACCTGCAGT AATCTTCGGT GAGCTGGTAT 540

AGAGCTATGA CCCGGAGGTA TCCGAATGGG GCAACCCGAT AGACTAATAG TCTATCATTA 600

TATGTTGAAT ACATAGGCAT ATAAGGCGAC ACCCGCTGAA CTGAAACATC TTAGTAAGCG 660

GAGGAAAAGA AATCAAAGAG ATTCCCTGTG TAGCGGCGAG CGAAAGGGGA ACAGCCTAAA 720

CCATATTTTT AATATGGGGT TGTAGGGTCG ACAACATGGG ATCTTAAGTT TTAGTTGAAT 780

ACTTCTGGAA AGTTGAACGA TACAGGGTGA TAGTCCCGTA AACGAAAAAA CAAAAGACGC 840

TAATCGATAC CTGAGTAGGG CTAGACACGT GAAACCTAGT CTGAATCTGG GGAGACCACT 900

-continued

```
CTCCAAGGCT AAATACTAGT CAATGACCTA TAGTGAACCA GTACTGTGAA GGAAAGGTGA    960

AAAGAACCCT TGTTAAGGGA GTGAAATAGA ACCTGAAACC AGTAGCTTAT AAGCGGTCGG   1020

AGACCTATAA CTCTTCGGAG TAATGGTTGA CGGCGTGCCT TTTGCATGAT GAGCCAGGGA   1080

GTTAAGTTAA ACGGCGAGAT TAAGGGATTT ACATTCCGGA GTCGAAGCGA AAGCGAGTTT   1140

TAAAAGAGCG TTTTAGTCGT TTGATTTAGA CACGAAACCA AGTGAGCTAT TTATGACCAG   1200

GTTGAAGCAT TGGTAAGACT TTGTGGAGGA CCGAACCAGT ACATGTTGAA AAATGTTTGG   1260

ATGAGTTGTG AATAGGGGTG AAAG                                          1284
```

(2) INFORMATION FOR SEQ ID NO:27:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia pneumoniae
(B) STRAIN: CWL-1011

(ix) FEATURE:
(A) NAME/KEY: rRNA
(B) LOCATION: 1..221
(D) OTHER INFORMATION: /note= "16S rRNA"

(ix) FEATURE:
(A) NAME/KEY: misc_RNA
(B) LOCATION: 222..444
(D) OTHER INFORMATION: /note= "intergenic spacer"

(ix) FEATURE:
(A) NAME/KEY: rRNA
(B) LOCATION: 445..1063
(D) OTHER INFORMATION: /note= "Domain I of the 23S rRNA"

(ix) FEATURE:
(A) NAME/KEY: rRNA
(B) LOCATION: 445..1284
(D) OTHER INFORMATION: /note= "23S rRNA"

(ix) FEATURE:
(A) NAME/KEY: misc_RNA
(B) LOCATION: 1..537
(D) OTHER INFORMATION: /note= "Region A - Region of the Intergenic Spacer"

(ix) FEATURE:
(A) NAME/KEY: rRNA
(B) LOCATION: 959..1086
(D) OTHER INFORMATION: /note= "Region B - The 3' End of Domain I in the 23S rRNA"

(xi) SEQUENCE DESCRIPTION: SEQ ID NO:27:

```
CATGAAGTCG GAATTGCTAG TAATGGCGTG TCAGCCATAA CGCCGTGAAT ACGTTCTCGG     60

GCCTTGTACA CACCGCCCGT CACATCATGG GAGTTGGTTT TACCTTAAGT CGTTGACTCA    120

ACCTATTTAT AGGAGAGAGG CGCCCAAGGT GAGGCTGATG ACTGGGATGA AGTCGTAACA    180

AGGTAGCCCT ACCGGAAGGT GGGGCTGGAT CACCTCCTTT TTAAGGACAA GGAAGGTTGT    240

TTTTAACAAC CCGACTAGGT TGGGCAAGTA TTTTATATTC CGCATTCTAT TTCTTTTGCA    300

TTGTTAAGGT TGTTTTCAAA ACATTCAGTA TATGATCAAG TATGTTATGT AAATAATCAT    360
```

-continued

```
GGTAACAAGT ATTTTTCACA TATAATAATA GACGTTTAAG AATATCTGTC TTTAGGTGAA    420

GTTAACTTGC ATGGATCAAA AATTTACAGA CCAAGTTGTT AAGAGCTATT GGCGGATGCC    480

TTGGCATTGA CAGGCGATGA AGGATGCGTT TACCTGCAGT AATCTTCGGT GAGCTGGTAT    540

AGAGCTATGA CCCGGAGGTA TCCGAATGGG GCAACCCGAT AGACTAATAG TCCATCATTA    600

TATGTTGAAT ACATAGGCAT ATAAGGCGAC ACCCGCTGAA CTGAAACATC TTAGTAAGCG    660

GAGGAAAAGA AATCAAAGAG ATTCCCTGTG TAGCGGCGAG CGAAAGGGGA ACAGCCTAAA    720

CCATATTTTT AATATGGGGT TGTAGGGTCG ATAACATGGG ATCTTAAGTT TTAGTTGAAT    780

ACTTCTGGAA AGTTGAACGA TACAGGGTGA TAGTCCCGTT AACGAAAAAA CAAAAGACGC    840

TAATCGATAC CTGAGTAGGG CTAGACACGT GAAACCTAGT CTGAATCTGG GGAGACCACT    900

CTCCAAGGCT AAATACTAGT CAATGACCTA TAGTGAACCA GTACTGTGAA GGAAAGGTGA    960

AAAGAACCCT TGTTAAGGGA GCGAAATAGA ACCTGAAACC AGTAGCTTAT AAGCGGTCGG   1020

AGACCTATAA CTCTTCGGAG TAATGGTTGA CGGCGTGCCT TTTGCATGAT GAGCCAGGGA   1080

GTTAAGTTAA ACGGCGGGAT TAAGGGATTT ACATTCCGGA GTCGAAGCGA AAGCGAGTTT   1140

TAAAAGAGCG TTTTAGTCGT TTGATTTAGA CACGAAACCA AGTGAGCTAT TTATGACCAG   1200

GTTGAAGCAT TGGTAAGACT TTGTGGAGGA CCGAACCAGT ACATGTTGAA AAATGTTTGG   1260

ATGAGTTGTG AATAGGGGTG AAAG                                          1284
```

(2) INFORMATION FOR SEQ ID NO:28:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia pneumoniae
(B) STRAIN: FML-12

(ix) FEATURE:
(A) NAME/KEY: rRNA
(B) LOCATION: 1..221
(D) OTHER INFORMATION: /note= "16S rRNA"

(ix) FEATURE:
(A) NAME/KEY: misc_RNA
(B) LOCATION: 222..444
(D) OTHER INFORMATION: /note= "intergenic spacer"

(ix) FEATURE:
(A) NAME/KEY: rRNA
(B) LOCATION: 445..1063
(D) OTHER INFORMATION: /note= "Domain I of the 23S rRNA"

(ix) FEATURE:
(A) NAME/KEY: rRNA
(B) LOCATION: 445..1284
(D) OTHER INFORMATION: /note= "23S rRNA"

(ix) FEATURE:
(A) NAME/KEY: misc_RNA
(B) LOCATION: 1..537
(D) OTHER INFORMATION: /note= "Region A - Region of the Intergenic Spacer"

(ix) FEATURE:
(A) NAME/KEY: rRNA

-continued (B) LOCATION: 959..1086
(D) OTHER INFORMATION: /note= "Region B - The 3' End of Domain I in the 23S rRNA"

(xi) SEQUENCE DESCRIPTION: SEQ ID NO:28:

```
CATGAAGTCG GAATTGCTAG TAATGGCGTG TCAGCCATAA CGCCGTGAAT ACGTTCTCGG     60
GCCTTGTACA CACCGCCCGT CACATCATGG GAGTTGGTTT TACCTTAAGT CGTTGACTCA    120
ACCTATTTAT AGGAGAGAGG CGCCCAAGGT GAGGCTGATG ACTGGGATGA AGTCGTAACA    180
AGGTAGCCCT ACCGGAAGGT GGGGCTGGAT CACCTCCTTT TTAAGGACAA GGAAGGTTGT    240
TTTTAACAAC CCGACTAGGT TGGGCAAGTA TTTTATATTC CGCATTCTAT TTCTTTTGCA    300
TTGTTAAGGT TGTTTTCAAA ACATTCAGTA TATGATCAAG TATGTTATGT AAATAATCAT    360
GGTAACAAGT ATTTTTCACA TATAATAATA GACGTTTAAG AATATCTGTC TTTAGGTGAA    420
GTTAACTTGC ATGGATCAAA AATTTACAGA CCAAGTTGTT AAGAGCTATT GGCGGATGCC    480
TTGGCATTGA CAGGCGATGA AGGATGCGTT TACCTGCAGT AATCTTCGGT GAGCTGGTAT    540
AGAGCTATGA CCCGGAGGTA TCCGAATGGG GCAACCCGAT AGACTAATAG TCTATCATTA    600
TATGTTGAAT ACATAGGCAT ATAAGGCGAC ACCCGCTGAA CTGAAACATC TTAGTAAGCG    660
GAGGAAAAGA AATCAAAGAG ATTCCCTGTG TAGCGGCGAG CGAAAGGGGA ACAGCCTAAA    720
CCATATTTTT AATATGGGGT TGTAGGGTCG ATAACATGGG ATCTTAAGTT TTAGTTGAAT    780
ACTTCTGGAA AGTTGAACGA TACAGGGTGA TAGTCCCGTA AACGAAAAAA CAAAAGACGC    840
TAATCGATAC CTGAGTAGGG CTAGACACGT GAAACCTAGT CTGAATCTGG GGAGACCACT    900
CTCCAAGGCT AAATACTAGT CAATGACCTA TAGTGAACCA GTACTGTGAA GGAAAGGTGA    960
AAAGAACCCT TGTTAAGGGA GTGAAATAGA ACCTGAAACC AGTAGCTTAT AAGCGGTCGG   1020
AGACCTATAA CTCTTCGGAG TAATGGTTGA CGGCGTGCCT TTTGCATGAT GAGCCAGGGA   1080
GTTAAGTTAA ACGGCGAGAT TAAGGGATTT ACATTCCGGA GTCGAAGCGA AAGCGAGTTT   1140
TAAAAGAGCG TTTTAGTCGT TTGATTTAGA CACGAAACCA AGTGAGCTAT TTATGACCAG   1200
GTTGAAGCAT TGGTAAGACT TTGTGGAGGA CCGAACCAGT ACATGTTGAA AAATGTTTGG   1260
ATGAGTTGTG AATAGGGGTG AAAG                                          1284
```

(2) INFORMATION FOR SEQ ID NO:29:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia pneumoniae
(B) STRAIN: FML-16

(ix) FEATURE:
(A) NAME/KEY: rRNA
(B) LOCATION: 1..221
(D) OTHER INFORMATION: /note= "16S rRNA"

(ix) FEATURE:
(A) NAME/KEY: misc_RNA
(B) LOCATION: 222..444
(D) OTHER INFORMATION: /note= "intergenic spacer"

-continued (ix) FEATURE:
(A) NAME/KEY: rRNA
(B) LOCATION: 445..1063
(D) OTHER INFORMATION: /note= "Domain I of the 23S rRNA"

(ix) FEATURE:
(A) NAME/KEY: rRNA
(B) LOCATION: 445..1284
(D) OTHER INFORMATION: /note= "23S rRNA"

(ix) FEATURE:
(A) NAME/KEY: misc_RNA
(B) LOCATION: 1..537
(D) OTHER INFORMATION: /note= "Region A - Region of the Intergenic Spacer"

(ix) FEATURE:
(A) NAME/KEY: rRNA
(B) LOCATION: 959..1086
(D) OTHER INFORMATION: /note= "Region B - The 3' End of Domain I in the 23S rRNA"

(xi) SEQUENCE DESCRIPTION: SEQ ID NO:29:

```
CATGAAGTCG GAATTGCTAG TAATGGCGTG TCAGCCATAA CGCCGTGAAT ACGTTCTCGG     60
GCCTTGTACA CACCGCCCGT CACATCATGG GAGTTGGTTT TACCTTAAGT CGTTGACTCA    120
ACCTATTTAT AGGAGAGAGG CGCCCAAGGT GAGGCTGATG ACTGGGATGA AGTCGTAACA    180
AGGTAGCCCT ACCGGAAGGT GGGGCTGGAT CACCTCCTTT TTAAGGACAA GGAAGGTTGT    240
TTTTAACAAC CCGACTAGGT TGGGCAAGTA TTTTATATTC CGCATTCTAT TTCTTTTGCA    300
TTGTTAAGGT TGTTTTCAAA ACATTCAGTA TATGATCAAG TATGTTATGT AAATAATCAT    360
GGTAACAAGT ATTTTTCACA TATAATAATA GACGTTTAAG AATATCTGTC TTTAGGTGAA    420
GTTAACTTGC ATGGATCAAA AATTTACAGA CCAAGTTGTT AAGAGCTATT GGCGGATGCC    480
TTGGCATTGA CAGGCGATGA AGGATGCGTT TACCTGCAGT AATCTTCGGT GAGCTGGTAT    540
AGAGCTATGA CCCGGAGGTA TCCGAATGGG GCAACCCGAT AGACTAATAG TCTATCATTA    600
TATGTTGAAT ACATAGGCAT ATAAGGCGAC ACCCGCTGAA CTGAAACATC TTAGTAAGCG    660
GAGGAAAAGA AATCAAAGAG ATTCCCTGTG TAGCGGCGAG CGAAAGGGGA ACAGCCTAAA    720
CCATATTTTT AATATGGGGT TGTAGGGTCG ATAACATGGG ATCTTAAGTT TTAGTTGAAT    780
ACTTCTGGAA AGTTGAACGA TACAGGGTGA TAGTCCCGTA AACGAAAAAA CAAAAGACGC    840
TAATCGATAC CTGAGTAGGG CTAGACACGT GAAACCTAGT CTGAATCTGG GGAGACCACT    900
CTCCAAGGCT AAATACTAGT CAATGACCTA TAGTGAACCA GTACTGTGAA GGAAAGGTGA    960
AAAGAACCCT TGTTAAGGGA GTGAAATAGA ACCTGAAACC AGTAGCTTAT AAGCGGTCGG   1020
AGACCTATAA CTCTTCGGAG TAATGGTTGA CGGCGTGCCT TTTGCATGAT GAGCCAGGGA   1080
GTTAAGTTAA ACGGCGAGAT TAAGGGATTT ACATTCCGGA GTCGAAGCGA AAGCGAGTTT   1140
TAAAAGAGCG TTTTAGTCGT TTGATTTAGA CACGAAACCA AGTGAGCTAT TTATGACCAG   1200
GTTGAAGCAT TGGTAAGACT TTGTGGAGGA CCGAACCAGT ACATGTTGAA AAATGTTTGG   1260
ATGAGTTGTG AATAGGGGTG AAAG                                          1284
```

(2) INFORMATION FOR SEQ ID NO:30:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA -continued (iii) HYPOTHETICAL: NO (iv) ANTI-SENSE: NO (vi) ORIGINAL SOURCE:
(A) ORGANISM: Chlamydia pneumoniae
(B) STRAIN: N16

(ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 222..444
(D) OTHER INFORMATION: /note= "intergenic spacer"

(ix) FEATURE:
(A) NAME/KEY: rRNA
(B) LOCATION: 445..1063
(D) OTHER INFORMATION: /note= "Domain I of the 23S rRNA"

(ix) FEATURE:
(A) NAME/KEY: rRNA
(B) LOCATION: 445..1284
(D) OTHER INFORMATION: /note= "23S rRNA"

(ix) FEATURE:
(A) NAME/KEY: misc_RNA
(B) LOCATION: 1..537
(D) OTHER INFORMATION: /note= "Region A - Region of the Intergenic Spacer"

(ix) FEATURE:
(A) NAME/KEY: rRNA
(B) LOCATION: 959..1086
(D) OTHER INFORMATION: /note= "Region B - The 3' End of Domain I in the 23S rRNA"

(xi) SEQUENCE DESCRIPTION: SEQ ID NO:30:

CATGAAGTCG GAATTGCTAG TAATGGCGTG TCAGCCATAA CGCCGTGAAT ACGTTCCCGG 60

GCCTTGTACA CACCGCCCGT CACATCATGG GAGTTGGTTT TACCTTAAGT CGTTGGCTCA 120

ACCTATTTAT AGGAGAGAGG CGCCCAAGGT GAGGCTGATG ACTGGGATGA AGTCGTAACA 180

AGGTAGCCCT ACCGGAAGGT GGGGCTGGAT CACCTCCTTT TTAAGGACAA GGAAGGTTGT 240

TTTTAACAAC CTGACTAGGT TGGGCAAGTA TTTTATGTTC CGCATTCTAT TTCTTTTGCA 300

TTGTTAAGGT TGTTTTCAAA ACATTCAGTA TATGATCAAG TATGTTATGT AAATAATCAT 360

GGTAACAAGT ATTTTTCACA TATAATAATA GACGTTTAAG AATATCTGTC TTTAGGTGAA 420

GTTAACTTGC ATGGATCAAA AATTTACAGA CCAAGTTGTT AAGAGCTATT GGCGGATGCC 480

TTGGCATTGA CAGGCGATGA AGGATGCGTT TACCTGCAGT AATCTTCGGT GAGCTGGTAT 540

AGAGCTATGA CCCGGAGGTA TCCGAATGGG GCAACCCGAT AGACTAATAG TCTATCATTA 600

TATGCTGAAT ACATAGGCAT ATAAGGCGAC ACCCGTTGAA CTGAAACATC TTAGTAAGCG 660

GAGGAAAAGA AATCAAAGAG ATTCCCTGTG TAGCGGCGAG CGAAAGGGGA ACAGCCTAAA 720

CCATATTTTT AATATGGGGT TGTAGGGTCG ATAACATGGG ATCTTAAGTT TTAGTTGAAT 780

ACTTCTGGAA AGTTGAACGA TACAGGGTGA TAGTCCCGTA AACGAAAAAA CAAAAGGCAC 840

TAATCGATAC CTGAGTAGGG CTAGACACGT GAAACCTAGT CTGAATCTGG GGAGACCACT 900

CTCTAAGGCT AAATACTAGT CAATGACCTA TAGTGAACCA GTACTGTGAA GGAAAGGTGA 960

AAAGAACCCT TGTTAAGGGA GTGAAATAGA ACCTGAAACC AGTAGCTTAT AAGCGGTCGG 1020

AGACCTATAA CTCTTCGGAG TAATGGTTGA CGGCGTGCCT TTTGCATGAT GAGCCAGGGA 1080

GTTAAGTTAA ACGGCGAGAT TAAGGGATTT ACATTCCGGA GTCGAAGCGA AAGCGAGTTT 1140

-continued

TAAAAGAGCG TTTTAGTCGT TTGATTTAGA CACGAAACCA AGTGAGCTAT TTATGACCAG 1200

GTTAAAGCAT TGGTAAGACT TTGTGGAGGA CCGAACCAGT ACATGTTGAA AAATGTTTGG 1260

ATGAGTTGTG AATAGGGGTG AAAG 1284

(2) INFORMATION FOR SEQ ID NO:31:

(i) SEQUENCE CHARACTERISTICS:
(A) LENGTH: 1284 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia pneumoniae
(B) STRAIN: TW-183

(ix) FEATURE:
(A) NAME/KEY: rRNA
(B) LOCATION: 1..221
(D) OTHER INFORMATION: /note= "16S rRNA"

(ix) FEATURE:
(A) NAME/KEY: misc_RNA
(B) LOCATION: 222..444
(D) OTHER INFORMATION: /note= "intergenic spacer"

(ix) FEATURE:
(A) NAME/KEY: rRNA
(B) LOCATION: 445..1063
(D) OTHER INFORMATION: /note= "Domain I of the 23S rRNA"

(ix) FEATURE:
(A) NAME/KEY: rRNA
(B) LOCATION: 445..1284
(D) OTHER INFORMATION: /note= "23S rRNA"

(ix) FEATURE:
(A) NAME/KEY: misc_RNA
(B) LOCATION: 1..537
(D) OTHER INFORMATION: /note= "Region A - Region of the Intergenic Spacer"

(ix) FEATURE:
(A) NAME/KEY: rRNA
(B) LOCATION: 959..1086
(D) OTHER INFORMATION: /note= "Region B - The 3' End of Domain I in the 23S rRNA"

(xi) SEQUENCE DESCRIPTION: SEQ ID NO:31:

CATGAAGTCG GAATTGCTAG TAATGGCGTG TCAGCCATAA CGCCGTGAAT ACGTTCTCGG 60

GCCTTGTACA CACCGCCCGT CACATCATGG GAGTTGGTTT TACCTTAAGT CGTTGACTCA 120

ACCTATTTAT AGGAGAGAGG CGCCCAAGGT GAGGCTGATG ACTGGGATGA AGTCGTAACA 180

AGGTAGCCCT ACCGGAAGGT GGGGCTGGAT CACCTCCTTT TTAAGGACAA GGAAGGTTGT 240

TTTTAACAAC CCGACTAGGT TGGGCAAGTA TTTTATATTC CGCATTCTAT TTCTTTTGCA 300

TTGTTAAGGT TGTTTTCAAA ACATTCAGTA TATGATCAAG TATGTTATGT AAATAATCAT 360

GGTAACAAGT ATTTTTCACA TATAATAATA GACGTTTAAG AATATCTGTC TTTAGGTGAA 420

GTTAACTTGC ATGGATCAAA AATTTACAGA CCAAGTTGTT AAGAGCTATT GGCGGATGCC 480

TTGGCATTGA CAGGCGATGA AGGATGCGTT TACCTGCAGT AATCTTCGGT GAGCTGGTAT 540

AGAGCTATGA CCCGGAGGTA TCCGAATGGG GCAACCCGAT AGACTAATAG TCTATCATTA 600

-continued

```
TATGTTGAAT ACATAGGCAT ATAAGGCGAC ACCCGCTGAA CTGAAACATC TTAGTAAGCG    660

GAGGAAAAGA AATCAAAGAG ATTCCCTGTG TAGCGGCGAG CGAAAGGGGA ACAGCCTAAA    720

CCATATTTTT AATATGGGGT TGTAGGGTCG ATAACATGGG ATCTTAAGTT TTAGTTGAAT    780

ACTTCTGGAA AGTTGAACGA TACAGGGTGA TAGTCCCGTA AACGAAAAAA CAAAAGACGC    840

TAATCGATAC CTGAGTAGGG CTAGACACGT GAAACCTAGT CTGAATCTGG GGAGACCACT    900

CTCCAAGGCT AAATACTAGT CAATGACCTA TAGTGAACCA GTACTGTGAA GGAAAGGTGA    960

AAAGAACCCT TGTTAAGGGA GTGAAATAGA ACCTGAAACC AGTAGCTTAT AAGCGGTCGG   1020

AGACCTATAA CTCTTCGGAG TAATGGTTGA CGGCGTGCCT TTTGCATGAT GAGCCAGGGA   1080

GTTAAGTTAA ACGGCGAGAT TAAGGGATTT ACATTCCGGA GTCGAAGCGA AAGCGAGTTT   1140

TAAAAGAGCG TTTTAGTCGT TTGATTTAGA CACGAAACCA AGTGAGCTAT TTATGACCAG   1200

GTTGAAGCAT TGGTAAGACT TTGTGGAGGA CCGAACCAGT ACATGTTGAA AAATGTTTGG   1260

ATGAGTTGTG AATAGGGGTG AAAG                                          1284
```

(2) INFORMATION FOR SEQ ID NO:32:

(i) SEQUENCE CHARACTERISTICS:
(A) LENGTH: 1304 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia trachomatis
(B) STRAIN: A/Har-13

(ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..462
(D) OTHER INFORMATION: /note= "intergenic spacer"

(ix) FEATURE:
(A) NAME/KEY: rRNA
(B) LOCATION: 463..1084
(D) OTHER INFORMATION: /note= "Domain I of the 23S rRNA"

(ix) FEATURE:
(A) NAME/KEY: rRNA
(B) LOCATION: 463..1304
(D) OTHER INFORMATION: /note= "23S rRNA"

(ix) FEATURE:
(A) NAME/KEY: misc_RNA
(B) LOCATION: 1..555
(D) OTHER INFORMATION: /note= "Region A - Region of the Intergenic Spacer"

(ix) FEATURE:
(A) NAME/KEY: rRNA
(B) LOCATION: 980..1107
(D) OTHER INFORMATION: /note= "Region B - The 3' End of Domain I in the 23S rRNA"

(xi) SEQUENCE DESCRIPTION: SEQ ID NO:32:

```
CATGAAGTCG GAATTGCTAG TAATGGCGTG TCAGCCATAA CGCCGTGAAT ACGTTCCCGG     60
```

-continued

```
GCCTTGTACA CACCGCCCGT CACATCATGG GAGTTGGTTT TACCTTAAGT CGTTGACTCA    120

ACCCGCAAGG GAGAGAGGCG CCCAAGGTGA GGCTGATGAC TAGGATGAAG TCGTAACAAG    180

GTAGCCCTAC CGGAAGGTGG GGCTGGATCA CCTCCTTTTA AGGATAAGGA AGAAGCCTGA    240

GAGGGTTTCT GACTAGGTTG GGCAAGCGTT TATATGTAAG AGCAAGCATT CTATTTCATT    300

TGTGTTGTTA AGAGTAGCGC GGTGAGGACG AGACATATAG TTTGTGATCA AGTATGTTAT    360

TGTAAAGAAA TAATCATGGT AACAAGTATA TTTCACGCAT AATAATAGAC GTTTAAGAGT    420

ATTTGTCTTT TAGGTGAAGT GCTTGCATGG ATCTATAGAA ATTACAGACC AAGTTAATAA    480

GAGCTATTGG TGGATGCCTT GGCATTGACA GGCGAAGAAG GACGCAAATA CCTGCGAAAA    540

GCTCCGGCGA GCTGGTGATA AGCAAAGACC CGGAGGTATC CGAATGGGGA AACCCGGTAG    600

AGTAATAGAC TACCATTGCA TGCTGAATAC ATAGGTATGC AAAGCGACAC CTGCCGAACT    660

GAAACATCTT AGTAAGCAGA GGAAAAGAAA TCGAAGAGAT TCCCTGTGTA GCGGCGAGCG    720

AAAGGGGAAT AGCCTAAACC GAGCTGATAA GGCTCGGGGT TGTAGGATTG AGGATAAAGG    780

ATCAGGACTC CTAGTTGAAC ACATCTGGAA AGATGGATGA TACAGGGTGA TAGTCCCGTA    840

GACGAAAGGA GAGAAAGACC GACCTCAACA CCTGAGTAGG ACTAGACACG TGAAACCTAG    900

TCTGAATCTG GGGAGACCAC TCTCCAAGGC TAAATACTAG TCAATGACCG ATAGTGAACC    960

AGTACTGTGA AGGAAAGGCG AAAAGAACCC TTGTTAAGGG AGTGAAATAG AACCTGAAAC   1020

CAGTAGCTTA CAAGCGGTCG GAGACCAATG GCCCGTAAGG GTCAAGGTTG ACGGCGTGCC   1080

TTTTGCATGA TGAGCCAGGG AGTTAAGCTA AACGGCGAGG TTAAGGGATA TACATTCCGG   1140

AGCCGGAGCG AAAGCGAGTT TTAAAAGAGC GAAGAGTCGT TTGGTTTAGA CACGAAACCA   1200

AGTGAGCTAT TTATGACCAG GTTGAAGCAT GGGTAAAACT ATGTGGAGGA CCGAACTAGT   1260

ACCTGTTGAA AAAGGTTTGG ATGAGTTGTG AATAGGGGTG AAAG                     1304
```

(2) INFORMATION FOR SEQ ID NO:33:

(i) SEQUENCE CHARACTERISTICS:
(A) LENGTH: 1304 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia trachomatis
(B) STRAIN: B/TW-5/OT (ix) FEATURE:
(A) NAME/KEY: rRNA
(B) LOCATION: 1..219
(D) OTHER INFORMATION: /note= “16S rRNA”

(ix) FEATURE:
(A) NAME/KEY: misc_RNA
(B) LOCATION: 220..462
(D) OTHER INFORMATION: /note= “intergenic spacer”

(ix) FEATURE:
(A) NAME/KEY: rRNA
(B) LOCATION: 463..1084
(D) OTHER INFORMATION: /note= “Domain I of the 23S rRNA”

(ix) FEATURE:
(A) NAME/KEY: rRNA

-continued (B) LOCATION: 463..1304
(D) OTHER INFORMATION: /note= "23S rRNA"

(ix) FEATURE:
(A) NAME/KEY: misc_RNA
(B) LOCATION: 1..555
(D) OTHER INFORMATION: /note= "Region A - Region of the Intergenic Spacer"

(ix) FEATURE:
(A) NAME/KEY: rRNA
(B) LOCATION: 980..1107
(D) OTHER INFORMATION: /note= "Region B - the 3' End of Domain I in the 23S rRNA"

(xi) SEQUENCE DESCRIPTION: SEQ ID NO:33:

```
CATGAAGTCG GAATTGCTAG TAATGGCGTG TCAGCCATAA CGCCGTGAAT ACGTTCCCGG     60
GCCTTGTACA CACCGCCCGT CACATCATGG GAGTTGGTTT TACCTTAAGT CGTTGACTCA    120
ACCCGCAAGG GAGAGAGGCG CCCAAGGTGA GGCTGATGAC TAGGATGAAG TCGTAACAAG    180
GTAGCCCTAC CGGAAGGTGG GGCTGGATCA CCTCCTTTTA AGGATAAGGA AGAAGCCTGA    240
GAGGGTTTCT GACTAGGTTG GGCAAGCGTT TATATGTAAG AGCAAGCATT CTATTTCATT    300
TGTGTTGTTA AGAGTAGCGC GGTGAGGACG AGACATATAG TTTGTGATCA AGTATGTTAT    360
TGTAAAGAAA TAATCATGGT AACAAGTATA TTTCACGCAT AATAATAGAC GTTTAAGAGT    420
ATTTGTCTTT TAGGTGAAGT GCTTGCATGG ATCTATAGAA ATTACAGACC AAGTTAATAA    480
GAGCTATTGG TGGATGCCTT GGCATTGACA GGCGAAGAAG GACGCGAATA CCTGCGAAAA    540
GCTCCGGCGA GCTGGTGATA AGCAAAGACC CGGAGGTATC CGAATGGGGA AACCCGGTAG    600
AGTAATAGAC TACCATTGCA TGCTGAATAC ATAGGTATGC AAAGCGACAC CTGCCGAACT    660
GAAACATCTT AGTAAGCAGA GGAAAAGAAA TCGAAGAGAT TCCCTGTGTA GCGGCGAGCG    720
AAAGGGGAAT AGCCTAAACC GAGCTGATAA GGCTCGGGGT TGTAGGATTG AGGATAAAGG    780
ATCAGGACTC CTAGTTGAAC ACATCTGGAA AGATGGATGA TACAGGGTGA TAGTCCCGTA    840
GACGAAAGGA GAGAAAGACC GACCTCAACA CCTGAGTAGG ACTAGACACG TGAAATCTAG    900
TCTGAATCTG GGGAGACCAC TCTCCAAGGC TAAATACTAG TCAATGACCG ATAGTGAACC    960
AGTACTGTGA AGGAAAGGCG AAAAGAACCC TTGTTAAGGG AGTGAAATAG AACCTGAAAC   1020
CAGTAGCTTA CAAGCGGTCG GAGACCAATG GCCCGTAAGG GTCAAGGTTG ACGGCGTGCC   1080
TTTTGCATGA TGAGCCAGGG AGTTAAGCTA AACGGCGAGG TTAAGGGATA TACATTCCGG   1140
AGCCGGAGCG AAAGCGAGTT TTAAAAGAGC GAAGAGTCGT TTGGTTTAGA CACGAAACCA   1200
AGTGAGCTAT TTATGACCAG GTTGAAGCAT GGGTAAAACT ATGTGGAGGA CCGAACTAGT   1260
ACCTGTTGAA AAAGGTTTGG ATGAGTTGTG AATAGGGGTG AAAG                     1304
```

(2) INFORMATION FOR SEQ ID NO:34:

(i) SEQUENCE CHARACTERISTICS:
(A) LENGTH: 1304 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia trachomatis
(B) STRAIN: D/UW-3/CX -continued (ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..462
(D) OTHER INFORMATION: /note= "intergenic spacer"

(ix) FEATURE:
(A) NAME/KEY: rRNA
(B) LOCATION: 463..1084
(D) OTHER INFORMATION: /note= "Domain I of the 23S rRNA"

(ix) FEATURE:
(A) NAME/KEY: rRNA
(B) LOCATION: 463..1304
(D) OTHER INFORMATION: /note= "23S rRNA"

(ix) FEATURE:
(A) NAME/KEY: misc_RNA
(B) LOCATION: 1..555
(D) OTHER INFORMATION: /note= "Region A - Region of the Intergenic Spacer"

(ix) FEATURE:
(A) NAME/KEY: rRNA
(B) LOCATION: 980..1107
(D) OTHER INFORMATION: /note= "Region B - The 3' End of Domain I in the 23S rRNA"

(xi) SEQUENCE DESCRIPTION: SEQ ID NO:34:

CATGAAGTCG GAATTGCTAG TAATGGCGTG TCAGCCATAA CGCCGTGAAT ACGTTCCCGG 60

GCCTTGTACA CACCGCCCGT CACATCATGG GAGTTGGTTT TACCTTAAGT CGTTGACTCA 120

ACCCGCAAGG GAGAGAGGCG CCCAAGGTGA GGCTGATGAC TAGGATGAAG TCGTAACAAG 180

GTAGCCCTAC CGGAAGGTGG GGCTGGATCA CCTCCTTTTA AGGATAAGGA AGAAGCCTGA 240

GAAGGTTTCT GACTAGGTTG GGCAAGCGTT TATATGTAAG AGCAAGCATT CTATTTCATT 300

TGTGTTGTTA AGAGTAGCGC GGTGAGGACG AGACATATAG TTTGTGATCA AGTATGTTAT 360

TGTAAAGAAA TAATCATGGT AACAAGTATA TTTCACGCAT AATAATAGAC GTTTAAGAGT 420

ATTTGTCTTT TAGGTGAAGT GCTTGCATGG ATCTATAGAA ATTACAGACC AAGTTAATAA 480

GAGCTATTGG TGGATGCCTT GGCATTGACA GGCGAAGAAG GACGCGAATA CCTGCGAAAA 540

GCTCCGGCGA GCTGGTGATA AGCAAAGACC CGGAGGTATC CGAATGGGGA AACCCGGTAG 600

AGTAATAGAC TACCATTGCA TGCTGAATAC ATAGGTATGC AAAGCGACAC CTGCCGAACT 660

GAAACATCTT AGTAAGCAGA GGAAAAGAAA TCGAAGAGAT TCCCTGTGTA GCGGCGAGCG 720

AAAGGGGAAT AGCCTAAACC GAGCTGATAA GGCTCGGGGT TGTAGGATTG AGGATAAAGG 780

ATCAGGACTC CTAGTTGAAC ACATCTGGAA AGATGGATGA TACAGGGTGA TAGTCCCGTA 840

GACGAAAGGA GAGAAAGACC GACCTCAACA CCTGAGTAGG ACTAGACACG TGAAACCTAG 900

TCTGAATCTG GGGAGACCAC TCTCCAAGGC TAAATACTAG TCAATGACCG ATAGTGAACC 960

AGTACTGTGA AGGAAAGGCG AAAAGAACCC TTGTTAAGGG AGTGAAATAG AACCTGAAAC 1020

CAGTAGCTTA CAAGCGGTCG GAGACCAATG GCCCGTAAGG GTCAAGGTTG ACGGCGTGCC 1080

TTTTGCATGA TGAGCCAGGG AGTTAAGCTA AACGGCGAGG TTAAGGGATA TACATTCCGG 1140

AGCCGGAGCG AAAGCGAGTT TTAAAAGAGC GAAGAGTCGT TTGGTTTAGA CACGAAACCA 1200

AGTGAGCTAT TTATGACCAG GTTGAAGCAT GGGTAAAACT ATGTGGAGGA CCGAACTAGT 1260

ACCTGTTGAA AAAGGTTTGG ATGAGTTGTG AATAGGGGTG AAAG 1304

(2) INFORMATION FOR SEQ ID NO:35:

(i) SEQUENCE CHARACTERISTICS:
        (A) LENGTH: 1304 base pairs
        (B) TYPE: nucleic acid
        (C) STRANDEDNESS: single
        (D) TOPOLOGY: linear (ii) MOLECULE TYPE: rRNA (iii) HYPOTHETICAL: NO (iv) ANTI-SENSE: NO (vi) ORIGINAL SOURCE:
        (A) ORGANISM: Chlamydia trachomatis
        (B) STRAIN: F/IC/CAL3

(ix) FEATURE:
        (A) NAME/KEY: rRNA
        (B) LOCATION: 1..219
        (D) OTHER INFORMATION: /note= "16S rRNA"

(ix) FEATURE:
        (A) NAME/KEY: misc_RNA
        (B) LOCATION: 220..462
        (D) OTHER INFORMATION: /note= "intergenic spacer"

(ix) FEATURE:
        (A) NAME/KEY: rRNA
        (B) LOCATION: 463..1084
        (D) OTHER INFORMATION: /note= "Domain I of the 23S rRNA"

(ix) FEATURE:
        (A) NAME/KEY: rRNA
        (B) LOCATION: 463..1304
        (D) OTHER INFORMATION: /note= "23S rRNA"

(ix) FEATURE:
        (A) NAME/KEY: misc_RNA
        (B) LOCATION: 1..555
        (D) OTHER INFORMATION: /note= "Region A - Region of the
            Intergenic Spacer"

(ix) FEATURE:
        (A) NAME/KEY: rRNA
        (B) LOCATION: 980..1107
        (D) OTHER INFORMATION: /note= "Region B - The 3' End of
            Domain I in the 23S rRNA"

(xi) SEQUENCE DESCRIPTION: SEQ ID NO:35:

```
CATGAAGTCG GAATTGCTAG TAATGGCGTG TCAGCCATAA CGCCGTGAAT ACGTTCCCGG    60

GCCTTGTACA CACCGCCCGT CACATCATGG GAGTTGGTTT TACCTTAAGT CGTTGACTCA   120

ACCCGCAAGG GAGAGAGGCG CCCAAGGTGA GGCTGATGAC TAGGATGAAG TCGTAACAAG   180

GTAGCCCTAC CGGAAGGTGG GGCTGGATCA CCTCCTTTTA AGGATAAGGA AGAAGCCTGA   240

GAAGGTTTCT GACTAGGTTG GGCAAGCATT TATATGTAAG AGCAAGCATT CTATTTCATT   300

TGTGTTGTTA AGAGTAGCGC GGTGAGGACG AGACATATAG TTTGTGATCA AGTATGTTAT   360

TGTAAAGAAA TAATCATGGT AACAAGTATA TTTCACGCAT AATAATAGAC GTTTAAGAGT   420

ATTTGTCTTT TAGGTGAAGT GCTTGCATGG ATCTATAGAA ATTACAGACC AAGTTAATAA   480

GAGCTATTGG TGGATGCCTT GGCATTGACA GGCGAAGAAG GACGCGAATA CCTGCGAAAA   540

GCTCCGGCGA GCTGGTGATA AGCAAAGACC CGGAGGTATC CGAATGGGGA AACCCGGTAG   600

AGTAATAGAC TACCATTGCA TGCTGAATAC ATAGGTATGC AAAGCGACAC CTGCCGAACT   660

GAAACATCTT AGTAAGCAGA GGAAAAGAAA TCGAAGAGAT TCCCTGTGTA GCGGCGAGCG   720

AAAGGGGAAT AGCCTAAACC GAGCTGATAA GTCTCGGGGT TGTAGGATTG GGGATAAAGG   780
```

-continued

```
ATCAGAACTC CTAGTTGAAC ACATCTGGAA AGATGGATGA TACAGGGTGA TAGTCCCGTA    840

GACGAAAGGA GAGAAAGACC GACCTCAACA CCTGAGTAGG ACTAGACACG TGAAACCTAG    900

TCTGAATCTG GGGAGACCAC TCTCCAAGGC TAAATACTAG TCAATGACCG ATAGTGAACC    960

AGTACTGTGA AGGAAAGGCG AAAAGAACCC TTGTTAAGGG AGTGAAATAG AACCTGAAAC   1020

CAGTAGCTTA CAAGCGGTCG GAGACCAATG GCCCGTAAGG GTCAAGGTTG ACGGCGTGCC   1080

TTTTGCATGA TGAGCCAGGG AGTTAAGCTA AACGGCGAGG TTAAGGGATA TACATTCCGG   1140

AGCCGGAGCG AAAGCGAGTT TTAAAAGAGC GAAGAGTCGT TTGGTTTAGA CACGAAACCA   1200

AGTGAGCTAT TTATGACCAG GTTGAAGCAT GGGTAAAACT ATGTGGAGGA CCGAACTAGT   1260

ACCTGTTGAA AAAGGTTTGG ATGAGTTGTG AATAGGGGTG AAAG                    1304
```

(2) INFORMATION FOR SEQ ID NO:36:

(i) SEQUENCE CHARACTERISTICS:
(A) LENGTH: 1304 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia trachomatis
(B) STRAIN: L2/434/BU (ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..462
(D) OTHER INFORMATION: /note= "intergenic spacer"

(ix) FEATURE:
(A) NAME/KEY: rRNA
(B) LOCATION: 463..1084
(D) OTHER INFORMATION: /note= "Domain I of the 23S ribosomal RNA"

(ix) FEATURE:
(A) NAME/KEY: rRNA
(B) LOCATION: 463..1304
(D) OTHER INFORMATION: /note= "23S rRNA"

(ix) FEATURE:
(A) NAME/KEY: misc_RNA
(B) LOCATION: 1..555
(D) OTHER INFORMATION: /note= "Region A - Region of the Intergenic Spacer"

(ix) FEATURE:
(A) NAME/KEY: rRNA
(B) LOCATION: 980..1107
(D) OTHER INFORMATION: /note= "Region B - The 3' End of Domain I in the 23S rRNA"

(xi) SEQUENCE DESCRIPTION: SEQ ID NO:36:

```
CATGAAGTCG GAATTGCTAG TAATGGCGTG TCAGCCATAA CGCCGTGAAT ACGTTCCCGG     60

GCCTTGTACA CACCGCCCGT CACATCATGG GAGTTGGTTT TACCTTAAGT CGTTGACTCA    120

ACCCGCAAGG GAGAGAGGCG CCCAAGGTGA GGCTGATGAC TAGGATGAAG TCGTAACAAG    180

GTAGCCCTAC CGGAAGGTGG GGCTGGATCA CCTCCTTTTA AGGATAAGGA AGAAGCCTGA    240
```

-continued

```
GAAGGTTTCT GACTAGGTTG GGCAAGCATT TATATGTAAG AGCAAGCATT CTATTTCATT    300

TGTGTTGTTA AGAGTAGCGT GGTGAGGACG AGACATATAG TTTGTGATCA AGTATGTTAT    360

TGTAAAGAAA TAATCATGGT AACAAGTATA TTTCACGCAT AATAATAGAC GTTTAAGAGT    420

ATTTGTCTTT TAGGTGAAGT GCTTGCATGG ATCTATAGAA ATTACAGACC AAGTTAATAA    480

GAGCTATTGG TGGATGCCTT GGCATTGACA GGCGAAGAAG GACGCGAATA CCTGCGAAAA    540

GCTCCGGCGA GCTGGTGATA AGCAAAGACC CGGAGGTATC CGAATGGGGA AACCCGGTAG    600

AGTAATAGAC TACCATTGCA TGCTGAATAC ATAGGTATGC AAAGCGACAC CTGCCGAACT    660

GAAACATCTT AGTAAGCAGA GGAAAAGAAA TCGAAGAGAT TCCCTGTGTA GCGGCGAGCG    720

AAAGGGGAAT AGCCTAAACC GAGCTGATAA GGCTCGGGGT TGTAGGATTG AGGATAAAGG    780

ATCAGGACTC CTAGTTGAAC ACATCTGGAA AGATGGATGA TACAGGGTGA TAGTCCCGTA    840

GACGAAAGGA GAGAAAGACC GACCTCAACA CCTGAGTAGG ACTAGACACG TGAAACCTAG    900

TCTGAATCTG GGGAGACCAC TCTCCAAGGC TAAATACTAG TCAATGACCG ATAGTGAACC    960

AGTACTGTGA AGGAAAGGCG AAAAGAACCC TTGTTAAGGG AGTGAAATAG AACCTGAAAC   1020

CAGTAGCTTA CAAGCGGTCG GAGACCAATG GCCCGTAAGG GTCAAGGTTG ACGGCGTGCC   1080

TTTTGCATGA TGAGCCAGGG AGTTAAGCTA AACGGCGAGG TTAAGGGATA TACATTCCGG   1140

AGCCGGAGCG AAAGCGAGTT TTAAAAGAGC GAAGAGTCGT TTGGTTTAGA CACGAAACCA   1200

AGTGAGCTAT TTATGACCAG GTTGAAGCAT GGGTAAAACT ATGTGGAGGA CCGAACTAGT   1260

ACCTGTTGAA AAAGGTTTGG ATGAGTTGTG AATAGGGGTG AAAG                    1304
```

(2) INFORMATION FOR SEQ ID NO:37:

(i) SEQUENCE CHARACTERISTICS:
(A) LENGTH: 2762 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia trachomatis
(B) STRAIN: R22

(ix) FEATURE:
(A) NAME/KEY: rRNA
(B) LOCATION: 1..564
(D) OTHER INFORMATION: /note= "16S rRNA"

(ix) FEATURE:
(A) NAME/KEY: misc_RNA
(B) LOCATION: 565..802
(D) OTHER INFORMATION: /note= "intergenic spacer"

(ix) FEATURE:
(A) NAME/KEY: rRNA
(B) LOCATION: 803..1424
(D) OTHER INFORMATION: /note= "Domain I of the 23S rRNA"

(ix) FEATURE:
(A) NAME/KEY: rRNA
(B) LOCATION: 803..2762
(D) OTHER INFORMATION: /note= "23S rRNA"

(ix) FEATURE:
(A) NAME/KEY: misc_RNA
(B) LOCATION: 346..895

-continued (D) OTHER INFORMATION: /note= "Region A - Region of the Intergenic Spacer"

(ix) FEATURE:
(A) NAME/KEY: rRNA
(B) LOCATION: 1320..1447
(D) OTHER INFORMATION: /note= "Region B - The 3' End of Domain I in the 23S rRNA"

(xi) SEQUENCE DESCRIPTION: SEQ ID NO:37:

TTACCTGGGT TTGACATGCA TATGACCGCG GCAGAAATGT CGTTTTCCGC AAGGACATAT 60

GCACAGGTGC TGCATGGCTG TCGTCAGCTC GTGCCGTGAG GTGTTGGGTT AAGTCCCGCA 120

ACGAGCGCAA CCCTTATCGT TAGTTGCCAG CACTTAGGGT GGGAACTCTA ACGAGACTGC 180

CTGGGTTAAC CAGGAGGAAG GCGAGGATGA CGTCAAGTCA GCATGGCCCT TATGCCCAGG 240

GCGACACACG TGCTACAATG GCCAGTACAG AAGGTAGCAA GATCGTGAGA TGGAGCAAAT 300

CCTTAAAGCT GGCCCCAGTT CGGATTGTAG TCTGCAACTC GACTACATGA AGTCGGAATT 360

GCTAGTAATG GCGTGTCAGC CATAACGCCG TGAATACGTT CCCGGGCCTT GTACACACCG 420

CCCGTCACAT CATGGGAGTT GGTTTTACCT TAAGTCGTTG ACTCAACCCG CAAGGGAGAG 480

AGGCGCCCAA GGTGAGGCTG ATGACTAGGA TGAAGTCGTA ACAAGGTAGC CCTACCGGAA 540

GGTGGGGCTG GATCACCTCC TTTTAAGGAT AAGGAAGAAG CCTGAAAAGG TTTCTGACTA 600

GGTTGGGCAA GCATTTATAC GTAAGGGCGA GCATTCTATT TCATTTGCAT TGTTAAGGTA 660

GCTGAAGAGG ACGAGACATA TAGTTTATGA TCAAGTATGT TATGTAAAGA AAATCATGGT 720

AACAAGTATA TTTCACGCAT AATAATAGAC GTTTAAGAGT ATTTGTCTTT AGGTGAAGTA 780

CTTGCATGGA TCTATGAGAA ATTACAGACC AAGTTGATAA GAGCTATTGG TGGATGCCTT 840

GGCATTGACA GGCGAAGAAG GACGCGAATA CCTGCGAAAA GCTCCGGCGA GCTGGTGATA 900

AGCAACGACC CGGAGGTATC CGAATGGGGA AACCCGGTAG AGTAATAGTC TACCATTGTA 960

TACTGAACAC ATAGGTATAC AAAGCGACAC CTGCCGAACT GAAACATCTT AGTAAGCAGA 1020

GGAAAAGAAA TCGAAGAGAT TCTCTGTGTA GCGGCGAGCG AAAGGGGAAG AGCCTAAACC 1080

GAGCTGAAGA AGCGAGGGGT TGTAGGGTTG AGGAAAAAGG ATCAGGACTC CTAGTTGAAC 1140

ACATCTGGAA AGGTGGATGA TACAGGGTGA TAGTCCCGTA GACGAAAGGA GAGAAAGACT 1200

GACCTCAATA CCTGAGTAGG ACTAGACACG TGAAACCTAG TCTGAATCTG GGGAGACCAC 1260

TCTCCAAGGC TAAATACTAG TCAATGACCG ATAGTGAACC AGTACTGTGA AGGAAAGGCG 1320

AAAAGAACCC TTGTTAAGGG AGTGAAATAG AACCTGAAAC CAATAGCTTA CAAGCGGTCG 1380

GAGACCTATG GCCCGTAAGG GTTAAGGTTG ACGGCGTGCC TTTTGCATGA TGAGCCAGGG 1440

AGTTAAGCTA AACGGCGAGG TTAAGGGATG TACATTCCGG AGCCGAAGCG AAAGCGAGTT 1500

TTAAAAGAGC GTTTAGTCGT TTGGTTTAGA CACGAAACCA AGTGAGCTAT TTATGACCAG 1560

GTTGAAGCAT GGGTAAAACT ATGTGGAGGA CCGAACTAGT ACCTGTTGAA AAAGGTTTGG 1620

ATGAGTTGTG AATAGGGGTG AAAGGCCAAT CAAACTTGGA GATATCTTGT TCTCTCCGAA 1680

ATAACTATAG GGTTAGCCTC GGATAATAAG CTTTTGGGGG TAGAGCACTG AATTCTAGCG 1740

GGGGCCTACC GGCTTACCAA CGGAAATCAA ACTCCGAATA CCAGAAGCGA GTCCGGGAGA 1800

TAGACAGCGG GGGCTAAGCT TCGTTGTCGA GAGGGGAGCA GCCCAGACCG CCGATTAAGG 1860

TCCCTAATTT TATGCTAAGT GAGTAAGGAA GTGATGATTC AAAGACAGTT GGAATGTTGG 1920

CTTAGAGGCA GCAATCATTT AAAGAGTGCG TAACAGCTCA CCAATCGAGA ATCATTGCGC 1980

CGATAATAAA CGGGGCTAAG CATAAAACCG ACATCGCGGG TGTGTCGTAA GGCACGCGGT 2040

-continued

```
AGGAGAGCGT AGTATTCAGC AGAGAAGGTG TACCGAAAGG AGCGCTGGAG CGGATACTAG   2100

TGAAGATCCA TGGCATAAGT AACGATAAAG GGAGTGAAAA TCTCCCTCGC CGTAAGCCCA   2160

AGGTTTCCAG GGTCAAGCTC GTCTTCCCTG GGTTAGTCGG CCCCTAAGTT GAGGCGTAAC   2220

TGCGTAGACG ATGGAGCAGC AGGTTAAATA TTCCTGCACC ACCTAAGACT ATAGCGAAGG   2280

AATGACGGAG TAAGTTAAGC ACGCGGACGA TTGGAAGTGT CCGTAGAGCG ATGAGAACGG   2340

TTAGTAGGCA AATCCGCTAA CAGAAGATCA GGTCGCGATC AAGGGGAATC TTCGGAGGAA   2400

CCGATGGTGT GTAGCGAGGC TTTCAAGAAA TAATTTCTAG CTGTTGATGG TGACCGTACC   2460

AAAACCGACA CAGGTGGGCG AGATGAGTAT TCTAAGGCGC GCGAGATAAC TTTCGTTAAG   2520

GAACTCGGCA AATTATCCCC GTAACTTCGG GATAAGGGGA GCCTTTTAGG GTGACTATGG   2580

AACGATAGGA GCCCCGGGGG GCCGCAGAGA AATGGCCCAG GCGACTGTTT AGCAAAAACA   2640

CAGCACTATG CAAACCTCGA AGGGGAAGTA TATGGTGTGA CGCCTGCCCA ATGCCAAAAG   2700

GTTAAAGGGA TATGTCAGCT GCAAAGCGAA GCATTGAACC TAAGCCCTGG TGAATGGCCG   2760

CC                                                                  2762
```

(2) INFORMATION FOR SEQ ID NO:38:

(i) SEQUENCE CHARACTERISTICS:
(A) LENGTH: 1299 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia trachomatis
(B) STRAIN: R24

(ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..457
(D) OTHER INFORMATION: /note= "intergenic spacer"

(ix) FEATURE:
(A) NAME/KEY: rRNA
(B) LOCATION: 458..1079
(D) OTHER INFORMATION: /note= "Domain I of the 23S rRNA"

(ix) FEATURE:
(A) NAME/KEY: rRNA
(B) LOCATION: 458..1299
(D) OTHER INFORMATION: /note= "23S rRNA"

(ix) FEATURE:
(A) NAME/KEY: misc_RNA
(B) LOCATION: 1..550
(D) OTHER INFORMATION: /note= "Region A - Region of the Intergenic Spacer"

(ix) FEATURE:
(A) NAME/KEY: rRNA
(B) LOCATION: 975..1102
(D) OTHER INFORMATION: /note= "Region B - The 3' End of Domain I in the 23S rRNA"

(xi) SEQUENCE DESCRIPTION: SEQ ID NO:38:

-continued

```
CATGAAGTCG GAATTGCTAG TAATGGCGTG TCAGCCATAA CGCCGTGAAT ACGTTCCCGG     60

GCCTTGTACA CACCGCCCGT CACATCATGG GAGTTGGTTT TACCTTAAGT CGTTGACTCA    120

ACCCGCAAGG GAGAGAGGCG CCCAAGGTGA GGCTGATGAC TAGGATGAAG TCGTAACAAG    180

GTAGCCCTAC CGGAAGGTGG GGCTGGATCA CCTCCTTTTA AGGATAAGGA AGAAGCCTGA    240

AAAGGTTTCT GACTAGGTTG GGCAAGCATT TATACGTAAG AGCAAGCATT CTATTTCATT    300

TGCATTGTTA AGGTAGCTGA AGAGGACGAG ACATATAGTT TATGATCAAG TATGTTATGT    360

AAAGAAAATC ATGGTAACAA GTATATTTCA CGCATAATAA TAGACGTTTA AGAGTATTTG    420

TCTTTAGGTG AAGTACTTGC ATGGATCTAT GAGAAATTAC AGACCAAGTT GATAAGAGCT    480

ATTGGTGGAT GCCTTGGCAT TGACAGGCGA AGAAGGACGC GAATACCTGC GAAAAGCTCC    540

GGCGAGCTGG TGATAAGCAA CGACCCGGAG GTATCCGAAT GGGGAAACCC GGTAGAGTAA    600

TAGTCTACCA TTGTATACTG AACACATAGG TATACAAAGC GACACCTGCC GAACTGAAAC    660

ATCTTAGTAA GCAGAGGAAA AGAAATCGAA GAGATTCCCT GTGTAGCGGC GAGCGAAAGG    720

GGAAGAGCCT AAACCGAGCT GAAGAAGCGA GGGGTTGTAG GGTTGAGGAA AAAGGATCAG    780

GACTCCTAGT TGAACACATC TGGAAAGGTG GATGATACAG GGTGATAGTC CCGTAGACGA    840

AAGGAGAGAA AGACCGACCT CAATACCTGA GTAGGACTAG ACACGTGAAA CCTAGTCTGA    900

ATCTGGGGAG ACCACTCTCC AAGGCTAAAT ACTAGTCAAT GACCGATAGT GAACCAGTAC    960

TGTGAAGGAA AGGCGAAAAG AACCCTTGTT AAGGGAGTGA AATAGAACCT GAAACCAATA   1020

GCTTACAAGC GGTCGGAGAC CTATGGCCCG TAAGGGTTAA GGTTGACGGC GTGCCTTTTG   1080

CATGATGAGC CAGGGAGTTA AGCTAAACGG CGAGGTTAAG GGATGTACAT TCCGGAGCCG   1140

AAGCGAAAGC GAGTTTTAAA AGAGCGTTTA GTCGTTTGGT TTAGACACGA AACCAAGTGA   1200

GCTATTTATG ACCAGGTTGA AGCATGGGTA AAACTATGTG GAGGACCGAA CTAGTACCTG   1260

TTGAAAAAGG TTTGGATGAG TTGTGAATAG GGGTGAAAG                          1299
```

(2) INFORMATION FOR SEQ ID NO:39:

(i) SEQUENCE CHARACTERISTICS:
(A) LENGTH: 1298 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia trachomatis
(B) STRAIN: R27

(ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..457
(D) OTHER INFORMATION: /note= "intergenic spacer"

(ix) FEATURE:
(A) NAME/KEY: rRNA
(B) LOCATION: 458..1079
(D) OTHER INFORMATION: /note= "Domain I of the 23S rRNA"

(ix) FEATURE:

-continued (A) NAME/KEY: rRNA
(B) LOCATION: 458..1298
(D) OTHER INFORMATION: /note= "23S rRNA"

(ix) FEATURE:
(A) NAME/KEY: misc_RNA
(B) LOCATION: 1..550
(D) OTHER INFORMATION: /note= "Region A - Region of the Intergenic Spacer"

(ix) FEATURE:
(A) NAME/KEY: rRNA
(B) LOCATION: 975..1101
(D) OTHER INFORMATION: /note= "Region B - The 3' End of Domain I in the 23S rRNA"

(xi) SEQUENCE DESCRIPTION: SEQ ID NO:39:

```
CATGAAGTCG GAATTGCTAG TAATGGCGTG TCAGCCATAA CGCCGTGAAT ACGTTCCCGG     60

GCCTTGTACA CACCGCCCGT CACATCATGG GAGTTGGTTT TACCTTAAGT CGTTGACTCA    120

ACCCGCAAGG GAGAGAGGCG CCCAAGGTGA GGCTGATGAC TAGGATGAAG TCGTAACAAG    180

GTAGCCCTAC CGGAAGGTGG GGCTGGATCA CCTCCTTTTA AGGATAAGGA AGAAGCCTGA    240

AAAGGTTTCT GACTAGGTTG GCCAAGCATT TATACGTAAG GGCAAGCATT CTATTTCATT    300

TGCATTGTTA AGGTAGCTGA AGAGGACGAG ACATATAGTT TATGATCAAG TATGTTATGT    360

AAAGAAAATC ATGGTAACAA GTATATTTCA CGCATAATAA TAGACGTTTA AGAGTATTTG    420

TCTTTAGGTG AAGTACTTGC ATGGATCTAT GAGAAATTAC AGACCAAGTT GATAAGAGCT    480

ATTGGTGGAT GCCTTGGCAT TGACAGGCGA AGAAGGACGC GAATACCTGC GAAAAGCTCC    540

GGCGAGCTGG TGATAAGCAA CGACCCGGAG GTATCCGAAT GGGGAAACCC GGTAGAGTAA    600

TAGTCTACCA TTGTATACTG AACACATAGG TATACAAAGC GACACCTGCC GAACTGAAAC    660

ATCTTAGTAA GCAGAGGAAA AGAAATCGAA GAGATTCCCT GTGTAGCGGC GAGCGAAAGG    720

GGAAGAGCCT AAACCGAGCT GAAGAAGCGA GGGGTTGTAG GGTTGAGGAA AAAGGATCAG    780

GACTCCTAGT TGAACACATC TGGAAAGGTG GATGATACAG GGTGATAGTC CCGTAGACGA    840

AAGGAGAGAA AGACCGACCT CAATACCTGA GTAGGACTAG ACACGTGAAA CCTAGTCTGA    900

ATCTGGGGAG ACCACTCTCC AAGGCTAAAT ACTAGTCAAT GACCGATAGT GAACCAGTAC    960

TGTGAAGGAA AGGCGAAAAG AACCCTTGTT AAGGGAGTGA AATAGAACCT GAAACCAATA   1020

GCTTACAAGC GGTCGGAGAC CTATGGCCCG TAAGGGTTAA GGTTGACGGC GTGCCTTTTG   1080

CATGATGAGC CAGGAGTTAA GCTAAACGGC GAGGTTAAGG GATGTACATT CCGGAGCCGA   1140

AGCGAAAGCG AGTTTTAAAA GAGCGTTTAG TCGTTTGGTT TAGACACGAA ACCAAGTGAG   1200

CTATTTATGA CCAGGTTGAA GCATGGGTAA AACTATGTGG AGGACCGAAC TAGTACCTGT   1260

TGAAAAAGGT TTGGATGAGT TGTGAATAGG GGTGAAAG                           1298
```

(2) INFORMATION FOR SEQ ID NO:40:

(i) SEQUENCE CHARACTERISTICS:
(A) LENGTH: 1299 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia trachomatis -continued (B) STRAIN: H5

(ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..457
(D) OTHER INFORMATION: /note= "intergenic spacer"

(ix) FEATURE:
(A) NAME/KEY: rRNA
(B) LOCATION: 458..1079
(D) OTHER INFORMATION: /note= "Domain I of the 23S rRNA"

(ix) FEATURE:
(A) NAME/KEY: rRNA
(B) LOCATION: 458..1299
(D) OTHER INFORMATION: /note= "23S rRNA"

(ix) FEATURE:
(A) NAME/KEY: misc_RNA
(B) LOCATION: 1..550
(D) OTHER INFORMATION: /note= "Region A - Region of the Intergenic Spacer"

(ix) FEATURE:
(A) NAME/KEY: rRNA
(B) LOCATION: 975..1102
(D) OTHER INFORMATION: /note= "Region B - The 3' End of Domain I in the 23S rRNA"

(xi) SEQUENCE DESCRIPTION: SEQ ID NO:40:

```
CATGAAGTCG GAATTGCTAG TAATGGCGTG TCAGCCATAA CGCCGTGAAT ACGTTCCCGG     60

GCCTTGTACA CACCGCCCGT CACATCATGG GAGTTGGTTT TACCTTAAGT CGTTGACTCA    120

ACCCGCAAGG GAGAGAGGCG CCCAAGGTGA GGCTGATGAC TAGGATGAAG TCGTAACAAG    180

GTAGCCCTAC CGGAAGGTGG GGCTGGATCA CCTCCTTTTA AGGATAAGGA AGAAGCCTGA    240

AAAGGTTTCT GACTAGGTTG GGCAAGCATT TATACGTAAG AGCGAGCATT CTATTTCATT    300

TGCATTGTTA AGGTAGCTGA AGAGGACGAG ACATATAGTT TATGATCAAG TATGTTATGT    360

AAAGAAAATC ATGGTAACAA ATACATTTCA CGCATAATAA TAGACGTTTA AGAGTATTTG    420

TCTTTAGGTG AAGTACTTGC ATGGATCTAT GAGAAATTAC AGACCAAGTT GATAAGAGCT    480

ATTGGTGGAT GCCTTGGCAT TGACAGGCGA AGAAGGACGC GAATACCTGC GAAAAGCTCC    540

GGCGAGCTGG TGATAAGCAA CGACCCGGAG GTATCCGAAT GGGGAAACCC GGTAGAGTAA    600

TAGTCTACCA TTGTATACTG AACACATAGG TATACAAAGC GACACCTGCC GAACTGAAAC    660

ATCTTAGTAA GCAGAGGAAA AGAAATCGAA GAGATTCCCT GTGTAGCGGC GAGCGAAAGG    720

GGAAGAGCCT AAACCGAGCC GAAGAAGCGA GGGGTTGTAG GGTTGAGGAA AAAGGATCAG    780

GACTCCTAGT TGAACACATC TGGAAAGGTG GATGATACAG GGTGATAGTC CCGTAGACGA    840

AAGGAGAGAA AGACCGACCT CAATACCTGA GTAGGACTAG ACACGTGAAA CCTAGTCTGA    900

ATCTGGGGAG ACCACTCTCC AAGGCTAAAT ACTAGTCAAT GACCGATAGT GAACCAGTAC    960

TGTGAAGGAA AGGCGAAAAG AACCCTTGTT AAGGGAGTGA AATAGAACCT GAAACCAGTA   1020

GCTTACAAGC GGTCGGAGAC CTACGGCCCG CAAGGGTTAA GGTTGACGGC GTGCCTTTTG   1080

CATGATGAGC CAGGGAGTTA AGCTAAACGG CGAGGTTAAG GGATGTACAT TCTGGAGCCG   1140

GAGCGAAAGC GAGTTTTAAA AGAGCGTATA GTCGTTTGGT TTAGACACGA AACCAAGTGA   1200

GCTATTTATG ACCAGGTTGA AGCATGGGTA AAACTATGTG GAGGACCGAA CTAGTACCTG   1260

TTGAAAAAGG TTTGGATGAG TTGTGAATAG GGGTGAAAG                          1299
```

(2) INFORMATION FOR SEQ ID NO:41:

(i) SEQUENCE CHARACTERISTICS:
(A) LENGTH: 1302 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia trachomatis
(B) STRAIN: S45

(ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..460
(D) OTHER INFORMATION: /note= "intergenic spacer"

(ix) FEATURE:
(A) NAME/KEY: rRNA
(B) LOCATION: 461..1082
(D) OTHER INFORMATION: /note= "Domain I of the 23S rRNA"

(ix) FEATURE:
(A) NAME/KEY: rRNA
(B) LOCATION: 461..1302
(D) OTHER INFORMATION: /note= "23S rRNA"

(ix) FEATURE:
(A) NAME/KEY: misc_RNA
(B) LOCATION: 1..553
(D) OTHER INFORMATION: /note= "Region A - Region of the Intergenic Spacer"

(ix) FEATURE:
(A) NAME/KEY: rRNA
(B) LOCATION: 978..1105
(D) OTHER INFORMATION: /note= "Region B - The 3' End of Domain I in the 23S rRNA"

(xi) SEQUENCE DESCRIPTION: SEQ ID NO:41:

CATGAAGTCG GAATTGCTAG TAATGGCGTG TCAGCCATAA CGCCGTGAAT ACGTTCCCGG 60

GCCTTGTACA CACCGCCCGT CACATCATGG GAGTTGGTTT TACCTTAAGT CGTTGACTCA 120

ACCCGCGAGG GGGAGAGGCG CCCAAGGTGA GGCTGATGAC TAGGATGAAG TCGTAACAAG 180

GTAGCCCTAC CGGAAGGTGG GGCTGGATCA CCTCCTTTTA AGGATAAGGA AGAAGCCTGA 240

GAAGGTTTCT GACTAGGTTG GGCAAGCGTT TATACGTAAG AGCGGGCATT CTATTTCATT 300

TGCATTGTTA AGGTAGCGGA AGAGGACGAG ACATATAGTT TGTGATCAAG TATGTTATGT 360

AAAGAAAAAA TCATGGTAAC AAGTATAATT CACGCATAAT AATAGACGTT TAAGAGTATT 420

TGTCTTTAGG TGAAGTACTT GCATGGATCT ATGAGAAAAA TACAGACCAA GTTGATAAGA 480

GCTATTGGTG GATGCCTTGG CATTGACAGG CGAAGAAGGA CGCGAATACC TGCGAAAAGC 540

TCCGGCGAGC TGGTGATAAG CAAAGACCCG GAGGTATCCG AATGGGGGAA CCCGGTAGAG 600

TAATAGACTA CCATTGTATG CTGAACACAT AGGCATACAA AGCGACACCT GCCGAACTGA 660

AACATCTTAG TAAGCAGAGG AAAAGAAATC GAAGAGATTC CCTGTGTAGC GGCGAGCGAA 720

AGGGGAAGAG CCTAAACCGA GCTGAAGAAG CGAGGGGTTG TAGGGTTGAG GGAGAAGGAT 780

-continued

CAGGACTCCT AGTTGAACAC ATCTGGAAAG GTGGATGATA CAGGGTGATA GTCCCGTAGA 840

CGAAAGGAGA GATAGACCGA CCTCGATACC TGAGTAGGGC TAGACACGTG AAACCTAGTC 900

TGAATCTGGG GAGACCACTC TCCAAGGCTA AATACTAGTC AATGACCGAT AGTGAACCAG 960

TACTGTGAAG GAAAGGCGAA AAGAACCCTT GTTAAGGGAG TGAAATAGAA CCTGAAACCA 1020

GTAGCTTACA AGCGGTCGGA GACCTATGGC CCGCAAGGGT TAAGGTTGAC GGCGTGCCTT 1080

TTGCATGATG AGCCAGGGAG TTAAGCTAAA CGGCGAGGTT AAGGGATGTA CATTCTGGAG 1140

CCGGAGCGAA AGCGAGTTTT AAAAGAGCGT ATAGTCGTTT GGTTTAGACA CGAAACCAAG 1200

TGAGCTATTT ATGACCAGGT TGAAGCATGG GTAAAACTAT GTGGAGGACC GAACTAGTAC 1260

CTGTTGAAAA AGGTTTGGAT GAGTTGTGAA TAGGGGTGAA AG 1302

(2) INFORMATION FOR SEQ ID NO:42:

(i) SEQUENCE CHARACTERISTICS:
(A) LENGTH: 1303 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia trachomatis
(B) STRAIN: MoPn (VR 123)

(ix) FEATURE:
(A) NAME/KEY: rRNA
(B) LOCATION: 1..219
(D) OTHER INFORMATION: /note= “16S rRNA”

(ix) FEATURE:
(A) NAME/KEY: misc_RNA
(B) LOCATION: 220..460
(D) OTHER INFORMATION: /note= “intergenic spacer”

(ix) FEATURE:
(A) NAME/KEY: rRNA
(B) LOCATION: 461..1083
(D) OTHER INFORMATION: /note= “Domain I of the 23S rRNA”

(ix) FEATURE:
(A) NAME/KEY: rRNA
(B) LOCATION: 461..1303
(D) OTHER INFORMATION: /note= “23S rRNA”

(ix) FEATURE:
(A) NAME/KEY: misc_RNA
(B) LOCATION: 1..553
(D) OTHER INFORMATION: /note= “Region A - Region of the Intergenic Spacer”

(ix) FEATURE:
(A) NAME/KEY: rRNA
(B) LOCATION: 976..1106
(D) OTHER INFORMATION: /note= “Region B - The 3' End of Domain I in the 23S rRNA”

(xi) SEQUENCE DESCRIPTION: SEQ ID NO:42:

CATGAAGTCG GAATTGCTAG TAATGGCGTG TCAGCCATAA CGCCGTGAAT ACGTTCCCGG 60

GCCTTGTACA CACCGCCCGT CACATCATGG GAGTTGGTTT TACCTTAAGT CGTTGACTCA 120

ACCCGCAAGG GGGAGAGGCG CCCAAGGTGA GGCTGATGAC TGGGATGAAG TCGTAACAAG 180

GTAGCCCTAC CGGAAGGTGG GGCTGGATCA CCTCCTTTTA AGGATAAGGA AGAAGCCTGA 240

-continued

```
GAAGGTTTCT TACTAGGTTG AGCAAGCATT TATATGTAAG AGCAGGCATT CTATTTCATT    300

TGCGTTGTTA AGGTGGCGCG AAGAGGACGA AACATACAGT TTGTGATCAA GTATGTTATT    360

GTAAAGAAAT AATCATGGTA ACAAGTATAA TTCACGCATA ATAATAGACG TTTAAGAGTA    420

TTTGTCTTTA GGTGAAGTAC TTGCATGGAT CTATGAAATT TACAGACCAA GTTGATAAGA    480

GCTATTGGTG GATGCCTTGG CATTGACAGG CGATGAAGGA CGCGAATACC TGCGAAAAGC    540

TCCGGCGAGC TGGTAATAAG CAAAGACCCG GAGGTGTCCG AATGGGGAAA CCCGGTAGAG    600

TAATAGTCTA CCATTGTATA CTGAATACAT AGGTATGCAA AGCAACACCT GCTGAACTGA    660

AACATCTTAG TAAGCAGAGG AAAAGAAATC GAAGAGATTC CCTGTGTAGC GGCGAGCGAA    720

AGGGGAAGAG CCTAAACCGA ACTTATAGTT CGGGGTTGTA GGATTGGGGA TAAAGGATCA    780

AGATTCCTAG TTGAACACAT CTGGAAAGGT GGATGAAACA GGGTGATAGT CCCGTAGACG    840

AAAGGAGATC AAGACCGACC TCAACACCTG AGTAGGGCTA GACACGTGAA ACCTAGTCTG    900

AATCTGGGGA GACCACTCTC CAAGGCTAAA TACTAGTCAA TGACCGATAG TGAACCAGTA    960

CTGTGAAGGA AAGGCGAAAA GAACCCTTGT TAAGGGAGTG AAATAGAACC TGAAACCAGT   1020

AGCTTACAAG CGGTCGAAGA CCTATGTCCC TTTAACGGGG TCGAGGTTGA CGGCGTGCCT   1080

TTTGCATGAT GAGCCAGGGA GTTAAGCTAA ACGGCGAGGT TAAGGGATGT ACATTCCGGA   1140

GCCGAAGCGA AAGCGAGTTT TAAAAGAGCG TTTAGTCGTT TGGTTTAGAC ACGAAACCAA   1200

GTGAGCTATT TATGACCAGG TTGAAGCATG GGTAAAACTA TGTGGAGGAC CGAACCAGTA   1260

CCTGTTGAAA AAGGTTTGGA TGAGTTGTGA ATAGGGGTGA AAG                      1303
```

(2) INFORMATION FOR SEQ ID NO:43:

(i) SEQUENCE CHARACTERISTICS:
(A) LENGTH: 1303 base pairs
(B) TYPE: nucleic acid
(C) STRANDEDNESS: single
(D) TOPOLOGY: linear (ii) MOLECULE TYPE: rRNA (iii) HYPOTHETICAL: NO (iv) ANTI-SENSE: NO (vi) ORIGINAL SOURCE:
(A) ORGANISM: Chlamydia trachomatis
(B) STRAIN: SFPD Fox (ix) FEATURE:
(A) NAME/KEY: rRNA
(B) LOCATION: 1..219
(D) OTHER INFORMATION: /note= "16S rRNA"

(ix) FEATURE:
(A) NAME/KEY: misc_RNA
(B) LOCATION: 220..460
(D) OTHER INFORMATION: /note= "intergenic spacer"

(ix) FEATURE:
(A) NAME/KEY: rRNA
(B) LOCATION: 461..1083
(D) OTHER INFORMATION: /note= "Domain I of the 23S rRNA"

(ix) FEATURE:
(A) NAME/KEY: rRNA
(B) LOCATION: 461..1303
(D) OTHER INFORMATION: /note= "23S rRNA"

(ix) FEATURE:
(A) NAME/KEY: misc_RNA
(B) LOCATION: 1..553

-continued (D) OTHER INFORMATION: /note= "Region A - Region of the Intergenic Spacer"

(ix) FEATURE:
(A) NAME/KEY: rRNA
(B) LOCATION: 976..1106
(D) OTHER INFORMATION: /note= "Region B - The 3' End of Domain I in the 23S rRNA"

(xi) SEQUENCE DESCRIPTION: SEQ ID NO:43:

CATGAAGTCG GAATTGCTAG TAATGGCGTG TCAGCCATAA CGCCGTGAAT ACGTTCCCGG 60

GCCTTGTACA CACCGCCCGT CACATCATGG GAGTTGGTTT TACCTTAAGT CGTTGACTCA 120

ACCCGCAAGG GGGANAGGCG CCCAAGGTGA GGCTGATGAC TGGGATGAAG TCGTAACAAG 180

GTAGCCCTAC CGGAAGGTGG GGCTGGATCA CCTCCTTTTA AGGATAAGGA AGAAGCCTGA 240

GAAGGTTTCT TACTAGGTTG AGCAAGCATT TATATGTAAG AGCAGGCATT CTATTTCATT 300

TGCGTTGTTA AGGTGGCGCG AAGAGGACGA AACATACAGT TTGTGATCAA GTATGTTATT 360

GTAAAGAAAT AATCATGGTA ACAAGTATAA TTCACGCATA ATAATAGACG TTTAAGAGTA 420

TTTGTCTTTA GGTGAAGTAC TTGCATGGAT CTATGAAATT TACAGACCAA GTTGATAAGA 480

GCTATTGGTG GATGCCTTGG CATTGACAGG CGATGAAGGA CGCGAATACC TGCGAAAAGC 540

TCCGGCGAGC TGGTAATAAG CAAAGACCCG GAGGTGTCCG AATGGGGAAA CCCGGTAGAG 600

TAATAGTCTA CCATTGTATA CTGAATACAT AGGTATGCAA AGCAACACCT GCTGAACTGA 660

AACATCTTAG TAAGCAGAGG AAAAGAAATC GAAGAGATTC CCTGTGTAGC GGCGAGCGAA 720

AGGGGAAGAG CCTAAACCGA ACTTATAGTT CGGGGTTGTA GGATTGGGGA TAAAGGATCA 780

AGATTCCTAG TTGAACACAT CTGGAAAGGT GGATGAAACA GGGTGATAGT CCCGTAGACG 840

AAAGGAGATC AAGACCGACC TCAACACCTG AGTAGGGCTA GACACGTGAA ACCTAGTCTG 900

AATCTGGGGA GACCACTCTC CAAGGCTAAA TACTAGTCAA TGACCGATAG TGAACCAGTA 960

CTGTGAAGGA AAGGCGAAAA GAACCCTTGT TAAGGGAGTG AAATAGAACC TGAAACCAGT 1020

AGCTTACAAG CGGTCGAAGA CCTATGTCCC TTTAACGGGG TCGAGGTTGA CGGCGTGCCT 1080

TTTGCATGAT GAGCCAGGGA GTTAAGCTAA ACGGCGAGGT TAAGGGATGT ACATTCCGGA 1140

GCCGAAGCGA AAGCGAGTTT TAAAAGAGCG TTTAGTCGTT TGGTTTAGAC ACGAAACCAA 1200

GTGAGCTATT TATGACCAGG TTGAAGCATG GGTAAAACTA TGTGGAGGAC CGAACCAGTA 1260

CCTGTTGAAA AAGGTTTGGA TGAATTGTGA ATAGGGGTGA AAG 1303

(2) INFORMATION FOR SEQ ID NO:44:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiales (xi) SEQUENCE DESCRIPTION: SEQ ID NO:44:

GCATGTGGTT TAATTCGATG CAACGCGAAG AACC 34

(2) INFORMATION FOR SEQ ID NO:45:

(i) SEQUENCE CHARACTERISTICS:

-continued (A) LENGTH: 32 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:45:

GAATTTCGCT ACCTTAGGAC CGTTATAGTT AC 32

(2) INFORMATION FOR SEQ ID NO:46:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:46:

CCGCCCGTCA CATCATGG 18

(2) INFORMATION FOR SEQ ID NO:47:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:47:

TCGTAACAAG GTAGCCC 17

(2) INFORMATION FOR SEQ ID NO:48:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:48:

TACTAAGATG TTTCAGTTC 19

(2) INFORMATION FOR SEQ ID NO:49:

-continued (i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:49:

AAAAGGCACG CCGTCAACC 19

(2) INFORMATION FOR SEQ ID NO:50:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:50:

GATATCTCCA AGTTTGATT 19

(2) INFORMATION FOR SEQ ID NO:51:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:51:

GAGCTGTTAC GCACTCTTT 19

(2) INFORMATION FOR SEQ ID NO:52:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:52:

TACAGACCAA GT 12

(2) INFORMATION FOR SEQ ID NO:53:

-continued (i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:53:

GATGCCTTGG CATTGATAGG CGATGAAGGA 30

(2) INFORMATION FOR SEQ ID NO:54:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:54:

TGGCTCATCA TGCAAAAGGC A 21

(2) INFORMATION FOR SEQ ID NO:55:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:55:

GACTAGGTTG GGCAAG 16

(2) INFORMATION FOR SEQ ID NO:56:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:56:

AGCTCTTADY AACTTGGTCT GTA 23

-continued (2) INFORMATION FOR SEQ ID NO:57:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:57:

ATAATAATAG ACGTTTAAGA 20

(2) INFORMATION FOR SEQ ID NO:58:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:58:

GCCGGAGCTT TTCGCA 16

(2) INFORMATION FOR SEQ ID NO:59:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:59:

GCAGGTAAAC GCATCCTTCA 20

(2) INFORMATION FOR SEQ ID NO:60:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:60:

TGTTAAGGTG GCGCGA 16

-continued (2) INFORMATION FOR SEQ ID NO:61:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:61:

GTTAAGAGTA GCGCGGTGA 19

(2) INFORMATION FOR SEQ ID NO:62:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:62:

CATTTGCATT GTTAAGGTAG C 21

(2) INFORMATION FOR SEQ ID NO:63:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:63:

GGCAAGCATT TGCTGTGTA 19

(2) INFORMATION FOR SEQ ID NO:64:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:64:

GCAAGTATTT TATATTCCGC A 21

-continued (2) INFORMATION FOR SEQ ID NO:65:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:65:

GGGCAAGCAT CTTTGAAAA 19

(2) INFORMATION FOR SEQ ID NO:66:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:66:

CGTTGTTTCC AACACATTTA 20

(2) INFORMATION FOR SEQ ID NO:67:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:67:

AATAGACGTT TAAGAATATA TGTCTTTA 28

(2) INFORMATION FOR SEQ ID NO:68:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:68:

-continued

TTTAAGAATA TCTGTCTTTG GTGA 24

(2) INFORMATION FOR SEQ ID NO:69:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:69:

TTGTTAAGCG TGGGTTACA 19

(2) INFORMATION FOR SEQ ID NO:70:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:70:

TTAAGCGCTC GTTTCCA 17

(2) INFORMATION FOR SEQ ID NO:71:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:71:

GAAAAGAACC CTTGTTAAGG GAG 23

(2) INFORMATION FOR SEQ ID NO:72:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA to rRNA (iv) ANTI-SENSE: NO (vi) ORIGINAL SOURCE:
(A) ORGANISM: Chlamydiaceae (xi) SEQUENCE DESCRIPTION: SEQ ID NO:72:

-continued

```
CTTAACTCCC TGGCTCATCA TG                                          22

(2) INFORMATION FOR SEQ ID NO:73:

     (i) SEQUENCE CHARACTERISTICS:
          (A) LENGTH: 19 base pairs
          (B) TYPE: nucleic acid
          (C) STRANDEDNESS: single
          (D) TOPOLOGY: linear

    (ii) MOLECULE TYPE: cDNA to rRNA

    (iv) ANTI-SENSE: NO

    (vi) ORIGINAL SOURCE:
          (A) ORGANISM: Chlamydiaceae

    (xi) SEQUENCE DESCRIPTION: SEQ ID NO:73:

CAAAAGGCAC GCCGTCAAC                                              19
```

INTERGENIC SPACER TARGET SEQUENCE FOR DETECTING AND DISTINGUISHING CHLAMYDIAL SPECIES OR STRAINS

BACKGROUND OF THE INVENTION

1. Field of the Invention

This invention relates to a target nucleic acid sequence and to probes and primers that detect that target sequence in laboratory and clinical samples containing Chlamydiaceae.

2. Description of the Prior Art

The order Chlamydiales includes at least four families that are proven or suspected pathogens of humans or other animals: Parachlamydiaceae, Simkaniaceae, Waddliaceae, and Chlamydiaceae [Everett, K. D. E., et al. (1998), *Int J Syst Bacteriol*, Submitted; Rurangirwa, F. R., et al. (1998), *Int J Syst Bacteriol*, Submitted]. These pathogens have been associated with reproductive, respiratory, cardiovascular, gastrointestinal, or systemic disease, and conjunctivitis, arthritis, and encephalitis in the host animal [Everett, K. D. E., et al. (1997), *Int J Syst Bacteriol* 47: 461–473; Birtles, R. J., et al. (1997), Lancet 349: 925–926; Kahane, S., et al. (1998a), *J Infect Dis* In press; Kahane, S., et al. (1998b), In Proceedings of the *Third Meeting of the European Society for Chlamydia Research*, p. 18. Edited by A. Stary., Bologna, Italy: Study Group for STD and Dermatological Microbiology of the Austrian Society for Dermatology and Venerology; Lieberman, D., et al. (1997), *Am J Respir Crit Care Med* 156: 578–82]. Numerous Chlamydiaceae isolates comprising some 60 strains have been reported since the early 1900's. These belong to two genera and nine species, as determined by genetic and phenotypic criteria, and these species can be identified by DNA sequence analysis (Everett & Andersen, 1998). However, a rapid systematic technique to routinely distinguish all nine Chlamydiaceae species is not available.

Efforts to speciate chlamydial isolates have been ongoing since the early days of chlamydial research. Because chlamydiae only grow inside inclusions in host cells, the only distinguishing criteria that initially could be relied upon were inclusion morphology, sulfadiazine resistance, and the accumulation of glycogen within the cells. Eventually, strains were characterized by PCR-RFLP, type-specific antigens, host associations, and monoclonal antibodies (MAb) [Andersen, A. A. (1991), *J Clin Microbiol* 29: 707–711; Moulder, J. W., Hatch, T. P., Kuo, C. -C., Schachter, J. & Storz, J. (1984), Genus Chlamydia. In *Bergey's Manual of Systematic Bacteriology*, vol. 1., pp. 729–739. Edited by N. R. Krieg., Baltimore, Md.: The Williams & Wilkins Co.; Stephens, R. S., et al., (1982), *J Immunol* 128: 1083–1089; Wang, S. -P., et al. (1985), *J Infect Dis* 152: 791–800]. Today Chlamydiaceae isolates are generally distinguished by a variety of MAb or PCR tests that recognize only one strain or species at a time. These assays were developed using limited numbers of isolates and were not intended for speciating, per se. A number of problems associated with using these tests for speciation has becoming evident. For example, MAbs that recognize a "species-specific" *C. trachomatis* epitope (in variable-segment-IV of the major outer membrane protein) also probably recognize Chlamydia suis, according to DNA sequence analyses [Everett, K. D. E., et al., (1998), *Int J Syst Bacteriol*, Submitted]. Plasmid-based *C. trachomatis* tests originally thought to be species specific, do not detect plasmid-strains [An, Q., et al. (1994), *Mol Cell Probes* 8: 429–435; An, Q., et al. (1992), *J Clin Microbiol* 30: 2814–2821]. Because all of the species cannot be identified with a single test, they can be mistaken for one another or diagnosis can be missed. With only a limited amount of sequence data in hand, PCR tests have been developed that identify up to four species and two subclades [Holland, S. M., et al., (1990), *J Infect Dis* 162: 984–987; Kaltenbock, B., et al., (1997), *J Clin Microbiol* 35: 1835–1841; Meijer, A. et al., (1997), *J Clin Microbiol* 35: 1179–1183; Messmer, T. O., et al. (1997), *J Clin Microbiol* 35; Tong, C. Y., & Sillis, M. (1993), J Clin Pathol 46: 313–317]. For the most part, the primers used in these tests are a reasonable match to most target sequences, but these tests are incapable of distinguishing all nine species. Thus, our ability to examine the epidemiology and pathogenesis of chlamydial species has been critically limited.

PCR-RFLP may be used to identify bacterial species, and requires a target gene that has appropriately conserved and variable segments. The gene that expresses the major outer membrane protein, ompA (omp1), has now been completely sequenced from more than 50 strains and it is evident that excess sequence diversity in this gene limits its usability in PCR-RFLP identification of the nine chlamydial species (Everett et al., 1998, supra). The 7.5 kbp plasmid is also a poor target for systematic PCR-RFLP identification of Chlamydiaceae species because, in many strains, it is either uncharacterized or absent (Everett et al., 1998, supra).

Shah et al. (WO 90/15159) reported a series of oligonucleotide probes, 28–36 nucleotides in length, that were specific for *C. trachomatis*. These probes targeted either the 16S or the 23S rRNA or rDNA.

Longiaru et al. (U.S. Pat. No. 5,232,829) disclose a number of PCR primers and capture probes for amplifying and detecting *C. trachomatis*. These oligonucleotides targeted either the 16S or the 23S rRNA or rDNA.

Yang et al. (U.S. Pat. Nos. 5,512,445 and 5,514,551) show oligonucleotide probes and primers for the amplification and specific detection of *C. trachomatis*. These oligonucleotides are targeted to regions of the 16S and the 23S rRNA/rDNA.

Hogan et al. shows a series of probes and primers specific to rRNA of a number of bacteria. The probes and primer for *C. trachomatis* target variable regions of the 16S and 23S rRNA.

Goessens et al. present a comparison of three commercially available amplification assays for detecting *C. trachomatis* in urine samples. The sensitivity of these assays ranged from 90–96% and the specificities ranged from 98–99%.

SUMMARY OF THE INVENTION

We have now succeeded in identifying the intergenic spacer between the 16S and the 23S genes and a region of the 3' end of Domain I in the 23S region for 43 strains of Chlamydiaceae and have thereby identified a novel pair of target regions of the genome for assaying and identifying all strains of Chlamydiaceae. The sequence of this target region allows for the construction of suitable probes and primers that can be group-specific for the identification of all species of Chlamydiaceae, or species-specific, or even strain-specific. The appropriate selection of probe or primer set can be used to identify the presence of Chlamydiaceae in a test sample, or to distinguish one strain from another.

In accordance with this discovery, it is an object of the invention to provide a sensitive, specific, and rapid diagnostic tool for positively identifying Chlamydiaceae in a clinical or laboratory sample.

It is also an object of the invention to provide a target region for constructing probes and primer sets tailored to the desired specificity for detecting chlamydial infections.

Another object of the invention is to provide an improved method for diagnosing chlamydial infections in humans and animals.

Yet another object of the invention is to provide a diagnostic test for chlamydial infection that would distinguish the 9 species of Chlamydiaceae.

Other objects and advantages of the invention will become readily apparent from the ensuing description.

DEFINITIONS

Figure 1:
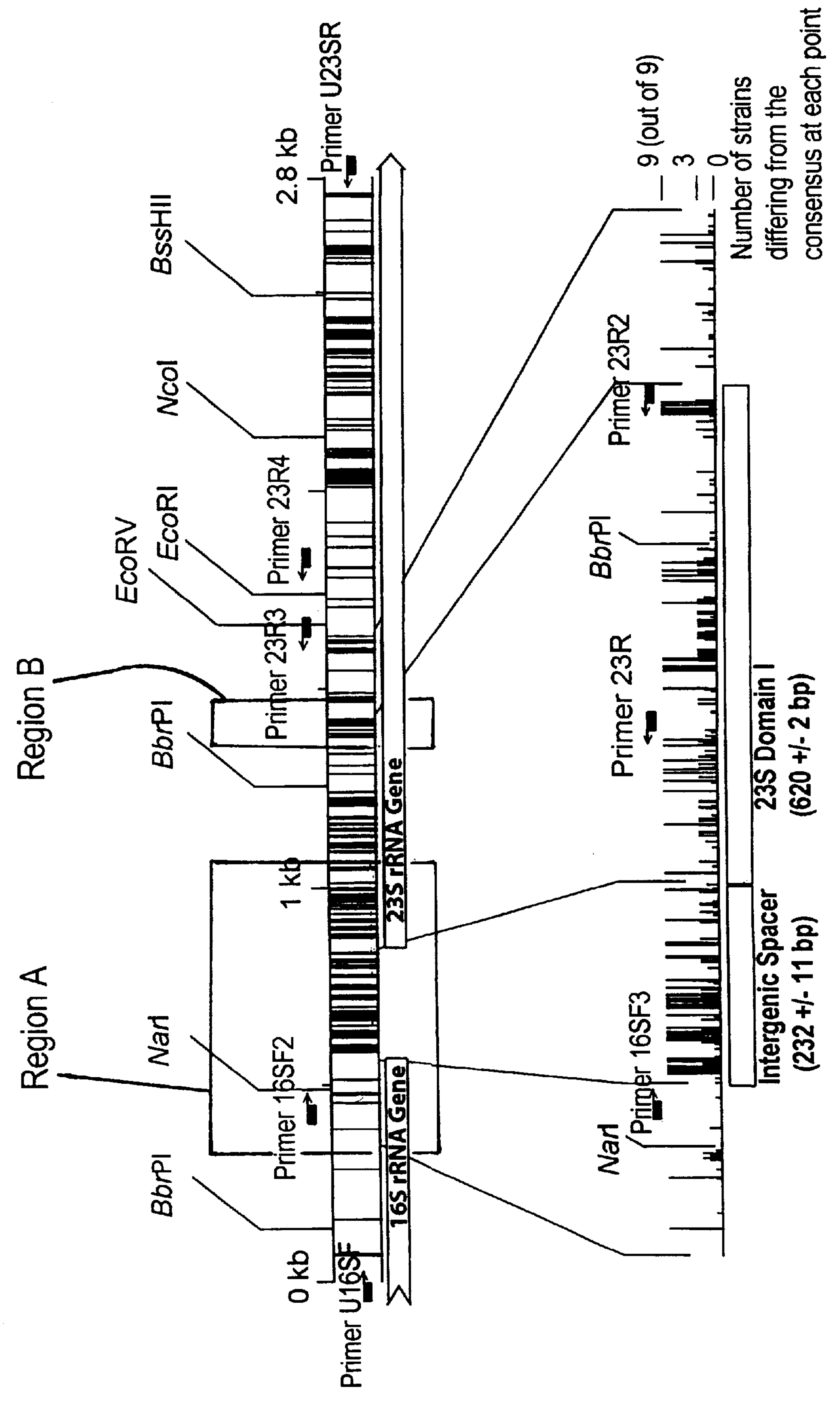
FIG. 1 is a map of ribosomal DNA for Chlamydiaceae species showing the location of the target regions of this invention relative to the 16S and the 23S ribosomal genes and further illustrating sequence differences among representative strains of the nine groups of chlamydiae.

As used herein, the expression "test sample" is intended to mean any clinical, laboratory, environmental or other collected sample of material that is suspected of containing the intended target nucleic acid which is to be detected. Exemplary test samples include swabs, scrapings or collections of food, body fluids or other sources of chlamydial contamination.

The expression "target nucleic acid" or "target sequence" is intended to include the sequence within Regions A and/or B of any one of rDNA SEQ ID Nos. 1–43 as defined in Table IV, below, as well as corresponding rRNA sequences, DNA or RNA sequences complementary to SEQ ID Nos. 1–43, and any portion of the aforementioned DNA or rRNA sequences that is of sufficient size to permit the desired level of identification. For those instances wherein the purpose of the diagnostic test is to ascertain the presence or absence of Chlamydiaceae spp., the target nucleic acid would preferably be a group-specific consensus sequence. Whereas, in those cases wherein it is desired to distinguish one species or strain of Chlamydiaceae over others, then a species or strain specific sequence would be the target nucleic acid.

The term "probe" is used herein in the broadest sense to refer to either a labeled or an unlabeled, single-stranded nucleic acid that will hybridize under predetermined conditions of stringency to the target nucleic acid. Such probes may be RNA or DNA and will typically be at least about 15 bases in length, and preferably about 20–100 bases in length. When used in a hybridization assay, hybrids formed from the probes and the target sequence are usually detected by means of a detectable label affixed directly to the probe. Alternatively, probes can be used as helper probes to facilitate binding of a separate labeled probe to the target nucleotide. It is understood that for hybridization to occur, the probe may or may not be exactly complementary to the target sequence, provided that the hybridization conditions are appropriately selected to permit hybridization even when there are a limited number of mismatches between the respective sequences.

The term "primer" is used herein in its usual sense to be descriptive of an oligonucleotide (RNA or DNA), usually about 15–30 nucleotides in length, and preferably about 17–26 bases in length, that will participate in a primer extension reaction when catalyzed by a polymerase. These reactions are more commonly referred to as "polymerase chain reactions". Contemplated herein as primers are only those nucleotides that are properly oriented so as to amplify a region within the target sequence.

The expression "substantial equivalent thereof" in reference to any target sequence or to the sequence of a probe or primer is intended to mean that minor additions, deletions, or mismatches can be present in the sequence to the extent that such variations do not prevent the hybridization or annealing of the nucleic acids essential to the assay.

"Stringency" refers to the conditions under which hybridization takes place. At high stringency, only exact matches of DNA and/or RNA will hybridize stably. Under low stringency, 80–90% homologous sequences may still hybridize.

The expression "sequence-specific oligonucleotide" is used herein to refer to probes or primers having a hybridizing region that is exactly complementary to a segment of the target region.

DETAILED DESCRIPTION OF THE INVENTION

The target sequence for use in the invention is principally the region of the intergenic spacer between the 16S and the 23S ribosomal genes including the far downstream (3') end of the 16S gene and the far upstream (5') end of the 23S Domain I flanking the intergenic spacer (see FIG. 1) hereafter referred to as Region A, and secondarily a 131-bp region in the 3' end of Domain I in the 23S rRNA, hereafter referred to as Region B. Region A is sometimes referred to herein as the "region of the intergenic spacer". The 16S/23S intergenic spacer lends itself to the development of species-specific DNA-based probes for Chlamydiaceae because it contains conserved sequence interspersed with species-specific segments. We have found that this rDNA segment is a phylogenetic marker for the nine chlamydial species and DNA sequence data for all species, including >40 strains.

To initially identify the target sequences, 2.8 kb partial ribosomal DNA segments from a *C. trachomatis* strain R22 and *C. psittaci* strain NJ1 were amplified by PCR and sequenced. Subsequently, 1320 bp of rDNA, including both the 16S/23S intergenic spacer (232±11 bp) and Domain I (620±2 bp) of the 23S gene, were selected and sequenced from each of 41 additional strains. Using both parsimony and percent distance analyses, these sequences were found to have variable regions that grouped the isolates into two lineages (*C. trachomatis* and non-*C. trachomatis*) with nine distinct genotypic groups. The *C. trachomatis* lineage included human, swine, and mouse/hamster groups. The non-*C. trachomatis* lineage included *C. pecorum, C. pneumoniae*, and *C. psittaci*-abortion, -avian, -feline, and -guinea pig groups. The 43 strains of Chlamydia spp. studied, included 18 strains of *C. psittaci*, 7 strains of *C. pneumoniae*, 6 strains of *C. pecorum*, and 12 strains of *C. trachomatis*.

In FIG. 1, the locations of primers that were conserved in all Chlamydia strains and that were particularly useful in the PCR and sequence analysis are indicated, as are conserved restriction sites. The vertical solid bars in the figure indicate sequence differences. The upper part of FIG. 1 is a sequence map comparison for the 2.8-kb ribosomal segment from *C. psittaci* NJ1 and swine strain *C. trachomatis* R22. The shaded regions of the 16S and 23S ribosomal genes plus the intergenic spacer were used for the double stranded sequence analysis performed with the 43 Chlamydiaceae strains. The lower part of FIG. 1 illustrates sequence differences among representative strains of the nine groups of chlamydiae (strains A/Har-$13^T$, R22, MoPn, $6BC^T$, B577, FML-12, FP, GPIC, and $E58^T$) . Each of the 43 Chlamydiaceae strains clustered with one of these strains on the basis of the ribosomal sequence. Either a G, A, T, or C or a gap was scored by absolute difference from the consensus sequence (one, two, or three bases different out of nine sequences) or by a finding of non consensus sequence in the nine representative strains (i.e. the plurality for consensus was six). The baseline indicates absolute consensus in all nine strains; no consensus is shown by the tallest solid bars; three differences from the consensus are indicated by the next-highest bars; and one or two differences are indicated by the shortest bars.

The 1320-bp regions sequenced for the additional 41 chlamydial strains mentioned above were aligned with the sequences of the 2.8-kb fragment of *C. psittaci* NJ1 and *C. trachomatis* R22 (Table I, below). These aligned fragments allowed identification of consensus regions and regions of variability from which to identify target regions for use in this invention. Target Regions A and B are identified in the Table.

The strategy for identifying useful probes or primers would be in accord with standard guidelines as well-known in the art. In general, the consensus regions would be the source of constructing group-specific probes or primers; whereas the regions of variability would be targeted for species or strain specific probes and primers. Other considerations would include the number or percentage of contiguous nucleotides within the targeted region that are identical to regions found in non-targeted organisms; the length of the selected target region; and the melt temperature of the selected target region. The methods for construction and use of probes and primers are well-established in the art.

A strategy for constructing an oligonucleotide useful as a probe or primer is initiated by predetermining the length of the oligonucleotide. As previously indicated, probes will typically be at least about 15 bases, and preferably about 20–100 bases, in length. Primers are more typically about 15–30 bases, and preferably about 17–26 bases, in length. The nucleotide sequence complementary to the target rRNA or rDNA is determined, and the oligodeoxyribonucleotide or oligoribonucleotide is synthesized as the inverse of the complementary sequence. In this way, the probe or primer is in the correct orientation for binding to native nucleic acid in the target sample.

As illustrated in Example 2, below, the taxonomic level of distinction between any two isolates can be predetermined by appropriate selection of the level of specificity of the primers or probes. A summary of the source Region for selecting the primers or probes for a desired level of specificity is given in Table V, below.

EXAMPLE 1

Bacterial Strains

Forty-three strains of Chlamydiaceae from both animal and human hosts were used (Table II). All organisms were previously characterized using microimmuno-fluorescence, serology, ompi sequence analysis, RFLP, DNA hybridization, and/or in vitro growth.

DNA Preparation, Amplification, and Cloning

Genomic DNAs from intact chlamydiae were prepared by incubating the chlamydiae at 37° C. in 50 to 100 $\mu$l of 50 mM dithiothreitol (DTT), 30 mM Tris/10 mM EDTA, pH 9.0, for 1 hour, adding an equal volume of 1% Nonidet® P-40 and incubating for 1 hour, adding RNase and incubating at 37° C. for 1 hour, extracting with phenol/chloroform (68), and finally, extracting with chloroform. Chlamydial material obtained as DNA or as lysates was treated with RNase prior to PCR amplification. Approximately 0.25 $\mu$g of template DNA was used in each 50 $\mu$l PCR reaction; higher concentrations of template DNA were used for specimens of DNA that had not been freshly prepared. The PCR Reagent Kit® (Perkin Elmer, Foster City, Calif.) was used to amplify a single-band PCR product of 2.8 kb from each strain in the Hybaid OmniGene Temperature Cycler® (Middlesex, England) with the following parameters: 30 cycles of 25 sec at 95° C., 15 sec at 55° C., 100 sec at 72° C., and a final 7 min extension at 72° C. The 16S oligonucleotide primer used in this amplification, U16SF, matched three known 16S chlamydial sequences (GenBank accession numbers M13769 [*C. psittaci* 6BC$^T$], M59178 [*C. trachomatis* L2/434/BU], and L06108 [*C. pneumoniae* TW-183$^T$]) at approximately position 990 of the 1540 bp gene. The 23S oligonucleotide primer used in this amplification, U23SR, complemented a highly conserved sequence at bacterial-23S-gene position 2000, far enough into the 2900 bp gene to obtain PCR products representing bonafide rRNA operons and to include a Chlamydiaceae-specific sequence, as well as possible intra-23S spacers. Primer sequences were:

U16SF: GCATGTGGTTTAATTCGATGCAACGC-GAAGAACC (SEQ ID No. 44); and

U23SR: GAATTTCGCTACCTTAGGACCGTTAT-AGTTAC (SEQ ID No. 45).

Clones of the 2.8 kb ribosomal PCR products were prepared for DNA sequencing using the TA Cloning Kit® (Invitrogen, San Diego, Calif.).

DNA Sequence Analysis

Oligonucleotide primer synthesis and DNA sequencing were performed by the Iowa State University DNA Sequencing and Synthesis Facility, Ames, Iowa. The full-length, cloned 2.8 kb PCR products from strain R22 and from strain NJ1 were subjected to double-stranded DNA sequence analysis. After comparison of these sequences, the homologous 2.8 kb PCR products were prepared from 41 additional strains (Table II). Clones and PCR products were characterized by cutting with the restriction enzyme EcoRI. EcoRI cut all 2.8 kb chlamydial PCR products at a single site, yielding fragments of 1.7 kb and 1.1 kb. A number of the 2.8 kb cloned PCR products obtained during clone screening could not be cut with EcoRI, and DNA sequence analysis of over 500 bases of each, using a Universal primer to the cloning vector, identified them as Mycoplasma orale ribosomal sequence.

A 1320 bp segment in each of these forty-one 2.8 kb products was subjected to double stranded DNA sequencing. Thirty-three of the sequences were obtained from clones of PCR product in pCRII vector (Invitrogen). Others were obtained from direct sequencing of 2.8 kb PCR products that were extracted with phenol/chloroform and chloroform [Sambrook, J., et al., (1989) Molecular Cloning: a laboratory manual, 2nd ed. Cold Spring Harbor, N.Y.] and concentrated over Microcon® 100 microconcentrators (Amicon Corp., Beverly, Mass.). R27, CT1, and GPIC were sequenced in their entirety from both PCR products and clones. Because *C. trachomatis* has been reported to have two ribosomal operons [Engel, J. N., et al. (1987), *J. Bacteriol.* 169:5678–5685; Fukushi, H., et al. (1993), *Int. J. Syst. Bacteriol.* 43:613–617], the highly variable segments of *C. trachomatis* strains A/Har-13$^T$, B/TW-5/OT, D/UW-3/CX, F/IC/CAL3, L2/434/BU, and R22 were sequenced from both clones and PCR products to look for ambiguous sequence data. Sequences for ten chlamydial strains (1710S, EBA, FPcello, IPA, N16, M56, L71, Par1, S45, TW-183$^T$) were obtained from PCR-product template alone. The 1320-bp rDNA segment was found be to highly variable among the 43 Chlamydiaceae strains.

Several primers were found to be particularly useful for PCR amplification and sequencing, because they matched or complemented all of the chlamydial sequences. The locations of these primers are shown in FIG. 1. Forward (upstream) primers are #16SF2 (CCGCCCGTCACATCATGG, SEQ ID No. 46) and #16SF3 (TCGTAACAAGGTAGCCC, SEQ ID No. 47). Complementary primers are #23R (TACTAAGATGTTTCAGTTC, SEQ ID No. 48), #23R2 (AAAAGGCACGCCGTCAACC, SEQ ID No. 49), #23R3 (GATATCTCCAAGTTTGATT, SEQ ID No. 50), and #23R4 (GAGCTGTTACGCACTCTTT, SEQ ID No. 51). Primer #16SF2 is located 150 bases before the 3-prime end of the 16S gene, primer #23R about 200 bases after the start of the 23S gene, primer #23R2 at the 3-prime end of Domain I, primer #23R3 about 12 bases beyond the end of the 1320 bp sequenced segment, and #23R4 about 1200 bp into the 23S gene. Double-stranded DNA sequencing data were compiled from approximately 70,000 bp of PCR products and/or clones. To gauge the accuracy of sequence analysis, over 10,000 bp were examined using both cloned and direct PCR templates.

Primer Extension Analysis

Total RNA was prepared from lysed *C. psittaci* 6GBC$^T$, *C. psittaci* NJ1, and *C. trachomatis* R22 by repeated phenol/chloroform extraction and DNase treatment, for template in primer extension analysis. Primer extension to identify the 5-prime end of the 23S rRNA was carried out using a conserved primer complementing the 23S chlamydial rRNA (#23R: TACTAAGATGTTTCAGTTC, SEQ ID No. 48) and the GeneAmp Thermostable rTth Reverse Transcriptase RNA PCR Kit® (Perkin Elmer). [$^{32}$P]dCTP was incorporated into the rTth reverse transcriptase product with the following changes to the manufacturer's recommended conditions: the reverse transcription mix was prepared using unlabeled dCTP at half of the recommended concentration, $MnCl_2$ and rTth enzyme were omitted, and the mix was heated for 5 min in a boiling water bath. The heated mix was cooled rapidly on ice and 40$\mu$Ci of [$^{32}$P]dCTP (ICN, Irvine, Calif.) along with $MnCl_2$ and rTth enzyme were added.

Extension was carried out for 1 cycle in a GeneAmp PCR System 9600® (Perkin Elmer) for 10 min at 50° C., 15 min at 70° C., and 1 min at 95° C. For each chlamydial strain, one sequence ladder was prepared with [$^{32}$P]dCTP label and another with [$^{35}$S]dATP (ICN) using the CircumVent Thermal Cycle Dideoxy DNA Sequencing Kit® (New England Biolabs, Beverly, Mass.).

DNA Analysis Programs and Output

Sequence analysis programs described in the Program Manual for the Wisconsin Package, Version 8, September 1994 (Genetics Computer Group, 575 Science Drive, Madison, Wis. USA 53711) were used for DNA and RNA analysis. These programs were Reformat, SeqEd, BestFit, Gap, Reverse, Assemble, PileUp, Pretty, LineUp, Distances, FastA, RNAfold, and Squiggles. Phylogenetic distances were determined by Robin M. Bush and Walter Fitch using parsimony analysis (PAUP v3.1) (83). Branching order reliability was evaluated by 100 replications of bootstrap resampling (21). Sequence data were examined in four ways: 1) a PileUp multiple sequence alignment was prepared, including appropriate gaps and substitutions (see Table I); 2) using the PileUp alignment, distance analysis tables of Jukes-Cantor pairwise corrected percent differences (42) were generated for the intergenic spacer and for Domain I [Tables 2, 3, and 4 summarize these data]; 3) outgroup sequence data were obtained from GenBank for *Pirellula marina* [accession number X07408] and by DNA sequencing of Simkania "Z" and "Z1"; and 4) the sequences were analyzed using PAUP, the most parsimonious consensus trees were prepared, and branching order reliability was tested by 100 replications of bootstrap sampling [FIGS. 4 and 5]. Finally, biological, serological, and host range data and the rooted Domain I tree were compiled (Table II).

GenBank Accession Numbers

DNA sequence data for the ribosomal segments described in this study appear in the GenBank database with accession numbers U68419 through U68460, U76710, and U76711.

Characterization of Sequence Diversity Within a 2.8 kb Portion of the Ribosomal Operon The 2.8 kb cloned ribosomal PCR products from swine strain R22 and turkey strain NJ1 of Chlamydia contained approximately one-third of the 16S gene, the intergenic spacer, and two-thirds of the 23S gene. Comparison of the two sequences is shown in FIG. 1. The 23S gene start site (TACAGACCAAGT . . . ; SEQ ID No. 52) was located four bases upstream of the homologous *Escherichia coli* site (data not shown). The 5-prime ends of the two segments each contained 563 bp of DNA homologous to 16S gene sequences, differing from each other by only 3%. A search of the GenBank database with the 16S segments indicated that R22 was most closely related to *C. trachomatis* and NJ1 was most closely related to *C. psittaci*. The 16S/23S intergenic spacer sequences of R22 and NJ1 were 243 bp and 224 bp in length, respectively, and differed by 22.0%. The 1960-base, 23S gene segments differed by 9.6%. Much of the variability in the 23S segment was in the 5-prime end homologous to Domain I of the *E. coli* 23S gene. The Domain I sequences of R22 and NJ1 (622 bp and 621 bp, respectively) differed by 17% while the remaining portion of the 23S segments (1338 bp) varied by 6.4%. No intragenic spacers were identified within the chlamydial 23S genes.

Analysis of the Ribosomal Intergenic Spacer

The 16S/23S intergenic spacer sequences from chlamydiae identified in Table II are indicated in the multiple sequence alignment in Table I. The intergenic spacers spanned 232±11 bases depending on the strain. Nine single-base differences were unique to only one or two strains, and approximately 80 sequence position differences were group-clustered, conserved by species, subspecies, or several species. Among these 80 positions were three highly variable segments of approximately 20 bp each between base 12 and base 115 that were distinctly group-cluster specific. Foldrna/Squiggles analysis of the intergenic spacer indicated that each of the α segments could form a hairpin structure with a 10 bp stem centered between bases 23 and 24 (analyses not shown).

A comparison of the intergenic spacers showed that there were 143 base positions (56.1%) that were absolute identities among all chlamydial strains. This compared to 74.2% absolute identity for Domain I and 91% for 16S.

EXAMPLE 2

Development of Useful Primers

Primers having various levels of specificity were identified as described below. The conditions for PCR amplifications using these primers are uniform, except for annealing temperatures which are given below in each instance. Typically, the phases of each cycle are 30 sec at 94° C., 15 sec annealing, and 30 sec at 72° C. Cycle numbers may be relatively low (30) or higher, depending on the amount of template. Equimolar quantities of primer are recommended in each reaction. For all of these assays, a heat-activated DNA polymerase such as AmpliTaq Gold® is recommended for the purpose of obtaining optimal specificity.

Test 1

U23F: 5' GATGCCTTGGCATTGATAGGCGATGAAGGA 3' (SEQ ID No. 53)

23SIGR: 5' TGGCTCATCATGCAAAAGGCA 3' (SEQ ID No. 54)

(annealing temperature 61° C.)

These primers PCR amplify the 23S signature sequence of all Chlamydiaceae, of Simkaniaceae, and of many other bacteria. Signature sequence data is used for rapid identification of each of the nine species in Chlamydiaceae. These primers can be used for direct DNA sequencing of the PCR product that they produce. The broad specificity of these primers ensures that if a chlamydia-like bacterium is isolated, sequence data can be obtained that will allow rapid identification of the organism.

Test 2

IGF: 5' GACTAGGTTGGGCAAG 3' (SEQ ID No. 55)

IGR: 5' AGCTCTTA(t/g/a) (c/t)AACTTGGTCTGTA 3' (SEQ ID No. 56)

(annealing temperature 57° C.)

These primers will amplify in PCR the intergenic spacer of all Chlamydiaceae spp. and are specific only for Chlamiydiaceae. That is, they should not amplify an appropriately-sized product from other bacterial templates. IGF is located within the 16S/23S intergenic spacer and is the forward primer. IGR complements the start of the 23S rRNA gene and is the reverse primer. PCR amplification of Chlamydiaceae template with these primers generates an approximately 230-base PCR product that can be directly sequenced for identification or that may serve as a probe in hybridization experiments. Using this PCR product, specific restriction analysis can also be conducted for species or strain identification.

Test 2B (PROBE)

SIGF: 5'-ATAATAATAGACGTTTAAGA-3' (SEQ ID No. 57);

(annealing temperature 52° C.)

This oligonucleotide, located a little more than 100 bases downstream of the IGF primer, also recognizes all Chlamydiaceae spp. SIGF will anneal to denatured template DNA or to PCR products. It can be used for sequence analysis or as a hybridization probe. Because this oligonucleotide is A/T rich and may amplify nonspecifically from A/T-rich sites, its potential as a primer is diminished. To use SIGF to confirm the identity of template DNAs or PCR products like IGF/IGR, target DNA is bound to a substrate, denatured, and probed with labeled SIGF. Detectable SIGF hybridization indicates that the target is derived from Chlamydiaceae.

Test 3

Detection of all Members of Chlamydiaceae Using High Throughput, Fluorescent Probe Detection with the Perkin Elmer TaqMan® System The TaqMan® system will detect either DNA or RNA targets that match or complement the Chlamydiaceae-specific primers and probe identified below as SEQ ID Nos. 71–73, occurring in Region B. When matching target nucleic acids are present, PCR or RT-PCR using oligonucleotides produces a fluorescent reporter that is detected using an argon lamp or laser in the TaqMan® System. Readings can be taken at the end of each amplification cycle or at the endpoint. This system provides superb quantitative and qualitative target identification. For endpoint detection after 80-min of cycling, a microtiter plate with 90 samples and 6 negative controls can be analyzed in less than 10 minutes.

| | |
|---|---|
| Forward (coding strand) | GAAAAGAACCCTTGTTAAGGGAG<br>SEQ ID No. 71 |
| Reverse (noncoding strand) | CTTAACTCCCTGGCTCATCATG<br>SEQ ID No. 72 |
| Probe (noncoding strand) | FAM-CAAAAGGCACGCCGTCAAC-TAMRA<br>SEQ ID No. 73 |

Test 4

With the recent introduction of genetic analysis techniques for the identification of organisms, bacterial nomenclature and speciation has undergone a revolution. Based on the information provided in this study and other genetic data, it has been possible to apply the new genetic principles to the designation of species and genera in Chlamydiaceae. Although not yet approved by the *International Journal of Systematic Bacteriology*, Table III outlines a proposal for chlamydial speciation that is currently being considered. The proposed nomenclature for these genera and species is used throughout Test 4.

Genus and Species Specific Primers for PCR Amplification

The following primers can be used in PCR amplifications followed by gel detection to identify the 2 proposed genera in Chlamydiaceae and also to identify the 9 species. Each set of Chlamydiaceae-specific primers consists of a forward (F) and a reverse (R) primer. There is one R primer for the genus Chlamydia and a different R primer for the genus Chlamydophila. If simply knowing the genus of the unknown template is desired, amplifications are done using primer IGF (above) and either the Chlamydia R primer and or the Chlamydophila R primer:

Chlamydia R 5' GCCGGAGCTTTTCGCA 3' (SEQ ID No. 58); (annealing temperature 71° C.).

Chlamydophila R 5' GCAGGTAAACGCATCCTTCA 3' (SEQ ID No. 59); (annealing temperature 72° C.). A positive identification of the genus is the production of an approximately 300-bp PCR product.

| | CHLAMYDIA R | CHLAMYDOPHILA R |
|---|---|---|
| Chlamydia + primer IGF | ++++ | |
| Chlamydophila + primer IGF | | ++++ |

To identify a species that belongs to one of these genera, the original template or a small amount of PCR product from the genus-specific amplification can be used in the following PCR assays. If a specimen is a mixed sample of both genera, use of the genus-specific amplification product will serve to significantly purify the desired target and is recommended for use with the following tests. The PCR products generated with these primers are nearly 300 bases in length, including sequence from the 16S/23S intergenic spacer and an approximately 80-base segment of the 23S rRNA gene (the *abortus/psittaci* products, however, are approximately 100 bases long). Predicted annealing temperatures are indicated. When two primers are used together, the lower of the 2 annealing temperatures should be used.

For Chlamydia-specific PCR amplification, the Chlamydia R primer and the following forward (F) primers are used:

| | | SEQ ID No. | anneal temp. |
|---|---|---|---|
| muridarum F | 5' TGTTAAGGTGGCGCGA 3' | 60 | 67° C. |
| trachomatis F | 5' GTTAAGAGTAGCGCGGTGA 3' | 61 | 67° C. |
| suis F | 5' CATTTGCATTGTTAAGGTAGC 3' | 62 | 66° C. |

| | F = muridarum | F = suis | F = trachomatis |
|---|---|---|---|
| *C. muridarum* + R | ++++ | + | |
| *C. suis* + R | | ++++ | |
| *C. trachomatis* + R | | + | ++++ |

For identification of a Chlamydia sample, a *C. suis* F primer amplification should be used as a control for every test. If the *C. suis* yields more PCR product than the other F primers, the sample is *C. suis*. If the other primers yield more product, the sample is *C. muridarum* or *C. trachomatis*, respectively.

For Chlamnydophila-specific PCR amplification, the Chlamiydophila R primer and the following forward (F) primers are used:

| | | SEQ ID No. | anneal temp. |
|---|---|---|---|
| pecorum F | 5' GGCAAGCATTTGCTGTGTA 3' | 63 | 68° C. |
| pneumoniae F | 5' GCAAGTATTTTATATTCCGCA 3' | 64 | 66° C. |
| felis/ caviae F | 5' GGGCAAGCATCTTTGAAAA 3' | 65 | 69° C. |
| abortus/ psittaci F | 5' CGTTGTTTCCAACACATTTA 3' | 66 | 65° C. |
| 2° psittaci F | 5' AATAGACGTTTAAGAATATATGTCTTTA 3' | 67 | 67° C. |
| 2° abortus F | 5' TTTAAGAATATCTGTCTTTGGTGA 3' | 68 | 67° C. |
| 2° felis F | 5' TTGTTAAGCGTGGGTTACA 3' | 69 | 65° C. |
| 2° caviae F | 5' TTAAGCGCTCGTTTCCA 3' | 70 | 66° C. |

It is noted in the *abortus/psittaci* F primer, above, that the fourth occurrence of cytosine (underlined) is a deliberate mismatch to the actual *abortus/psittaci* sequence. This one-base mismatch is intended to destabilize the primer from annealing to *caviae/pecorum/felis/pneumoniae* templates, but is not sufficient to destabilize annealing to the *abortus/psittaci* template.

To identify Chlamydophila species, the R primer is used in four separate PCR amplifications: *pecorum F, pneumoniae F, felis/caviae F*, and *abortus/psittaci F*. There is no template crossreaction between these four tests. If the *felis/caviae* or *abortus/psittaci* products are produced, then secondary (2°) PCR amplifications are run using a small amount of the initial PCR product, to determine which of the two species is present.

| | F = PEC | F = PNEU | F = FP/CA | F = AB/PS | 2° = FP | 2° = CA | 2° = AB | 2° = PS |
|---|---|---|---|---|---|---|---|---|
| *C. pecorum* + R | ++++ | | | | | | | |
| *C. pneumoniae* + R | | ++++ | | | | | | |

TABLE I

Alignment of Intergenic Spacers for 43 Chlamydia Strains

```
>CPU68419 2751 bp DNA. ---------C --------T- -T-------- A--------- ---------- ------GG-- A--------- ---------- ---------- ----------
>CTU68420 2762 bp DNA. ---------T --------C- -A-------- G--------- ---------- ------AT-- G--------- ---------- ---------- ----------
 #1                     .........................................................................................................
                      TTACCTGGGY TTGACATGYA TWTGACCGCG RCAGAAATGT CGTTTTCCGC AAGGACRKAT RCACAGGTGC TGCATGGCTG TCGTCAGCTC GTGCCGTGAG
                               *          *   *          *                          **    *

>CPU68419 2751 bp DNA.---------- ---------- ---------- ---------- ---------A ---------- ---------- ---------- ---------- ----------
>CTU68420 2762 bp DNA.---------- ---------- ---------- ---------- ---------G ---------- ---------- ---------- ---------- ----------
 #101                 .............................................................................................................
                      GTGTTGGGTT AAGTCCCGCA ACGAGCGCAA CCCTTATCGT TAGTTGCCAR CACTTAGGGT GGGAACTCTA ACGAGACTGC GTGGGTTAAC CAGGAGGAAG
                                                                         *                                          *

>CPU68419 2751 bp DNA.---------- ---------- ---------- ---------- --T------- ---------- ---------- ---------- T--------- ----------

>CTU68420 2762 bp DNA.---------- ---------- ---------- ---------- --G------- ---------- ---------- ---------- G--------- ----------

 #201                 .............................................................................................................
                      GCGAGGATGA CGTCAAGTCA GCATGGCCCT TATGCCCAGG GCKACACACG TGCTACAATG GCCAGTACAG AAGGTAGCAA KATCGTGAGA TGGAGCAAAT
                                                                  *                                         *

>CPU68419 2751 bp DNA.---C------ ---------- ---------- ---------- ---------- ---------- ---------- ---------- T--------- ----------
>CTU68420 2762 bp DNA.---T------ ---------- ---------- ---------- ---------- ---------- ---------- ---------- ---------- ----------
>CPU68432 1284 bp DNA.                                                 ----- ---------- ---------- ---------- ---------- ----------
>CPU68454 1283 bp DNA.                                                 ----- ---------- ---------- ---------- T--------- ----------
>CPU68424 1284 bp DNA.                                                 ----- ---------- ---------- ---------- ---------- ----------
>CPU68439 1284 bp DNA.                                                 ----- ---------- ---------- ---------- ---------- ----------
>CTU68440 1304 bp DNA.                                                 ----- ---------- ---------- ---------- ---------- ----------
>CTU68428 1299 bp DNA.                                                 ----- ---------- ---------- ---------- ---------- ----------
>CPU68434 1284 bp DNA.                                                 ----- ---------- ---------- ---------- ---------- ----------
>CPU68448 1283 bp DNA.                                                 ----- ---------- ---------- ---------- T--------- ----------
>CPU68433 1284 bp DNA.                                                 ----- ---------- ---------- ---------- ---------- ----------
>CTU68442 1304 bp DNA.                                                 ----- ---------- ---------- ---------- ---------- ----------
>CTU68437 1303 bp DNA.                                                 ----- ---------- ---------- ---------- ---------- ----------
>CTU68441 1304 bp DNA.                                                 ----- ---------- ---------- ---------- ---------- ----------
>CPU68431 1284 bp DNA.                                                 ----- ---------- ---------- ---------- ---------- ----------
>CTU68436 1303 bp DNA.                                                 ----- ---------- ---------- ---------- ---------- ----------
>CTU68430 1302 bp DNA.                                                 ----- ---------- ---------- ---------- ---------- ----------
>CTU68429 1298 bp DNA.                                                 ----- ---------- ---------- ---------- ---------- ----------
>CTU68443 1304 bp DNA.                                                 ----- ---------- ---------- ---------- ---------- ----------
>CPU68435 1284 bp DNA.                                                 ----- ---------- ---------- ---------- ---------- ----------
>CTU68427 1299 bp DNA.                                                 ----- ---------- ---------- ---------- ---------- ----------
>CPU68445 1282 bp DNA.                                                 ----- ---------- ---------- ---------- T--------- ----------
>CPU68452 1284 bp DNA.                                                 ----- ---------- ---------- ---------- T--------- ----------
>CPU68444 1282 bp DNA.                                                 ----- ---------- ---------- ---------- T--------- ----------
>CPU68456 1284 bp DNA.                                                 ----- ---------- ---------- ---------- T--------- ----------
>CPU76710 1282 bp DNA.                                                 ----- ---------- ---------- ---------- T--------- ----------
>CPU68455 1284 bp DNA.                                                 ----- ---------- ---------- ---------- T--------- ----------
>CTU68438 1304 bp DNA.                                                 ----- ---------- ---------- ---------- ---------- ----------
>CPU68457 1285 bp DNA.                                                 ----- ---------- ---------- ---------- T--------- ----------
```

TABLE I-continued

Alignment of Intergenic Spacers for 43 Chlamydia Strains

```
>CPU68446 1282 bp DNA.                                                      ----- ---------- ---------- ---------- T--------- ----------
>CPU68447 1284 bp DNA.                                                      ----- ---------- ---------- ---------- T--------- ----------
>CPU68449 1284 bp DNA.                                                      ----- ---------- ---------- ---------- T--------- ----------
>CPU68453 1283 bp DNA.                                                      ----- ---------- ---------- ---------- T--------- ----------
>CPU76711 1284 bp DNA.                                                      ----- ---------- ---------- ---------- ---------- ----------
>CPU68422 1284 bp DNA.                                                      ----- ---------- ---------- ---------- ---------- ----------
>CPU68426 1284 bp DNA.                                                      ----- ---------- ---------- ---------- ---------- ----------
>CPU68425 1284 bp DNA.                                                      ----- ---------- ---------- ---------- ---------- ----------
>CPU68421 1282 bp DNA.                                                      ----- ---------- ---------- ---------- T--------- ----------
>CPU68458 1285 bp DNA.                                                      ----- ---------- ---------- ---------- T--------- ----------
>CPU68451 1284 bp DNA.                                                      ----- ---------- ---------- ---------- T--------- ----------
>CPU68423 1284 bp DNA.                                                      ----- ---------- ---------- ---------- ---------- ----------
>CPU68450 1284 bp DNA.                                                      ----- ---------- ---------- ---------- T--------- ----------
>CPU68459 1285 bp DNA.                                                      ----- ---------- ---------- ---------- T--------- ----------
 #301                 ...................................................................................................................
                      CCTYAAAGCT GGCCCCAGTT CGGATTGTAG TCTGCAACTC GACTACATGA AGTCGGAATT GCTAGTAATG GCGTGTCAGC CATAACGCCG TGAATACGTT
                         *                                                 →Region A                           *

>CPU68419 2751 bp DNA.---------- ---------- ---------- ---------- ------G--- ---------- ---------- T--------- ---------- ----------
>CPU68420 2762 bp DNA.---------- ---------- ---------- ---------- ---------- ---------- --------C- ---G:----- ---------- ----------
>CPU68432 1284 bp DNA.---------- ---------- ---------- ---------- -----C---- ---------- ---------A TTTTT----- G--------- ----------
>CPU68454 1283 bp DNA.---------- ---------- ---------- ---------- ------G--- ---------- ---------- --A:------ ---------- ----------
>CPU68424 1284 bp DNA.-T-------- ---------- ---------- ---------- ---------- ---------- ---------A TTT-T----- ---------- ----------
>CPU68439 1284 bp DNA.---------- ---------- ---------- ---------- -----C---- ---------- ---------A TTTTT----- G--------- ----------
>CPU68440 1304 bp DNA.---------- ---------- ---------- ---------- ---------- ---------- --------C- ----G:---- ---------- ----------
>CPU68428 1299 bp DNA.---------- ---------- ---------- ---------- ---------- ---------- --------C- ----G:---- ---------- ----------
>CPU68434 1284 bp DNA.---------- ---------- ---------- ---------- -----C---- ---------- ---------A TTTTT----- G--------- ----------
>CPU68448 1283 bp DNA.---------- ---------- ---------- ---------- ------G--- ---------- ---------- --A:------ ---------- ----------
>CPU68433 1284 bp DNA.---------- ---------- ---------- ---------- -----C---- ---------- ---------A TTTTT----- G--------- ----------
>CPU68442 1304 bp DNA.---------- ---------- ---------- ---------- ---------- ---------- --------C- ----G:---- ---------- ----------
>CPU68437 1303 bp DNA.---------- ---------- ---------- ---------- ---------- ---------- --------C- ----G:--G- -H-------- ----------
>CPU68441 1304 bp DNA.---------- ---------- ---------- ---------- ---------- ---------- --------C- ----G:---- ---------- ----------
>CPU68431 1284 bp DNA.---------- ---------- ---------- ---------- -----C---- ---------- ---------A TTTTT----- G--------- ----------
>CTU68436 1303 bp DNA.---------- ---------- ---------- ---------- ---------- ---------- --------C- ----G:--G- ---------- ----------
>CTU68430 1302 bp DNA.---------- ---------- ---------- ---------- ---------- ---------- --------C- -G--G:--G- ---------- ----------
>CTU68429 1298 bp DNA.---------- ---------- ---------- ---------- ---------- ---------- --------C- ----G:---- ---------- ----------
>CTU68443 1304 bp DNA.---------- ---------- ---------- ---------- ---------- ---------- --------C- ----G:---- ---------- ----------
>CPU68435 1284 bp DNA.---------- ---------- ---------- ---------- -----C---- ---------- ---------A TTTTT----- G--------- ----------
>CTU68427 1299 bp DNA.---------- ---------- ---------- ---------- ---------- ---------- --------C- ----G:---- ---------- ----------
>CPU68445 1282 bp DNA.---------- ---------- ---------- ---------- ------G--- ---------- ---------- ---------- ---------- ----------
>CPU68452 1284 bp DNA.---------- ---------- ---------- ---------- ------G--- ---------- ---------- T--------- ---------- ----------
>CPU68444 1282 bp DNA.---------- ---------- ---------- ---------- ------G--- ---------- ---------- ---------- ---------- ----------
>CPU68456 1284 bp DNA.---------- ---------- ---------- ---------- ------G--- ---------- ---------- ---------- ---------- ----------
>CPU76710 1282 bp DNA.---------- ---------- ---------- ---------- ------G--- ---------- ---------- ---------- ---------- ----------
>CPU68455 1284 bp DNA.---------- ---------- ---------- ---------- ------G--- ---------- ---------- ---------- ---------- ----------
>CTU68438 1304 bp DNA.---------- ---------- ---------- ---------- ---------- ---------- --------C- ----G:---- ---------- ----------
>CPU68457 1285 bp DNA.---------- ---------- ---------- ---------- ------G--- ---------- ---------- ---------- ---------- ----------
>CPU68446 1282 bp DNA.---------- ---------- ---------- ---------- ------G--- -------A-- -T-------- ---------- ---------- ----------
>CPU68447 1284 bp DNA.---------- ---------- ---------- ---------- ------G--- ---------- ---------- ---------- ---------- ----------
>CPU68449 1284 bp DNA.---------- ---------- ---------- ---------- ------G--- ---------- ---------- ---------- ---------- ----------
```

TABLE I-continued

Alignment of Intergenic Spacers for 43 Chlamydia Strains

```
>CPU68453 1283 bp DNA.---------- ---------- ---------- ---------- ------G--- ---------- ---------- ---------- ---------- ----------
>CPU76711 1284 bp DNA.-T-------- ---------- ---------- ---------- ---------- ---------- ---------A TTT-T----- ---------- ----------
>CPU68422 1284 bp DNA.-T-------- ---------- ---------- ---------- ---------- ---------- ---------A TTT-T----- ---------- ----------
>CPU68426 1284 bp DNA.---------- ---------- ---------- ---------- ---------- ---------- G--------A TTT-T----- ---------- ----------
>CPU68425 1284 bp DNA.-T-------- ---------- ---------- ---------- ---------- ---------- ---------A TTT-T----- ---------- ----------
>CPU68421 1282 bp DNA.---------- ---------- ---------- ---------- ------G--- ---------- ---------- ---------- ---------- ----------
>CPU68458 1285 bp DNA.---------- ---------- ---------- ---------- ------G--- ---------- ---------- ---------- ---------- ----------
>CPU68451 1284 bp DNA.---------- ---------- ---------- ---------- ------G--- ---------- ---------- ---------- ---------- ----------
>CPU68423 1284 bp DNA.-T-------- ---------- ---------- ---------- ---------- ---------- ---------A TTT-T----- ---------- ----------
>CPU68450 1284 bp DNA.---------- ---------- ---------- ---------- ------G--- ---------- ---------- ---------- ---------- ----------
>CPU68459 1285 bp DNA.---------- ---------- ---------- ---------- ------G--- ---------- ---------- ---------- ---------- ----------
 #401                 .............................................................................................................
                      CCCGGGCCTT GTACACACCG CCCGTCACAT CATGGGAGTT GGTTTTACCT TAAGTCGTTG ACTCAACCTG CA:A:AGGAG AGAGGCGCCC AAGGTGAGGC
                       *                                                **            *    **      ** ******  *   **

>CPU68419 2751 bp DNA.---------- ---------- ---------- ---------- ---------- ---------- ---------- --------T- ---------- ----------
>CPU68420 2762 bp DNA.--------A- ---------- ---------- ---------- ---------- ---------- ---------- ---------G -A:-C--G:- AA-G-T--C-
>CPU68432 1284 bp DNA.---------- ---------- ---------- ---------- ---------- ---------- ---------- ---------- G--A--AA-T -T-TA-C---
>CPU68454 1283 bp DNA.---------- ---------- ---------- ---------- ---------- ---------- ---------- --------T- ---------- ----------
>CPU68424 1284 bp DNA.---------- ---------- ---------- ---------- ---------- ---------- ------T--- --C------G GT---T---T A:--AACC-C
>CPU68439 1284 bp DNA.---------- ---------- ---------- ---------- ---------- ---------- ---------- ---------- G--A--AA-T -T-TA-C---
>CTU68440 1304 bp DNA.--------A- ---------- ---------- ---------- ---------- ---------- ---------- ---------G -A:-C--G:- -AGG-T--C-
>CTU68428 1299 bp DNA.--------A- ---------- ---------- ---------- ---------- ---------- ---------- ---------G -A:-C--G:- AA-G-T--C-
>CPU68434 1284 bp DNA.---------- ---------- ---------- ---------- ---------- ---------- ---------- ---------- G--A--AA-T -T-TA-C---
>CPU68448 1283 bp DNA.---------- ---------- ---------- ---------- ---------- ---------- ---------- --------T- ---------- ----------
>CPU68433 1284 bp DNA.---------- ---------- ---------- ---------- ---------- ---------- ---------- ---------- G--A--AA-T -T-TA-C---
>CTU68442 1304 bp DNA.--------A- ---------- ---------- ---------- ---------- ---------- ---------- ---------G -A:-C--G:- -A-G-T--C-
>CPU68437 1303 bp DNA.---------- ---------- ---------- ---------- ---------- ---------- ---------- ---------G -A:-C--G:- -A-G-T--C-
>CPU68441 1304 bp DNA.--------A- ---------- ---------- ---------- ---------- ---------- ---------- ---------G -A:-C--G:- -A-G-T--C-
>CPU68431 1284 bp DNA.---------- ---------- ---------- ---------- ---------- ---------- ---------- ---------- G--A--AA-T -T-TA-C---
>CPU68436 1303 bp DNA.---------- ---------- ---------- ---------- ---------- ---------- ---------- ---------G -A:-C--G:- -A-G-T--C-
>CPU68430 1302 bp DNA.--------A- ---------- ---------- ---------- ---------- ---------- ---------- ---------G -A:-C--G:- -A-G-T--C-
>CPU68429 1298 bp DNA.--------A- ---------- ---------- ---------- ---------- ---------- ---------- ---------G -A:-C--G:- AA-G-T--C-
>CPU68443 1304 bp DNA.--------A- ---------- ---------- ---------- ---------- ---------- ---------- ---------G -A:-C--G:- -A-G-T--C-
>CPU68435 1284 bp DNA.---------- ---------- ---------- ---------- ---------- ---------- ---------- ---------- G--A--AA-T -T-TA-C---
>CPU68427 1299 bp DNA.--------A- ---------- ---------- ---------- ---------- ---------- ---------- ---------G -A:-C--G-- AA-G-T--C-
>CPU68445 1282 bp DNA.---------- ---------- ---------- ---------- --------A- ---------- ---------- --------T- ---------- ----------
>CPU68452 1284 bp DNA.---------- ---------- ---------- ---------- ---------- ---------- ---------- --------T- ---------- ----------
>CPU68444 1282 bp DNA.---------- ---------- ---------- ---------- ---------- ---------- ---------- --------T- ---------- ----------
>CPU68456 1284 bp DNA.---------- ---------- ---------- ---------- ---------- ---------- ---------- --------T- ---------- ----------
>CPU76710 1282 bp DNA.---------- ---------- ---------- ---------- ---------- ---------- ---------- --------T- ---------- ----------
>CPU68455 1284 bp DNA.---------- ---------- ---------- ---------- ---------- ---------- ---------- --------T- ---------- ----------
>CPU68438 1304 bp DNA.--------A- ---------- ---------- ---------- ---------- ---------- ---------- ---------G -A:-C--G:- -AGG-T--C-
>CPU68457 1285 bp DNA.---------- ---------- ---------- ---------- ---------- ---------- ---------- --------T- --C--T---- ----------
>CPU68446 1282 bp DNA.---------- ---------- ---------- ---------- ---------- ---------- ---------- --------T- ---------- ----------
>CPU68447 1284 bp DNA.---------- ---------- ---------- ---------- ---------- ---------- ---------- --------T- ---------- ----------
>CPU68459 1284 bp DNA.---------- ---------- ---------- ---------- ---------- ---------- ---------- --------T- ---------- ----------
>CPU68453 1283 bp DNA.---------- ---------- ---------- ---------- ---------- ---------- ---------- ---------- ---------- ----------
>CPU76711 1284 bp DNA.---------- ---------- ---------- ---------- ---------- ---------- ------T--- --C------G GT---T---T A:--AACC-C
>CPU68422 1284 bp DNA.---------- ---------- ---------- ---------- ---------- ---------- ------T--- --C------G GT---T---T A:--AACC-C
```

TABLE I-continued

Alignment of Intergenic Spacers for 43 Chlamydia Strains

```
>CPU68426 1284 bp DNA.---------- ---------- ---------- ---------- ---------- ---------- ------T--- --C------G GT---T---T A:--AACC--
>CPU68425 1284 bp DNA.---------- ---------- ---------- ---------- ---------- ---------- ------T--- --C------G GT---T---T A:--AACC--
>CPU68421 1282 bp DNA.---------- ---------- ---------- ---------- ---------- ---------- ------T--- --C------G GT---T---T A:--AACC--
>CPU68458 1285 bp DNA.-------C-- ---------- ---------- ---------- ---------- ---------- ---------- --------T- --C--T---- ----------
>CPU68451 1284 bp DNA.---------- ---------- ---------- ---------- ---------- ---------- ---------- --------TG G-C------- ---T------
>CPU68423 1284 bp DNA.---------- ---------- ---------- ---------- ---------- ---------- ------T--- --C------- GT---T---T A:--AACC-C
>CPU68450 1284 bp DNA.---------- ---------- ---------- ---------- ---------- ---------- ---------- --------T- ---------- ----------
>CPU68459 1285 bp DNA.---------- ---------- ---------- ---------- ---------- ---------- ---------- --------T- --C--T---- ----------
 #501                 ....................................................................................................
                      TGATGACTGG GATGAAGTCG TAACAAGGTA GCCCTACCGG AAGGTGGGGC TGGATCACCT CCTTTT:AAG GATAAGGAAA ACTGTCT:TA GGACGGTT:T
                              **                                         *                       *      *     ** ********** **********
                                                                                                   165 ⊥ spacer

>CPU68419 2751 bp DNA.---------- -------G-- -------T-A ---------- ---------- ---------- --------:- ---------- ---T----:- ----:-----
>CTU68420 2762 bp DNA.---------- ---------- -A-ACG---G GG-GA-C--- -------A-- ---------- --:--A-C-: GAAG-GG--G -GA--TA--G --TA------
>CPU68432 1284 bp DNA.---------- ---------- ----G-C::- --G-:----- ---------- ---T------ --A--G---- --:GTT---- ---T------ ---A------
>CPU68454 1283 bp DNA.---------- -------G-- ---------- ---------- ---------- ---------- --T------- C-:------- ---T----:- ----:-----
>CPU68424 1284 bp DNA.---------- ------T--- ----A---T- ---C:-C--- ---------- ---------- --:------- --:------- ---------- -:-:------
>CPU68439 1284 bp DNA.---------- ---------- ----G-C::- --G-:----- ---------- ---T------ --A--G---- --:GTT---- ---T------ ---A------
>CTU68440 1304 bp DNA.---------- -------G-- -A-A-G---G AG-AA-C--- -------A-- --TG------ --A--A-GGC GGTG-GG--G -GA--TA--G --TG------
>CTU68428 1299 bp DNA.---------- ---------- -A-ACG---G AG-AA-C--- -------A-- ---------- --:--A-C-: GAAG-GG--G -GA--TA--G --TA------
>CPU68434 1284 bp DNA.---------- ---------- ----G-C::- --G-:----- ---------- ---T------ --A--G---- --:GTT---- ---T------ ---A------
>CPU68448 1283 bp DNA.---------- -------G-- ---------- ---------- ---------- ---------- --T------- C-:------- ---T----:- ----:-----
>CPU68459 1284 bp DNA.---------- ---------- ----G-C::- --G-:----- ---------- ---T------ --A--G---- --:GTT---- ---T------ ---A------
>CTU68442 1304 bp DNA.---------- ---------- -A-A-G---G AG-AA-C--- -------A-- --TG------ --A--A-CGC GGTG-GG--G -GA--TA--G --TG------
>CTU68437 1303 bp DNA.T--------- A--------- -A-A-G---G AG-AA-C--- -------A-- ---G------ --:--G-CGC GAAG-GG--G -AA--TAC-G --TG------
>CTU68441 1304 bp DNA.---------- -------G-- -A-A-G---G AG-AA-C--- -------A-- --TG------ --A--A-CGC GGTG-GG--G -GA--TA--G --TG------
>CPU68431 1284 bp DNA.---------- ---------- ----G-C::- --G-:----- ---------- ---T------ --A--G---- --:GTT---- ---T-T---- ---A------
>CTU68436 1303 bp DNA.T--------- A--------- -A-A-G---G AG-AG-C--- -------A-- ---G------ --:--G-CGC GAAG-GG--G -AA--TAC-G --TG------
>CTU68430 1302 bp DNA.---------- -------G-- -A-ACG---G AG-GG-C--- -------A-- ---------- --:--A-CG: GAAG-GG--G -GA--TA--G --TG------
>CTU68429 1298 bp DNA.---------- -C-------- -A-ACG---G GG-AA-C--- -------A-- ---------- --:--A-C-: GAAG-GG--G -GA--TA--G --TA------
>CTU68443 1304 bp DNA.---------- ---------- -A-A-G---G AG-AA-C--- -------A-- --TG------ --A--A-CG- GGTG-GG--G -GA--TA--G --TG------
>CPU68435 1284 bp DNA.---------- ---------- ----G-C::- --G-:----- ---------- ---T------ --A--G---- --:GTT----- ---T------ ---A------
>CTU68427 1299 bp DNA.---------- ---------- -A-ACG---G AG-GA-C--- -------A-- ---------- --:--A-C-: GAAG-GG--G -GA--TA--G --TA------
>CPU68445 1282 bp DNA.---------- ---------- ---------T :--------- ---------- ---------- --------:- ---------- ---T----:- ----:-----
>CPU68452 1284 bp DNA.---------- -------G-- -------T-A ---------- ---------- ---------- --------:- ---------- ---T----:- ----:-----
>CPU68444 1282 bp DNA.---------- ---------- ---------T :--------- ---------- ---------- --------:- ---------- ---T----:- ----:-----
>CPU68456 1284 bp DNA.---------- -------G-- -------T-A ---------- ---------- ---------- --------:- ---------- ---T----:- ----:-----
>CPU76710 1282 bp DNA.---------- ---------- ---------T :--------- ---------- ---------- --------:- ---------- ---T----:- ----:-----
>CPU68455 1284 bp DNA.---------- -------G-- -------T-A ---------- ---------- ---------- --------:- ---------- ---T----:- ----:-----
>CTU68438 1304 bp DNA.---------- -------G-- -A-A-G---G AG-AA-C--- -------A-- --TG------ --A--A-CGC GGTG-GG--G -GA--TA--G --TG------
>CPU68457 1285 bp DNA.---------- ---------- ------G--A A--------- ---------- ---G------ ----:--GG- -A-------- --------:- ----:-----
>CPU68446 1282 bp DNA.---------- ---------- ---------T :--------- ---------- ---------- --------:- ---------- ---T----:- ----:-----
>CPU68447 1284 bp DNA.---------- -------G-- -------T-A ---------- ---------- ---------- --------:- ---------- ---T----:- ----:-----
>CPU68449 1284 bp DNA.---------- -------G-- -------T-A ---------- ---------- ---------- --------:- ---------- ---T----:- ----:-----
>CPU68453 1283 bp DNA.---------- -------G-- -------:-A ---------- ---------- ---------- --T-----:- ---------- ---T----:- ----:-----
>CPU76711 1284 bp DNA.---------- ------T--- ----A---T- ---C:-C--- ---------- ---------- --:------- --:------- ---------- -:-:------
>CPU68422 1284 bp DNA.---------- ------T--- ----A---T- ---C:-C--- ---------- ---------- --:------- --:------- ---------- -:-:------
>CPU68426 1284 bp DNA.---------- ------T--- ----A--GT- ---C:-C--- ---------- ---------- --:------- --:------- ---------- -:-:------
>CPU68425 1284 bp DNA.---------- ------T--- ----A---T- ---C:-C--- ---------- ---------- --:------- --:------- ---------- -:-:------
```

TABLE I-continued

Alignment of Intergenic Spacers for 43 Chlamydia Strains

```
>CPU68421 1282 bp DNA.---------- ------T--- ----A---T- ---C:-C--- ---------- ---------- --:------- --:------- ---------- -:-:------
>CPU68458 1285 bp DNA.---------- ---------- ------G--A A--------- ---------- ---G------ ----:--GG- -A-------- --------:- ----:-----
>CPU68451 1284 bp DNA.---------- -------G-C ------G--A A--------- ---------- ---------- ----C-CG-- ---------- --------:- ----:-----
>CPU68423 1284 bp DNA.---------- ------T--- ----A---T- ---C:-C--- ---------- ---------- --:------- --:------- ---------- -:-:------
>CPU68450 1284 bp DNA.---------- -------G-- -------T-A ---------- ---------- ---------- --------:- ---------- ---T----:- ----:-----
>CPU68459 1285 bp DNA.---------- ---------- ------G--A A--------- ---------- ---G------ ----:--GG- -A-------- --------:- ----:-----
 #601                 .............................................................................................................
                      GACTAGGTTG GGCAAGCATT T:T:T:TTA: T:CTTGTATT CTATTTCTTT TGCATTGTTA AGCGTTGTTT TCCAAA:AC: ATTCAG:TA: TTACTGATCA
                      *          **    ** *  * ******* ***** *           *     **        * ****** *******  *  *** *****  ****

>CPU68419 2751 bp DNA.---------- ---------- ----:----- --------A- --:------- ---------- ---------- ---A------ ---------- ---------G
>CTU68420 2762 bp DNA.---------- ------GAAA :-:------- ---------- -------GC- ---------- ---------G ---T------ ---------- -:-:------
>CPU68432 1284 bp DNA.---------- ---------- ---------- ---------- ---T------ ---------- ---------- ---------- --:------- ---T------
>CPU68454 1283 bp DNA.---------- ---------- ----:----- --------A- --:------- ---------- ---------- ---A------ --------T- ----------
>CPU68424 1284 bp DNA.---------- ---------- ---------- ---------: ---T------ ---------- ---------- ---------- ---------- ----------
>CPU68439 1284 bp DNA.---------- ---------- ---------- ---------- ---T------ ---------- ---------- ---------- --:------- ---T------
>CTU68440 1304 bp DNA.---------- T-----GAAA ---------- ---------- -------GC- ---------- ---------G ---T------ -T-------- -:G:------
>CTU68428 1299 bp DNA.---------- ------GAAA :-:------- ---------- -------GC- ---------- ---------G ---T------ ---------- -:-:------
>CPU68434 1284 bp DNA.---------- ---------- ---------- ---------- ---T------ ---------- ---------- ---------- --:------- ----T-----
>CPU68448 1283 bp DNA.-T-------- ---------- ----:----- --------A- --:------- ---------- ---------- ---A------ --------T- ----------
>CTU68433 1284 bp DNA.---------- ---------- ---------- ---------- ---T------ ---------- ---------- ---------- --:------- ---T------
>CTU68442 1304 bp DNA.---------- T-----GAAA ---------- ---------- -------GC- ---------- ---------G ---T------ -T-------- -:G:------
>CTU68437 1303 bp DNA.---------- T-----GAAA ---------- ---------- A------GC- ---------- ---------G ---T------ ---------- -:-:------
>CTU68441 1304 bp DNA.---------- T-----GAAA ---------- ---------- -------GC- ---------- ---------G ---T------ -T-------- -:G:------
>CTU68431 1284 bp DNA.---------- ---------- ---------- ---------- ---T------ ---------- ---------- ---------- --:------- ---T------
>CTU68436 1303 bp DNA.---------- T-----GAAA ---------- ---------- A------GC- ---------- ---------G ---T------ ---------- -:-:------
>CTU68430 1302 bp DNA.---------- ------GAAA A--------- ---------- A------GC- ---------- ---------G ---T------ ---------- -:-:------
>CTU68429 1298 bp DNA.---------- ------GAAA :-:------- ---------- -------GC- ---------- ---------G ---T------ ---------- -:-:------
>CTU68443 1304 bp DNA.---------- T-----GAAA ---------- ---------- -------GC- ---------- ---------G ---T------ -T-------- -:G:------
>CPU68435 1284 bp DNA.---------- ---------- ---------- ---------- ---T------ --G------- ---------- ---------- --:------- ---T------
>CTU68427 1299 bp DNA.---------- ------GAAA :-:------- -----A--C- -------GC- ---------- ---------G ---T------ ---------- -:-:------
>CPU68445 1282 bp DNA.---------- ---------- ----:----- --------A- --:------- ---------- ---------- ---------- --:------- ----T-----
>CPU68452 1284 bp DNA.---------- ---------- ----:----- --------A- --:------- ---------- ---------- ---A------ --------T- ----------
>CPU68444 1282 bp DNA.---------- ---------- ----:----- --------A- --:------- ---------- ---------- ---------- --:------- ----T-----
>CPU68456 1284 bp DNA.---------- ---------- ----:----- --------A- --:------- ---------- ---------- ---A------ ---------- ----------
>CPU76710 1282 bp DNA.---------- ---------- ----:----- --------A- --:------- ---------- ---------- ---------- --:------- ----T-----
>CPU68455 1284 bp DNA.---------- ---------- ----:----- --------A- --:------- ---------- ---------- ---A------ ---------- ----------
>CTU68438 1304 bp DNA.---------- T-----GAAA ---------- ---------- -------GC- ---------- ---------G ---T------ -T-------- -:G:------
>CPU68457 1285 bp DNA.---------- ---------- ----:----- --------A- --:------- ---------- ---------- ---A------ ---------- ----------
>CPU68446 1282 bp DNA.---------- ---------- ----:----- --------A- --:------- ---------- ---------- ---------- --:------- ----T-----
>CPU68447 1284 bp DNA.---------- ---------- ----:----- --------A- --:------- ---------- ---------- ---A------ --------T- ----------
>CPU68449 1284 bp DNA.---------- ---------- ----:----- --------A- --:------- ---------- ---------- ---A------ ---------- ----------
>CPU68453 1283 bp DNA.---------- ---------- ----:----- --------A- --:------- ---------- ---------- ---A------ --------T- ----------
>CPU76711 1284 bp DNA.---------- ---------- ---------- ---------: ---T------ ---------- ---------- ---------- ---------- ----------
>CPU68422 1284 bp DNA.---------- ---------- ---------- ---------: ---T------ ---------- ---------- ---------- ---------- ----------
>CPU68426 1284 bp DNA.---------- ---------- ---------- ---------: ---T------ ---------- ---------- ---------- ---------- ----------
>CPU68425 1284 bp DNA.---------- ---------- ---------- ---------: ---T------ ---------- ---------- ---------- ---------- ----------
>CPU68421 1282 bp DNA.---------- ---------- ---------- ---------: ---T------ ---------- ---------- ---------- ---------- ----------
>CPU68458 1285 bp DNA.---------- ---------- ----:----- --------A- --:------- ---------- ---------- ---A------ ---------- ----------
>CPU68451 1284 bp DNA.---------- ---------- ----:----- --------A- --:------- ---------- ---------- ---------- --:------- ----------
```

TABLE I-continued

?

Alignment of Intergenic Spacers for 43 Chlamydia Strains

```
>CPU68423 1284 bp DNA.---------- ---------- ---------- ---------: ---T------ ---------- ---------- ---------- ---------- ----------
>CPU68450 1284 bp DNA.---------- ---------- ----:----- --------A- --:------- ---------- ---------- ---A------ ---------- ----------
>CPU68459 1285 bp DNA.---------- ---------- ----:----- --------A- --:------- ---------- ---------- ---A------ ---------- ----------
 #701                 ..............................................................................................................
                      AGTATGTTAT :GTAAA:::: TAATCATGGT AACAAGTATA TTT:CACATA TAATAATAGA CGTTTAAGAA TATCTGTCTT T:AGGTGAAG TTAACTTGCA
                       *         *     **** * * *           *  ** * **   **    *                 *    *        **     *   ****    *

>CPU68419 2751 bp DNA.---------- ---------- ---------- ---------- ---------- ---------- ---------- ---------- ---------- ----------
>CTU68420 2762 bp DNA.------T--G -G-AA----- ---------- GA-------- ---------- ---------- ---------- A------C-- -AA------- GAA--G--C-
>CPU68432 1284 bp DNA.--------A- ---------- ---------- -G-------- ---------- ---------- ---A------ ---------- ---------- -T--------
>CPU68454 1283 bp DNA.---------- ---------- ---------- ---------- ---------- ---------- ---------- ---------- ---------- ----------
>CPU68424 1284 bp DNA.--------A- ---------- ---------- G--------- -----C---- ---------- ---------- ---------- ---------- ----------
>CPU68439 1284 bp DNA.--------A- ---------- ---------- -G-------- ---------- ---------- ---A------ ---------- ---------- -T--------
>CTU68440 1304 bp DNA.------T--- -G-AA----- ---------- -A-------- ---------- ---------- ---------- A------C-- -AA------- GAA--G--C-
>CPU68428 1299 bp DNA.------T--G -G-AA----- ---------- GA-------- ---------- ---------- ---------- A------C-- -AA------- GAA--G--C-
>CPU68434 1284 bp DNA.--------A- ---------- ---------- -G-------- ---------- ---------- ---A------ ---------- ---------- -T--------
>CPU68448 1283 bp DNA.---------- ---------- ---------- ---------- ---------- ---------- ---------- ---------- ---------- ----------
>CPU68433 1284 bp DNA.--------A- ---------- ---------- -G-------- ---------- ---------- ---A------ ---------- ---------- -T--------
>CTU68442 1304 bp DNA.------T--- -G-AA----- ---------- -A-------- ---------- ---------- ---------- A------C-- -AA------- GAA--G--C-
>CTU68437 1303 bp DNA.------T--G ---AT----- ---------- GA-------- ---------- ---------- ---------- ---------- -AA------- GAA--G--C-
>CTU68441 1304 bp DNA.------T--- -G-AA----- ---------- -A-------- ---------- ---------- ---------- A------C-- -AA------- GAA--G--C-
>CPU68431 1284 bp DNA.--------A- ---------- ---------- -G-------- ---------- ---------- ---A------ ---------- ---------- -T--------
>CTU68436 1303 bp DNA.------T--G ---AT----- ---------- GA-------- ---------- ---------- ---------- -------C-- -AA------- GAA--G--C-
>CTU68430 1302 bp DNA.------T--G -G-AAA---- ---------- GA-------- ---------- ---------- ---------- A------C-- -AA------- GAA--G--C-
>CTU68429 1298 bp DNA.------T--G -G-AA----- ---------- GA-------- ---------- ---------- ---------- A------C-- -AA------- GAA--G--C-
>CPU68443 1304 bp DNA.------T--- -G-AA----- ---------- -A-------- ---------- ---------- ---------- A------C-- -AA------- GAA--G--C-
>CPU68435 1284 bp DNA.--------A- ---------- ---------- -G-------- ---------- ---------- ---A------ ---------- ---------- -T--------
>CPU68427 1299 bp DNA.------T--G -G-AA----- ---------- GA-------- ---------- ---------- ---------- A------C-- -AA------- GAA--G--C-
>CPU68445 1282 bp DNA.---------- ---------- ---------- ---------T ---------- ---------- ---------- ---------- ---------- ----------
>CPU68452 1284 bp DNA.---------- ---------- ---------- ---------- ---------- ---------- ---------- ---------- ---------- ----------
>CPU68444 1282 bp DNA.---------- ---------- ---------- ---------T ---------- ---------- ---------- ---------- ---------- ----------
>CPU68456 1284 bp DNA.---------- ---------- ---------- ---------- ---------- ---------- ---------- ---------- ---------- ----------
>CPU76710 1282 bp DNA.---------- ---------- ---------- ---------T ---------- ---------- ---------- ---------- ---------- ----------
>CPU68455 1284 bp DNA.---------- ---------- ---------- ---------- ---------- ---------- ---------- ---------- ---------- ----------
>CPU68438 1304 bp DNA.------T--- -G-AA----- ---------- -A-------- ---------- ---------- ---------- A------C-- AAA------- GAA--G--C-
>CPU68457 1285 bp DNA.---------- ---------- ---------- -G-------- -----C---- ---------- ---------- ---------- ---------- ----------
>CPU68446 1282 bp DNA.---------- ---------- ---------- --------T- ---------- ---------- ---------- ---------- ---------- ----------
>CPU68447 1284 bp DNA.---------- ---------- ---------- ---------- ---------- ---------- ---------- ---------- ---------- ----------
>CPU68449 1284 bp DNA.---------- ---------- ---------- ---------- ---------- ---------- ---------- ---------- ---------- ----------
>CPU68453 1283 bp DNA.---------- ---------- ---------- ---------- ---------- ---------- ---------- ---------- ---------- ----------
>CPU76711 1284 bp DNA.--------A- ---------- ---------- G--------- -----C---- ---------- ---------- ---------- ---------- ----------
>CPU68422 1284 bp DNA.--------A- ---------- ---------- G--------- -----C---- ------C--- ---------- ---------- ---------- ----------
>CPU68426 1284 bp DNA.--------A- ---------- ---------- G--------- -----C---- ---------- ---------- ---------- ---------- ----------
>CPU68425 1284 bp DNA.--------A- ---------- ---------- G--------- -----C---- ---------- ---------- ---------- ---------- ----------
>CPU68421 1282 bp DNA.--------A- ---------- ---------- G--------- -----C---- ---------- ---------- ---------- ---------- ----------
>CPU68458 1285 bp DNA.---------- ---------- ---------- -G-------- -----C---- ---------- ---------- ---------- ---------- ----------
>CPU68451 1284 bp DNA.---------- ---------- ---------- G--------- -----C---- ---------- ---------- ---------- ---------- ----------
>CPU68423 1284 bp DNA.--------A- ---------- ---------- G--------- -----C---- ---------- ---------- ---------- ---------- ----------
>CPU68450 1284 bp DNA.---------- ---------- ---------- ---------- ---------- ---------- ---------- ---------- ---------- ----------
>CPU68426 1284 bp DNA.---------- ---------- ---------- G--------- -----C---- ---------- ---------- ---------- ---------- ----------
```

TABLE I-continued

Alignment of Intergenic Spacers for 43 Chlamydia Strains

```
#801                      ....................................................................................................
                          TGGATCAAT: A:AT:T:TAC AGACCAAGTT ATTAAGAGCT ATTGGTGGAT GCCTTGGCAT TGACAGGCGA TGAAGGATGC GTTTACCTGC AGTAATCTTC
                                * **  * ****            **       *          *          *          *     *    ***          ***  *   *
                                   Spacer ⊥23S

>CPU68419 2751 bp DNA.---------- ---------- ---------- --C------- ---------- ---------- -CA----T-- -----C-T-- ---------- -G--------
>CTU68420 2762 bp DNA.---------- -GAT----A- C--------- ---------- ----A----- ------G--- ---------- --G---A--- --C------- T---C--A--
>CPU68432 1284 bp DNA.---------- ---------- ---------- --T------- ---AA----- -A-------- -------T-- -----C---- ---C------ -G--------
>CPU68454 1283 bp DNA.---------- ---------- ---------- --C------- ---------- ---------- -CA------- -----C-T-- ---------- -G--------
>CPU68424 1284 bp DNA.--T------- ----G----- ---------- ---------- ---------- -A----C--- -------T-- -------T-- ---------- ----------
>CPU68439 1284 bp DNA.---------- ---------- ---------- --T------- ---AA----- -A-------- -------T-- -----C---- ---C------ -G--------
>CTU68440 1304 bp DNA.---------- -GAT----A- A--------- ---------- ----A----- ------G--- ---A------ --GC------ ---------- T--GC--A--
>CPU68428 1299 bp DNA.---------- -GAT----A- C--------- ---------- ----A----- ------G--- ---------- --G---A--- --C------- T---C--A--
>CPU68434 1284 bp DNA.---------- ---------- ---------- --T------- ---AA----- -A-------- -------T-- -----C---- ---C------ -G--------
>CPU68448 1283 bp DNA.---------- ---------- ---------- --C------- ---------- ---------- -CA------- -----C-T-- ---------- -G--------
>CPU68433 1284 bp DNA.---------- ---------- ---------- --T------- ---AA----- -A-------- -------T-- -----C---- ---C------ -G--------
>CTU68442 1304 bp DNA.---------- -GAT----A- A--------- ---------- ----A----- ------G--- ---A------ --GC------ ---------- T--GC--A--
>CTU68437 1303 bp DNA.---------- --AT----A- A--------- --G------- ----A----- ------G--- ---------- --G---A--- ---------- T--GC--A--
>CTU68441 1304 bp DNA.---------- -GAT----A- A--------- ---------- ----A----- ------G--- ---A------ --GC------ ---------- T--GC--A--
>CPU68431 1284 bp DNA.---------- ---------- ---------- --T------- ---AA----- -A-------- -------T-- -----C---- ---C------ -G--------
>CTU68436 1303 bp DNA.---------- --AT----A- A--------- --G------- ----A----- ------G--- ---------- --G---A--- ---------- T--GC--A--
>CPU68430 1302 bp DNA.---------- -GAT----A- A--------- ---------- ----G----- ------G--- ---A------ --G------- --C------- ----C--A--
>CPU68429 1298 bp DNA.---------- -GAT----A- C--------- ---------- ----A----- ------G--- ---------- --G---A--- --C------- T---C--A--
>CPU68443 1304 bp DNA.---------- -GAT----A- A--------- ---------- ----A----- ---------- ---------- --GC------ ---------- T--GC--A--
>CPU68435 1284 bp DNA.---------- ---------- ---------- --T------- ---AA----- -A-------- -------T-- -----C---- ---C------ -G--------
>CPU68427 1299 bp DNA.---------- -GAT----A- C--------- ---------- ----A----- ------G--- ---------- --G---A--- --C------- T---C--A--
>CPU68445 1282 bp DNA.---------- ---------- ---------- --C------- ---------- -A-------- -CA----T-- --G--C---- ---------- -G--------
>CPU68452 1284 bp DNA.---------- ---------G ---------- --C------- ---------- ---------- -CA------- -----C-T-- ---------- -G--------
>CPU68444 1282 bp DNA.---------- ---------- ---------- --C------- ---------- -A-------- -CA----T-- --G--C---- ---------- -G--------
>CPU68456 1284 bp DNA.---------- ---------- ---------- --C------- ---------- ---------- -CA------- -----C-T-- ---------A -G--------
>CPU76710 1282 bp DNA.---------- ---------- ---------- --C------- ---------- -A-------- -CA----T-- --G--C---- ---------- -G--------
>CPU68455 1284 bp DNA.---------- ---------- ---------- --C------- ---------- ---------- -CA------- -----C-T-- ---------A -G--------
>CTU68438 1284 bp DNA.---------- -GAT----A- A--------- ---------- ----A----- ------G--- ---A------ --GC------ ---------- T--GC--A--
>CPU68457 1285 bp DNA.---------- ---------- ---------- --C------- ---------- ---------- -CA------- ---------- ---------- -------A--
>CPU68446 1282 bp DNA.---------- ---------- ---------- --C------- ---------- -A-------- -CA----T-- --G--C---- ---------- -G--------
>CPU68447 1284 bp DNA.---------- ---------- ---------- --C------- ---------- ---------- -CA------- -----C-T-- ---------- -G--------
>CPU68449 1284 bp DNA.---------- ---------- ---------- --C------- ---------- ---------- -CA------- -----C-T-- ---------A -G--------
>CPU68453 1283 bp DNA.---------- ---------- ---------- --C------- ---------- ---------- -CA------- -----C-T-- ---------- -G--------
>CPU76711 1284 bp DNA.--T------- ----G----- ---------- ---------- ---------- -A----C--- -------T-- -------T-- ---------- ----------
>CPU68422 1284 bp DNA.--T------- ----G----- ---------- ---------- ---------- -A----C--- -------T-- -------T-- ---------- ----------
>CPU68426 1284 bp DNA.--T------- ----G----- ---------- ---------- ---------- -A----C--- -------T-- ---------- ---------- ----------
>CPU68425 1284 bp DNA.--T------- ----G----- ---------- ---------- ---------- -A----C--- -------T-- -------T-- ---------- ----------
>CPU68421 1282 bp DNA.--T------- ----G----- ---------- ---------- ---------- -A----C--- -------T-- -------T-- ---------- ----------
>CPU68458 1285 bp DNA.---------- ---------- ---------- --C------- ---------- ---------- -CA------- ---------- ---------- -------A--
>CPU68451 1284 bp DNA.---------- ---------- ---------- ---------- ----T----- ---------- -C-------- ------A--- ---------- T------A--
>CPU68423 1284 bp DNA.--T------- ----G----- ---------- ---------- ---------- -A----C--- -----C-T-- -------T-- ---------- ----------
>CPU68450 1284 bp DNA.---------- ---------- ---------- --C------- ---------- ---------- -CA------- -----C-T-- ---------A -G--------
>CPU68459 1285 bp DNA.---------- ---------- ---------- --C------- ---------- ---------- -CA------- ---------- ---------- -------A--
#901                      ....................................................................................................
                          GGCGAGCTGG TATAAAGCTA TGACCCGGAG GTATCCGAAT GGGGCAACCC GGTAGATTAA TAGTCTACCA TTATATGCTG AATACATAGG CATATAAGGC
```

TABLE I-continued

Alignment of Intergenic Spacers for 43 Chlamydia Strains

```
                       *         ****   ** *            *           **       *    *     *** * *      ** ***     **     * ** **  *
                     Region A←

>CPU68419 2751 bp DNA.---------- ---------- ---------- ---------- -T-------- ---------- AA-------- ---------- ---G---A-C -----G----
>CTU68420 2762 bp DNA.---------C ---------- ---------- ---------- -------G-- -------T-- ---------- ---------- ----G----- -----GAGC-
>CPU68432 1284 bp DNA.--A----A-- ---------- ---------- -T-------- ---------- ---------- ---------- ---------- ----C--T-- ------T---
>CPU68454 1283 bp DNA.---------- ---------- ---------- ---------- -T-------- ---------- AA-------- --------A- ---G---A-C ----------
>CPU68424 1284 bp DNA.------C--- ---------- ---------- --G------- ---------- ---------- ---------- ---------- ----C----- ------T---
>CPU68439 1284 bp DNA.--A----A-- ---------- ---------- -T-------- ---------- ---------- ---------- ---------- ----C--T-- ------T---
>CTU68440 1304 bp DNA.---------C ---------- ---------- ---------- -------G-- ---------- ---------- ---------- ----T----- -----GAGC-
>CTU68428 1299 bp DNA.---------C ---------- ---------- ---------- -------G-- ---------- ---------- ---------- ----G----- -----GAGC-
>CPU68434 1284 bp DNA.--A----A-- ---------- ---------- -T-------- ---------- ---------- ---------- ---------- ----C--T-- ------T---
>CPU68448 1283 bp DNA.---------- ---------- ---------- ---------- -T-------- ---------- AA-------- --------A- ---G---A-C ----------
>CPU68433 1284 bp DNA.--A----A-- ---------- ---------- -T-------- ---------- ---------- ---------- ---------- ----C--T-- ------T---
>CTU68442 1304 bp DNA.---------C ---------- ---------- ---------- -------G-- ---------- ---------- ---------- ----T----- -----GAGC-
>CTU68437 1303 bp DNA.A--------- ---------- ---------- ---------- -------G-- ---------- ---------- ---------- ----G----- -----GA-C-
>CTU68441 1304 bp DNA.---------C ---------- ---------- ---------- -------G-- ---------- ---------- ---------- ----T----- -----GAGC-
>CPU68431 1284 bp DNA.--A----A-- ---------- ---------- -T-------- ---------- ---------- ---------- ---------- ----C--T-- ------T---
>CTU68436 1303 bp DNA.A--------- ---------- ---------- ---------- -------G-- ---------- ---------- ---------- ----G----- -----GA-C-
>CTU68430 1302 bp DNA.---------C ---------- ---------- ---------- -------G-- ---------- ---------- ---------- ----G----- -----GAGC-
>CTU68429 1298 bp DNA.---------C ---------- ---------- ---------- -------G-- ---------- ---------- ---------- ----G----- -----GAGC-
>CTU68443 1304 bp DNA.---------C ---------- ---------- ---------- -------G-- ---------- ---------- ---------- ----T----- -----GAGC-
>CPU68435 1284 bp DNA.--A----A-- ---------- ---------- -T-------- ---------- ---------- ---------- ---------- ----C--T-- ------T---
>CTU68427 1299 bp DNA.---------C ---------- ---------- ---------- -------G-- ---------- ---------- ---------- ----G----- -----GAGCC
>CPU68445 1282 bp DNA.--T------- ---------- ---------- ---------- -T-------- ---------- -A-------- ---------- ---G---A-C ----------
>CPU68452 1284 bp DNA.---------- ---------- ---------- ---------- -T-------- ---------- AA-------- ---------- ---G---A-C ----------
>CPU68444 1282 bp DNA.--T------- ---------- ---------- ---------- -T-------- ---------- -A-------- ---------- ---G---A-C ----------
>CPU68456 1284 bp DNA.---------- ---------- ---------- ---------- -T-------- ---------- -A-------- ---------- ---G---A-C ----------
>CPU76710 1282 bp DNA.--T------- ---------- ---------- ---------- -T-------- ---------- -A-------- ---------- ---G---A-C ----------
>CPU68455 1285 bp DNA.---------- ---------- ---------- ---------- -T-------- ---------- -A-------- ---------- ---G---A-C ----------
>CTU68438 1304 bp DNA.---------C ---------- ---------- ---------- -------G-- ---------- ---------- ---------- ----T----- -----GAGC-
>CPU68457 1285 bp DNA.---------- ---------- ---------- ---------- ---------- ---------- -A-------- ---------- ---TT--A-C -------G--
>CPU68446 1282 bp DNA.--T------- ---------- ---------- ---------- -T-------- ---------- -A-------- ---------- ---G---A-C ----------
>CPU68447 1284 bp DNA.---------- ---------- ---------- ---------- -T-------- ---------- AA-------- ---------- ---G---A-C ----------
>CPU68449 1284 bp DNA.---------- ---------- ---------- ---------- -T-------- ---------- -A-------- ---------- ---G---A-C ----------
>CPU68453 1283 bp DNA.---------- ---------- ---------- ---------- -T-------- ---------- AA-------- --------A- ---G---A-C ----------
>CPU76711 1284 bp DNA.------C--- ---------- ---------- --G------- ---------- ---------- ---------- ---------- ----C----- ------T---
>CPU68422 1284 bp DNA.------C--- ---------- ---------- --G------- ---------- ---------- ---------- ---------- ----C----- ------T---
>CPU68426 1284 bp DNA.------C-T- ---------- ---------- --G------- ---------- ---------- ---------- ---------- ----C----- ------T---
>CPU68425 1284 bp DNA.------C--- ---------- ---------- --G------- ---------- ---------- ---------- ---------- ----C----- ------T---
>CPU68421 1282 bp DNA.------C--- ---------- ---------- --G------- ---------- ---------- ---------- ---------- ----C----- ------T---
>CPU68458 1285 bp DNA.---------- ---------- ---------- ---------- ---------- ---------- -A-------- ---------- ---TT--A-C -------G--
>CPU68451 1284 bp DNA.---------- ---------- ---------- ---------- -T-------- ---------- AA-------- ---------- ---G---A-C -------GCC
>CPU68423 1284 bp DNA.------C--- ---------- ---------- --G------- ---------- ---------- ---------- ---------- ----C----- ------T---
>CPU68450 1284 bp DNA.---------- ---------- ---------- ---------- -T-------- ---------- -A-------- ---------- ---G---A-C ----------
>CPU68459 1285 bp DNA.--------A- ---------- ---------- ---------- ---------- ---------- -A-------- ---------- ---TT--A-C -------G--
 #1001                ..............................................................................................................
                      GACACCTGCT GAACTGAAAC ATCTTAGTAA GCAGAGGAAA AGAAATCAAA GAGATTCCCT GTGTAGCGGC GAGCGAAAGG GGAAAGCCT AAACCACATTC
                      * *   ****                        **         *     *          *   **                 *      **  * *      *****
```

TABLE I-continued

Alignment of Intergenic Spacers for 43 Chlamydia Strains

```
>CPU68419 2751 bp DNA.---------- ---------- ---------- ---------- ---------- ---------- --------A- ---------- ---------- ----------
>CTU68420 2762 bp DNA.GAAG-A-CGA ---------- ---T--GG-A -AA-----AG G-C-CC---- ----C--A-- -------G-- G-T------- ---------- ----------
>CPU68432 1284 bp DNA.------A--- ---------- ---------- G--A------ ---------- ------T--- ---------- ---------- ---------- -----A----
>CPU68454 1283 bp DNA.---------- ---------- ---------- ---------- ---------- ---------- -------CA- ---------- ---------- ----------
>CPU68424 1284 bp DNA.------A--- ---------- ---------- ---------- ---------- ---------- ---------- ---------- ---------- -----A----
>CPU68439 1284 bp DNA.------A--- ---------- ---------- G--A------ ---------- ------T--- ---------- ---------- ---------- -----A----
>CTU68440 1304 bp DNA.GA---G-C-C ---------- -A-T--GG-T -AA-----AG G-C-CC---- ----C--A-- -------A-- G-T------- ---------- ----------
>CTU68428 1299 bp DNA.GAAG-A-CGA ---------- ---T--GG-A -AA-----AG G-C-CC---- ----C--A-- -------G-- G-T------- ---------- ----------
>CPU68434 1284 bp DNA.------A--- ---------- ---------- G--A------ ---------- ------T--- ---------- ---------- ---------- -----A----
>CPU68448 1283 bp DNA.---------- ---------- ---------- ---------- ---------- ---------- -------CA- ---------- ---------- ----------
>CPU68433 1284 bp DNA.------A--- ---------- ---------- G--A------ ---------- ------T--- ---------- ---------- ------G--- -----A----
>CTU68442 1304 bp DNA.GA---GTC-C ---------- -A-T-GGG-T -AA-----AG --C-CC---- ----C--A-- -------A-- G-T------- ---------- ----------
>CTU68437 1303 bp DNA.-A-:-GT--C ---------- -A-T-GGG-T -AA-----AA G-T-CC---- ----C--A-- -------G-- G-T--A---- ---------- ----------
>CTU68441 1304 bp DNA.GA---G-C-C ---------- -A-T-GGG-T ---------- ---------- ----C--A-- -------A-- G-T------- ---------- ----------
>CPU68431 1284 bp DNA.------A--- ---------- ---------- G--A------ ---------- ------T--- ---------- ---------- ---------- -----A----
>CTU68436 1303 bp DNA.-A-:-GT--C ---------- -A-T-GGG-T -AA-----AA G-T-CC---- ----C--A-- -------G-- G-T--A---- ---------- ----------
>CTU68430 1285 bp DNA.GAAG-A-CGA ---------- ---T--GGGA GAA-----AG G-C-CC---- ----C--A-- -------G-- G-T------- ---------- ----------
>CTU68429 1298 bp DNA.GAAG-A-CGA ---------- ---T--GG-A -AA-----AG G-C-CC---- ----C--A-- -------G-- G-T------- ---------- ----------
>CTU68443 1304 bp DNA.GA---G-C-C ---------- -A-T--GG-T -AA-----AG G-C-CC---- ----C--A-- -------A-- G-T------- ---------- ----------
>CPU68435 1284 bp DNA.------A--- ---------- ---------- G--A------ ---------- ------T--- ---------- ---------- ---------- -----A----
>CTU68427 1299 bp DNA.GAAG-A-CGA ---------- ---T--GG-A -AA-----AG G-C-CC---- ----C--A-- -------G-- G-T------- ---------- ----------
>CPU68445 1282 bp DNA.---------- ---------- ---------- ---------- ---------- C--------- --------A- ---------- ---------- ----------
>CPU68452 1284 bp DNA.---------- ---------- ---------- ---------- ---------- ---------- --------A- ---------- ---------- ----------
>CPU68444 1282 bp DNA.---------- ---------- ---------- ---------- ---------- C--------- --------A- ---------- ---------- ----------
>CPU68456 1284 bp DNA.---------- ---------- ---------- ---------- ---------- ---------- --------A- ---------- ---------- ----------
>CPU76710 1282 bp DNA.---------- ---------- ---------- ---------- ---------- C--------- --------A- ---------- ---------- ----------
>CPU68455 1284 bp DNA.---------- ---------- ---------- ---------- ---------- ---------- --------A- ---------- ---------- ----------
>CTU68438 1304 bp DNA.GA---G-C-C ---------- -A-T--GG-T -AA-----AG G-C-CC---- ----C--A-- -------A-- G-T------- ---------- ----------
>CPU68457 1285 bp DNA.---------- ---------- ---------- ---------- ---------- ---------- --------A- -----C---- ---------- -----A----
>CPU68446 1282 bp DNA.---------- ---------- ---------- ---------- ---------- C--------- --------A- ---------- ---------- ----------
>CPU68447 1284 bp DNA.---------- ---------- ---------- ---------- ---------- ---------- --------A- ---------- ---------- ----------
>CPU68449 1284 bp DNA.---------- ---------- ---------- ---------- ---------- ---------- --------A- ---------- ---------- ----------
>CPU68453 1283 bp DNA.---------- ---------- ---------- ---------- ---------- ---------- -------CA- ---------- ---------- ----------
>CPU76711 1284 bp DNA.------A--- ---------- ---------- ---------- ---------- ---------- ---------- ---------- ---------- -----A----
>CPU68422 1284 bp DNA.------A--- ---------- ------C--- ---------- ---------- ---------- ---------- ---------- ---------- -----A----
>CPU68426 1284 bp DNA.------A--- ---------- ---------- ---------- ---------- ---------- ---------- ---------- ---------- -----A----
>CPU68425 1284 bp DNA.------A--- ---------- ---------- ---------- ---------- ---------- ---------- ---------- ---------- -----A----
>CPU68421 1282 bp DNA.------A--- ---------- ---------- ---------- ---------- ---------- ---------- ---------- ---------- -----A----
>CPU68458 1285 bp DNA.---------- ---------- ---------- ---------- ---------- ---------- --------A- -----C---- ---------- -----A----
>CPU68451 1284 bp DNA.---GG----- ---------- ---------- ---A------ ---------- ---------- --------A- ---------- ---------- -----A----
>CPU68423 1284 bp DNA.------A--- ---------- ---------- ---------- ---------- ---------- ---------- ---------- ---------- ----TA----
>CPU68450 1284 bp DNA.---------- ---------- ---------- ---------- ---------- ---------- --------A- ---------- ---------- ----------
>CPU68459 1285 bp DNA.---------- ---------- ---------- ---------- ---------- ---------- --------A- -----C---- ---------- -----A----
 #1101                .............................................................................................................
                      TTTAATG:T: GGGGTTGTAG GGTCGATAAC ATGGGATCTT AAGTTTTAGT TGAATACTTC TGGAAAGTTG AACGATACAG GGTGATAGTC CCGTAGACGA
                      **********             * * ***** ****    ** * * **     *   * **          **  * *  *          *        **

>CPU68419 2751 bp DNA.---------G ---------- ---------- ---------- ---------- ---------- ---------- ---------- ---T------ ----------
>CTU68420 2762 bp DNA.--GG-G-G-- -----GACC- -A-------- -----A---- ---------- ---------- ---------- ---------- ---------- ----------
>CPU68432 1284 bp DNA.---------- ---------- ----T----- ----AA---- ---------G ------T--- ---------- ---------- ---A------ ----A-----
```

TABLE I-continued

Alignment of Intergenic Spacers for 43 Chlamydia Strains

```
>CPU68454 1283 bp DNA.---------G ---------- ---------- ---------- ---------- ---------- ---------- ---------- ---T------ ----------
>CPU68424 1284 bp DNA.---------- ----G---A- ---------- ---------- ---------- ---------- ---------- ---------- ---------- ----------
>CPU68439 1284 bp DNA.---------- ---------- ----T----- ----AA---- ---------- ------T--- ---------- ---------- ---A------ ----A-----
>CTU68440 1304 bp DNA.--GG-G-G-- ----CGACC- -A-C------ -----A---- ---------- T--------- ---------- ---------- ---------- ----------
>CTU68428 1299 bp DNA.--GG-G-G-- ----CGACC- -A-------- -----A---- ---------- ---------- ---------- ---------- ---------- ----------
>CPU68434 1284 bp DNA.---------- ---------- ----T----- ----AA---- ---------- ------T--- ---------- ---------- ---A------ ----A-----
>CPU68448 1283 bp DNA.---------G ---------- ---------- ---------- ---------- ---------- ---------- ---------- ---T------ ----------
>CPU68433 1284 bp DNA.---------- ---------- ----T----- ----AA---- ---------- ------T--- ---------- ---------- ---A------ ----A-----
>CTU68442 1304 bp DNA.--GG-G-G-- ----CGACC- -A-C------ -----A---- ---------- ---------- ---------- ---------- ---------- ----------
>CTU68437 1303 bp DNA.--GG-G-TC- ----CGACC- -A-C------ ---------- ---------- ---------- ---------- ---------- ---------- ----------
>CTU68441 1304 bp DNA.--GG-G-G-- ----CGACC- -A-C------ -----A---- ---------- ---------- ---------- ---------- ---------- ----------
>CPU68431 1284 bp DNA.---------- ---------- ----T----- ----AA---- ---------- ------T--- ---------- ---------- ---A------ ----A-----
>CTU68436 1303 bp DNA.--GG-G-TC- ----CGACC- -A-C------ ---------- ---------- ---------- ---------- ---------- ---------- ----------
>CTU68430 1302 bp DNA.--GG-G-G-T ----CGACC- ---------- ---------- ---------- ---------- ---------- ---------- ---------- ----------
>CTU68429 1298 bp DNA.--GG-G-G-- ----CGACC- -A-------- -----A---- ---------- ---------- ---------- ---------- ---------- ----------
>CTU68443 1304 bp DNA.--GG-G-G-- ----CGACC- -A-C------ -----A---- ---------- ---------- ---------- ---------- ---------- ----------
>CPU68435 1284 bp DNA.---------- ---------- ----T----- ----AA---- ---------- ------T--- ---------- ---------- ---A------ ----A-----
>CTU68427 1299 bp DNA.--GG-G-G-- ----CGACC- -A-------- -----A---- ---------- ---------- ---------- ---------- ---------- ----------
>CPU68445 1282 bp DNA.---------G ---------- ---------- ---------- ---------- ---------- ---------- ---------- ---T------ ----------
>CPU68452 1284 bp DNA.---------G ---------- ---------- ---------- ---------- ---------- ---------- ---------- ---T------ ----------
>CPU68444 1282 bp DNA.---------G ---------- ---------- ---------- ---------- ---------- ---------- ---------- ---T------ ----------
>CPU68456 1284 bp DNA.---------G ---------- ---------- ---------- ---------- ---------- ---------- ---------- ---T------ ----------
>CPU76710 1282 bp DNA.---------G ---------- ---------- ---------- ---------- ---------- ---------- ---------- ---T------ ----------
>CPU68455 1284 bp DNA.---------G ---------- ---------- ---------- ---------- ---------- ---------- ---------- ---T------ ----------
>CTU68438 1304 bp DNA.--GG-G-G-- ----CGACC- -A-C------ -----A---- ---------- ---------- ---------- ---------- ---------- ----------
>CPU68457 1285 bp DNA.---------G ---------- ---------- ---------- ---------- ---------- ---------- ---------- ---T------ ----------
>CPU68446 1282 bp DNA.---------G ---------- ---------- ---------- ---------- ---------- ---------- ---------- ---T------ ----------
>CPU68447 1284 bp DNA.---------G ---------- ---------- ---------- ---------- ---------- ---------- ---------- ---T------ ----------
>CPU68449 1284 bp DNA.---------G ---------- ---------- ---------- ---------- ---------- ---------- ---------- ---T------ ----------
>CPU68453 1283 bp DNA.---------G ---------- ---------- ---------- ---------- ---------- ---------- ---------- ---T------ ----------
>CPU76711 1284 bp DNA.---------- ----G---A- ---------- ---------- ---------- ---------- ---------- ---------- ---------- ----------
>CPU68422 1284 bp DNA.---------- ----G---A- ---------- ---------- ---------- ---------- ---------- ---------- ---------- ----------
>CPU68426 1284 bp DNA.---------- --G-A---A- ---------- ---------- ---------- ---------- ---------- ---------T ---------- ----------
>CPU68445 1282 bp DNA.---------- ----G---A- ---------- ---------- ---------- ---------- ---------- ---------- ---------- ----------
>CPU68445 1282 bp DNA.---------- ----G---A- ---------- ---------- ---------- ---------- ---------- ---------- ---------- ----------
>CPU68458 1285 bp DNA.---------G ---------- ---------- ---------- ---------- ---------- ---------- ---------- ---T------ ----------
>CPU68451 1284 bp DNA.--G------G ---------- ----G----- ---------- ---------- ---------- ---------- ---------- ---T------ ----------
>CPU68423 1284 bp DNA.---------- ----G---A- ---------- ---------- ---------- ---------- ---------- ---------- ---------- ----------
>CPU68450 1284 bp DNA.---------G ---------- ---------- ---------- ---------- ---------- ---------- ---------- ---T------ ----------
>CPU68459 1285 bp DNA.---------G ---------- ---------- ---------- ---------- ---------- ---------- ---------- ---T------ ----------
 #1201                ...........................................................................................................
                      AAAAACA:AA AGACTCTATT CGATACCTGA GTAGGGCTAG ACACGTGAAA CCTAGTCTGA ATCTGGGGAG ACCACTCTCC AAGGCTAAAT ACTAGTCAAT
                        ** * ***   * *****   * **        **              * *     *                         *    *           *

>CPU68419 2751 bp DNA.---------- ---------- ---------- ---------- ---------- ---------- ---------- ---------- ---------- ----------
>CTU68420 2762 bp DNA.----G----- ---------- ---------- ---C------ ---------- ---------- ---------- -------A-- -----C---- -----G----
>CPU68432 1284 bp DNA.---------- --------C- ---A------ ---------- ---------- ---------- ---------- ---------- ---------- ----------
>CPU68454 1283 bp DNA.---------- ---------- ---------- ---------- ---------- ---------- ---------- ---------- ---------- ----------
>CPU68424 1284 bp DNA.---------- ---------- ---------- ---------- ---------- ---------- ---------- ---------- ---------- -----G----
>CPU68439 1284 bp DNA.---------- ---------- ---A------ ---------- ---------- ---------- ---------- ---------- ---------- ----------
```

TABLE I-continued

Alignment of Intergenic Spacers for 43 Chlamydia Strains

```
>CTU68440 1304 bp DNA.----G----- ---------- ---------- ---C------ ---------- ---------- ---------- ---------- -----C---- -----G----
>CTU68428 1299 bp DNA.----G----- ---------- ---------- ---C------ ---------- ---------- ---------- -------A-- -----C---- -----G----
>CPU68434 1284 bp DNA.---------- ---------- ---A------ ---------- ---------- ---------- ---------- ---------- ---------- ----------
>CPU68448 1283 bp DNA.---------- ---------- ---------- ---------- ---------- ---------- ---------- ---------- ---------- ----------
>CPU68433 1284 bp DNA.---------- ---------- ---A------ ---------- ---------- ---------- ---------- ---------- ---------- ----------
>CTU68442 1304 bp DNA.----G----- ---------- ---------- ---C------ ---------- ---------- ---------- ---------- -----C---- -----G----
>CTU68437 1303 bp DNA.----G----- ---------- ---------- ---C------ ---------- ---------- ---------- ---------- -----C---- ----------
>CTU68441 1304 bp DNA.----G----- ---------- ---------- ---C------ ---------- ---------- ---------- ---------- -----C---- -----G----
>CPU68431 1284 bp DNA.---------- ---------- ---A------ ---------- ---------- ---------- ---------- ---------- ---------- ----------
>CTU68436 1303 bp DNA.----G----- ---------- ---------- ---C------ ---------- ---------- ---------- ---------- -----C---- ----------
>CTU68430 1302 bp DNA.----G----- ---------- ---------- ---C------ ---------- ---------- ---------- ---------- -----C---- -----G----
>CTU68429 1298 bp DNA.----G----- ---------- ---------- ---C------ ---------- ---------- ---------- -------A-- -----C---- -----G----
>CTU68443 1304 bp DNA.----G----- ---------- ---------- ---C------ ---------- ---------- ---------- ---------- -----C---- -----G----
>CPU68435 1284 bp DNA.---------- ---------- ---A------ ---------- ---------- ---------- ---------- ---------- ---------- ----------
>CTU68427 1299 bp DNA.----G----- ---------- ---------- ---C------ ---------- ---------- ---------- ---------- -----C---- -----G----
>CPU68445 1282 bp DNA.---------- ---------- ---------- ---------- ---------- ---------- ---------- ---------- ---------- ------G---
>CPU68452 1284 bp DNA.---------- ---------- ---------- ---------- ---------- ---------- ---------- ---------- ---------- ----------
>CPU68444 1282 bp DNA.---------- ---------- ---------- ---------- ---------- ---------- ---------- ---------- ---------- ----------
>CPU68456 1284 bp DNA.---------- ---------- -----G---- ---------- ---------- ---------- ---------- ---------- ---------- ----------
>CPU76710 1282 bp DNA.---------- ---------- ---------- ---------- ---------- ---------- ---------- ---------- ---------- ----------
>CPU68455 1284 bp DNA.---------- ---------- ---------- ---------- ---------- ---------- ---------- ---------- ---------- ----------
>CTU68438 1304 bp DNA.----G----- ---------- ---------- ---C------ ---------- ---------- ---------- ---------- -----C---- -----G----
>CPU68457 1285 bp DNA.---------- ---------- ---------- ---------- ---------- ---------- ---------- -------A-- ---------- ----------
>CPU68446 1282 bp DNA.---------- ---------- ---------- ---------- ---------- ---------- ---------- ---------- ---------- ----------
>CPU68447 1284 bp DNA.---------- ---------- ---------- ---------- ---------- ---------- ---------- ---------- ---------- ----------
>CPU68449 1284 bp DNA.---------- ---------- ---------- ---------- ---------- ---------- ---------- ---------- ---------- ----------
>CTU68453 1283 bp DNA.---------- ---------- ---------- ---------- ---------- ---------- ---------- ---------- ---------- ----------
>CTU76711 1284 bp DNA.---------- ---------- ---------- ---------- ---------- ---------- ---------- ---------- ---------- -----G----
>CPU68422 1284 bp DNA.---------- ---------- ---------- ---------- ---------- ---------- ---------- ---------- ---------- -----G----
>CPU68426 1284 bp DNA.---------- ---------- ---------- ---------- ---------- ---------- ---------- ---------- ---------- -----G----
>CPU68425 1284 bp DNA.---------- ---------- ---------- ---------- ---------- ---------- ---------- ---------- ---------- -----G----
>CPU68421 1282 bp DNA.---------- ---------- ---------- ---------- ---------- ---------- ---------- ---------- ---------- -----G----
>CPU68458 1285 bp DNA.---------- ---------- ---------- ---------- ---------- ---------- ---------- -------A-- ---------- ----------
>CPU68451 1284 bp DNA.---------- ---------- ---------- ---------- ---------- ---------- ---------- ---------- ---------- -----G----
>CPU68423 1284 bp DNA.---------- ---------- ---------- ---------- ---------- -------C-- ---------- ---------- ---------- -----G----
>CPU68450 1284 bp DNA.---------- ---------- ---------- ---------- ---------- ---------- ---------- ---------- ---------- ----------
>CPU68459 1285 bp DNA.---------- ---------- ---------- ---------- ---------- ---------- ---------- -------A-- ---------- ----------
 #1301                ...........................................................................................................
                      GACCTATAGT GAACCAGTAC TGTGAAGGAA AGGTGAAAAG AACCCTTGTT AAGGGAGTGA AATAGAACCT GAAACCAGTA GCTTATAAGC GGTCGAAGAC
                          *               *    * *         *                          *                        *         *         **
                                                         →Region B>

>CPU68419 2751 bp DNA.---------- ---------- ---------- ---------- ---------- ---------- ---------- ---------- -------C-- ----------
>CTU68459 2762 bp DNA.----GGC-CG T:A-:-GGT- :-A------- ---------- ---------- ---------- -----C---- ---------- -------G-- ----------
>CPU68432 1284 bp DNA.---------: ---C---:-- G--------- ---------- ---------- ---------- ---------- ---------- ---------- ----------
>CPU68454 1283 bp DNA.---------- ---------- ---------- ---------- ---------- ---------- ---------- ---------- ---------- ----------
>CPU68424 1284 bp DNA.---------: ---C---:-- A--------- ---------- ---------- ---------- ---------- -------A-- ---------- ----------
>CPU68439 1284 bp DNA.---------: ---C---:-- G--------- ---------- ---------- ---------- ---------- ---------- ---------- ----------
>CTU68440 1304 bp DNA.-A--GGC-CG T:A-:-GG:- --A------- ---------- ---------- ---------- -----C---- ---------- -------A-- ----------
>CTU68428 1299 bp DNA.----GGC-CG T:A-:-GGT- :-A------- ---------- ---------- ---------- -----C---- ---------- -------G-- ----------
```

TABLE I-continued

Alignment of Intergenic Spacers for 43 Chlamydia Strains

```
>CPU68434 1284 bp DNA.---------: ---C---:-- G--------- ---------- ---------- ---------- ---------- ---------- ---------- ----------
>CPU68448 1283 bp DNA.---------- ---------- ---------- ---------- ---------- ---------- ---------- ---------- ---------- ----------
>CPU68433 1284 bp DNA.---------: ---C------ G--------- ---------- ---------- ---------- ---------- ---------- ---------- ----------
>CTU68442 1304 bp DNA.-A--GGC-CG T:A-:-GG:- --A------- ---------- ---------- ---------- -----C---- ---------- -------A-- ----------
>CTU68437 1303 bp DNA.----GTC-C- T-A-C-GG-- -GA------- ---------- ---------- ---------- -----C---- ---------- -------G-- ----------
>CTU68441 1304 bp DNA.-A--GGC-CG T:A-:-GG:- --A------- ---------- ---------- ---------- -----C---- ---------- -------A-- ----------
>CPU68431 1284 bp DNA.---------: ---C---:-- G--------- ---------- ---------- ---------- ---------- ---------- ---------- ----------
>CTU68436 1303 bp DNA.----GTC-C- T-A-C-GG-- -GA------- ---------- ---------- ---------- -----C---- ---------- -------G-- ----------
>CTU68430 1302 bp DNA.----GGC-CG -:A-:-GG:- T-A------- ---------- ---------- ---------- -----C---- ---------- -------G-- -----T----
>CTU68429 1298 bp DNA.----GGC-CG T:A-:-GGT- :-A------- ---------- ---------- -------:-- -----C---- ---------- -------G-- ----------
>CTU68443 1304 bp DNA.-A--GGC-CG T:A-:-GG:- --A------- ---------- ---------- ---------- -----C---- ---------- -------A-- ----------
>CPU68435 1284 bp DNA.---------: ---C---:-- G--------- ---------- ---------- ---------- ---------- ---------- ---------- ----------
>CTU68427 1299 bp DNA.---CGGC-CG -:A-:-GGT- :-A------- ---------- ---------- ---------- -----C---- ---------- -------G-- -----T----
>CPU68445 1282 bp DNA.---------- ---C------ ---------- ---------- ---------- ---------- ---------- ---------- -------C-- ----------
>CPU68452 1284 bp DNA.---------- ---------- ---------- ---------- ---------- ---------- ---------- ---------- ---------- ----------
>CPU68444 1282 bp DNA.---------- ---C------ ---------- ---------- ---------- ---------- ---------- ---------- -------C-- ----------
>CPU68456 1285 bp DNA.---------- ---------- ---------- ---------- ---------- ---------- ---------- ---------- -------C-- ----------
>CPU76710 1282 bp DNA.---------- ---C------ ---------- ---------- ---------- ---------- ---------- ---------- -------C-- ----------
>CPU68455 1284 bp DNA.---------- ---------- ---------- ---------- ---------- ---------- ---------- ---------- -------C-- ----------
>CTU68438 1304 bp DNA.-A--GGC-CG T:A-:-GG:- --A------- ---------- ---------- ---------- -----C---- ---------- -------A-- ----------
>CPU68457 1285 bp DNA.----T-G--- T--C-A---C A--------- ---------- ---------- ---------- ---------- ---------- ---------- ----------
>CPU68446 1282 bp DNA.---------- ---C------ ---------- ---------- ---------- ---------- ---------- ---------- -------C-- ----------
>CPU68447 1284 bp DNA.---------- ---------- ---------- ---------- ---------- ---------- ---------- ---------- ---------- ----------
>CPU68449 1284 bp DNA.---------- ---------- ---------- ---------- ---------- ---------- ---------- ---------- -------C-- ----------
>CPU68453 1283 bp DNA.---------- ---------- ---------- ---------- ---------- ---------- ---------- ---------- ---------- ----------
>CPU76711 1284 bp DNA.---------: ---C---:-- A--------- ---------- ---------- ---------- ---------- -------A-- ---------- ----------
>CPU68422 1284 bp DNA.---------: ---C---:-- A--------- ---------- ---------- ---------- ---------- -------A-- ---------- ----------
>CPU68426 1284 bp DNA.---------: ---C---:-- A--------- ---------- ---------- ---------- ---------- -------A-- ---------- ----------
>CPU68425 1284 bp DNA.---------: ---C---:-- A--------- ---------- ---------- ---------- ---------- -------A-- ---------- ----------
>CPU68421 1282 bp DNA.---------: ---C---:-- A--------- ---------- ---------- ---------- ---------- -------A-- ---------- ----------
>CPU68458 1285 bp DNA.----T-G--- T--C-A---C A--------- ---------- ---------- ---------- ---------- ---------- ---------- ----------
>CPU68451 1284 bp DNA.----:-G--- -C-C-----C ---------- ---------- ---------- ---------- ---------- ---------- -------C-- ----------
>CPU68423 1284 bp DNA.---------: ---C---:-- A--------- ---------- ---------- ---------- ---------- -----G-A-- ---------- ----------
>CPU68450 1284 bp DNA.---------- ---------- ---------- ---------- ---------- ---------- ---------- ---------- -------C-- ----------
>CPU68459 1285 bp DNA.----T-G--- T--C-A---C A--------- ---------- ---------- ---------- ---------- ---------- ---------- ----------
 #1401                .............................................................................................................
                      CTATAA:CTT CTTAGGAAGT CATGGTTGAC GGCGTGCCTT TTGCATGATG AGCCAGGGAG TTAAGTTAAA CGGCGAGGTT AAGGGATTTA CATTCCGGAG
                       * **** ** ********** ***                                     *          *          * *          *          *
                                                                                  Region B ←

>CPU68419 2751 bp DNA.---------- ---------- ---------- ---------- ---------- ---------- ---------- ---------- ---------- --------C-
>CTU68420 2762 bp DNA.---------- ---------- ---------- ---------- --G------- ---------- ---------- ---------- ---------- -----A---A
>CPU68432 1284 bp DNA.---------- ---------- ---------- ---------- ---------- ---------- ----T----- ---------- ---------T ----------
>CPU68454 1283 bp DNA.---------- ---------- ---------- ---------- ---------- ---------- ---------- ---------- ---------- --------CA
>CPU68424 1284 bp DNA.T--------- ---------- ---------- --T------- ---------- ---------- ---------- ---------- ---------T ----------
>CPU68439 1284 bp DNA.---------- ---------- ---------- ---------- ---------- ---------- ----T----- ---------- ---------T ----------
>CTU68440 1304 bp DNA.---G------ ---------- ---------A AG-------- --G------- ---------- ---------- ---------- ---------- -----A---A
>CTU68428 1299 bp DNA.---------- ---------- ---------- ---------- --G------- ---------- ---------- ---------- ---------- -----A---A
>CPU68434 1284 bp DNA.---------- ---------- ---------- ---------- ---------- ---------- ----T----- ---------- ---------T ----------
>CPU68448 1283 bp DNA.---------- ---------- ---------- ---------- ---------- ---------- ---------- ---------- ---------- --------CA
```

TABLE I-continued

?

Alignment of Intergenic Spacers for 43 Chlamydia Strains

```
>CPU68433 1284 bp DNA.---------- ---------- ---------- ---------- ---------- ---------- ----T----- ---------- ---------T ----------
>CTU68442 1304 bp DNA.---G------ ---------- ---------A AG-------- --G------- ---------- ---------- ---------- ---------- -----A---A
>CTU68437 1303 bp DNA.---------- ---------- ---------- ---------- --G------- ---------- ---------- ---------- ---------- -----A---A
>CTU68441 1304 bp DNA.---G------ ---------- ---------A AG-------- --G------- ---------- ---------- ---------- ---------- -----A---A
>CPU68431 1284 bp DNA.---------- ---------- ---------- ---------- ---------- ---------- ----T----- ---------- ---------T ----------
>CTU68436 1303 bp DNA.---------- ---------- ---------- ---------- --G------- ---------- ---------- ---------- ---------- -----A---A
>CTU68430 1302 bp DNA.---G------ ---------- ---------- A--------- --G------- ---------- ---------- ---------- ---------- -----A---A
>CTU68429 1298 bp DNA.---------- ---------- ---------- ---------- --G------- ---------- ---------- ---------- ---------- -----A---A
>CTU68443 1304 bp DNA.---G------ ---------- ---------A AG-------- --G------- ---------- ---------- ---------- ---------- -----A---A
>CPU68435 1284 bp DNA.---------- ---------- ---------- ---------- ---------- ---------- ----T----- ---------- ---------T ----------
>CTU68427 1299 bp DNA.---G------ ---------- ---------- A--------- --G------- ---------- ---------- ---------- ---------- -----A---A
>CPU68445 1282 bp DNA.---------- ---------- ---------- ---------- ---------- ---------- ---------- ---------- ---------- --------C-
>CPU68452 1284 bp DNA.---------- --T------- ---------- ---------- ---------- ---------- ---------- ---------- ---------- --------C-
>CPU68444 1282 bp DNA.---------- ---------- ---------- ---------- ---------- ---------- ---------- ---------- ---------- ---T----C-
>CPU68456 1284 bp DNA.---------- ---------- ---------- ---------- ---------- ---------- ---------- ---------- ---------- --------C-
>CPU76710 1282 bp DNA.---------- ---------- ---------- ---------- ---------- ---------- ---------- ---------- ---------- --------C-
>CPU68455 1284 bp DNA.---------- ---------- ---------- ---------- ---------- ---------- ---------- ---------- ---------- ----------
>CTU68438 1304 bp DNA.---G------ ---------- ---------A AG-------- --G------- ---------- ---------- ---------- ---------- -----A---A
>CPU68457 1285 bp DNA.---------- ---------- --T------- ---------- -A-------- ---------- ---------- ---------- -------G-- --------C-
>CPU68446 1282 bp DNA.---------- ---------- ---------- ---------- ---------- ---------- ---------- ---------- ---------- --------C-
>CPU68447 1284 bp DNA.---------- ---------- ---------- ---------- ---------- ---------- ---------- ---------- ---------- --------C-
>CPU68449 1284 bp DNA.---------- ---------- ---------- ---------- ---------- ---------- ---------- ---------- ---------- --------C-
>CPU68453 1283 bp DNA.---------- ---------- ---------- ---------- ---------- ---------- ---------- ---------- ---------- --------CA
>CPU76711 1284 bp DNA.T--------- ---------- ---------- --T------- ---------- ---------- ---------- ---------- ---------T ----------
>CPU68422 1284 bp DNA.T--------- ---------- ---------- --T------- ---------- ---------- ---------- ---------- ---------T ----------
>CPU68426 1284 bp DNA.T--------- ---------- ---------- --T------- ---------- ---------- ---------- ---------- --A------T ----------
>CPU68425 1284 bp DNA.T--------- ---------- ---------- --T------- ---------- ---------- ---------- ---------- ---------T ----------
>CPU68421 1282 bp DNA.T--------- ---------- ---------- --T------- ---------- ---------- ---------- ---------- ---------T ----------
>CPU68458 1285 bp DNA.---------- ---------- --T------- ---------- ---------- ---------- ---------- ---------- -------G-- --------C-
>CPU68451 1284 bp DNA.---------- ---------- --T------- A--------- ---------- ---------- ---------- ---------- ---------- --------C-
>CPU68423 1284 bp DNA.T--------- ---------- ---------- --T------- ---------- ---------- ---------- ---------- ---------T ----------
>CPU68450 1284 bp DNA.---------- ---------- ---------- ---------- ---------- ---------- ---------- ---------- ---------- --------C-
>CPU68459 1285 bp DNA.---------- ---------- --T------- ---------- ---------- ---------- ---------- ---------- -------G-- --------C-
 #1501                .............................................................................................................
                      CCGAAGCGAA AGCGAGTTTT AAAAGAGCGT TT:AGTCGTT TGATTTAGAC ACGAAACCAA GTGAGCTATT TATGACCAGG TTGAAGCATG GGTAAGACTT
                      *  *         *           *      * ***         **                       *                   *    * *    * *  **

>CPU68419 2751 bp DNA.---------- ---------- ---------- ---------- ---------- ---------- ---------- ---------- ---------- ----------
>CTU68420 2762 bp DNA.---------- -----T---- -C-------- --G------- ---------- ---------- ---------- ---------- ---------- ----------
>CPU68432 1284 bp DNA.---------- -----T---- -C-------- --G------- ---------- ------:--- ---
>CPU68454 1283 bp DNA.---------- ---------- ---------- ---------- ---------- ---------- ---
>CPU68424 1284 bp DNA.---------- ---------- ---------- ---------- ---------- ---------- ---
>CPU68439 1284 bp DNA.---------- -----T---- -C-------- --G------- ---------- ------:--- ---
>CTU68440 1304 bp DNA.---------- -----T---- -C-------- --G------- ---------- ---------- ---
>CTU68428 1299 bp DNA.---------- -----T---- -C-------- --G------- ---------- ---------- ---
>CPU68434 1284 bp DNA.---------- -----T---- -C-------- --G------- ---------- ------:--- ---
>CPU68448 1283 bp DNA.---------- ---------- ---------- ---------- ---------- ---------- ---
>CPU68432 1284 bp DNA.---------- -----T---- -C-------- --G------- ---------- ------:--- ---
>CTU68442 1304 bp DNA.---------- -----T---- -C-------- --G------- ---------- ---------- ---
>CTU68437 1303 bp DNA.---------- ---------- -C-------- --G------- ---A------ ---------- ---
```

TABLE I-continued

Alignment of Intergenic Spacers for 43 Chlamydia Strains

```
>CTU68441 1304 bp DNA.---------- -----T---- -C-------- --G------- ---------- ---------- ---
>CPU68431 1284 bp DNA.---------- -----T---- -C-------- --G------- ---------- ------:--- ---
>CTU68436 1303 bp DNA.---------- ---------- -C-------- --G------- ---------- ---------- ---
>CTU68430 1302 bp DNA.---------- -----T---- -C-------- --G------- ---------- ---------- ---
>CTU68429 1298 bp DNA.---------- -----T---- -C-------- --G------- ---------- ---------- ---
>CTU68443 1304 bp DNA.---------- -----T---- -C-------- --G------- ---------- ---------- ---
>CPU68435 1284 bp DNA.---------- -----T---- -C-------- --G------- ---------- ------:--- ---
>CTU68427 1299 bp DNA.---------- -----T---- -C-------- --G------- ---------- ---------- ---
>CPU68445 1282 bp DNA.---------- ---------- ---------- -----C---- ---------- -------C-- ---
>CPU68452 1284 bp DNA.---------- ---------- ---------- ---------- ---------- ---------- ---
>CPU68444 1282 bp DNA.---------- ---------- ---------- ---------- ---------- ---------- ---
>CPU68456 1284 bp DNA.---------- ---------- ---------- ---------- ---------- ---------- ---
>CPU76710 1282 bp DNA.---------- ---------- ---------- ---------- ---------- ---------- ---
>CPU68455 1284 bp DNA.---------- ---------- ---------- ---------- ---------- ---------- ---
>CTU68438 1304 bp DNA.---------- -----T---- -C-------- --G------- ---------- ---------- ---
>CPU68457 1285 bp DNA.---------- ---------- ---------- ---------- ---------- ---------- ---
>CPU68446 1282 bp DNA.---------- ---------- ---------- ---------- ---------- ---------- ---
>CPU68447 1284 bp DNA.---------- ---------- ---------- ---------- ---------- ---------- ---
>CPU68449 1284 bp DNA.---------- ---------- ---------- ---------- ---------- ---------- ---
>CPU68447 1284 bp DNA.---------- ---------- ---------- ---------- ---------- ---------- ---
>CPU68449 1284 bp DNA.---------- ---------- ---------- ---------- ---------- ---------- ---
>CPU68453 1283 bp DNA.---------- ---------- ---------- ---------- -------C-- ---------- ---
>CPU76711 1284 bp DNA.---------- ---------- ---------- ---------- ---------- ---------- ---
>CPU68422 1284 bp DNA.---------- ---------- ---------- ---------- ---------- ---------- ---
>CPU68426 1284 bp DNA.---------- ---------- ---------- ---------- ---------- ---------- ---
>CPU68425 1284 bp DNA.---------- ---------- ---------- ---------- ---------- ---------- ---
>CPU68458 1285 bp DNA.---------- ---------- ---------- ---------- ---------- ---------- ---
>CPU68451 1284 bp DNA.---------- ---------- ---------- ---------- ---------- ---------- ---
>CPU68423 1284 bp DNA.---------- ---------- ---------- ---------- ---------- ---------- ---
>CPU68450 1284 bp DNA.---------- ---------- ---------- ---------- ---------- ---------- ---
>CPU68459 1285 bp DNA.---------- ---------- ---------- ---------- ---------- ---------- ---
 #1601                .............................................................................................................
                      TGTGGAGGAC CGAACCAGTA CATGTTGAAA AATGTTTGGA TGAGTTGTGA ATAGGGGTGA AAGGCCAATC AAACTTGGAG ATATCTTGTT CTCTCCGAAA
                                       *      *           *  *        *   *         **

>CPU68419 2751 bp DNA.-----T---- ---------- ----T----- ---------- ---------- ---------- ---------- ---------A ---------- ----------
>CTU68420 2762 bp DNA.-----A---- ---------- ----A----- ---------- ---------- ---------- ---------- ---------C ---------- ----------
 #1701                .............................................................................................................
                      TAACTWTAGG GTTAGCCTCG GATAWTAAGC TTTTGGGGGT AGAGCACTGA ATTCTAGCGG GGGCCTACCG GCTTACCAAM GGAAATCAAA CTCCGAATAC
                           *                    *                                                            *

>CPU68419 2751 bp DNA.--A---T--- ---------- ---------- ---------- ---------- ------A--- ---------- ---------- ---A------ ----------
>CTU68420 2762 bp DNA.--G---C--- ---------- ---------- ---------- ---------- ------G--- ---------- ---------- ---T------ ----------
 #1801                .............................................................................................................
                      CARAAGYGAG TCCGGGAGAT AGACAGCGGG GGCTAAGCTT CGTTGTCGAG AGGGGARCAG CCCAGACCGC CGATTAAGGT CCCWAATTTT ATGCTAAGTG
                         *   *                                                 *                              *

>CPU68419 2751 bp DNA.---------- ---------T ---------- ---------- ---------- ---------- ---------- ---------- ---------- ----------
>CTU68420 2762 bp DNA.---------- ---------A ---------- ---------- ---------- ---------- ---------- ---------- ---------- ----------
 #1901                .............................................................................................................
```

TABLE I-continued

Alignment of Intergenic Spacers for 43 Chlamydia Strains

```
                      AGTAAGGAAG TGATGATTCW AAGACAGTTG GAATGTTGGC TTAGAGGCAG CAATCATTTA AAGAGTGCGT AACAGCTCAC CAATCGAGAA TCATTGCGCC
                                          *

>CPU68419 2751 bp DNA.A-------T- ---------- ---------- -A-------- ---A-AT-T- TAT------- ---------- ---------- ----T----- -A-----T--
>CTU68420 2762 bp DNA.G-------A- ------:--- ---------- -C-------- ---G-CG-A- GGC-::---- ---------- ---------- ----A----- -G-----A--
 #2001                .............................................................................................................
                      RATAATAAWC GGGGCTCAAG CATAAAACCG AMATCGCGGG TGTRTMKTWA KRYATACGCG GTAGGAGAGC GTAGTATTCA GCAGWGAAGG TRTACCGWAA
                      *       *        *                *            * ** *  ***  **                                *       *     *

>CPU68419 2751 bp DNA.----T----- ---------- ---------- ---------- ---------- ---A------ -----T---- ---------A ---------- ----------
>CTU68420 2762 bp DNA.----C----- ---------- ---------- ---------- ---------- ---G------ -----C---- ---------C ---------- ----------
 #2101                .............................................................................................................
                      GGAGYGCTGG AGCGGATACT AGTGAAGATC CATGGCATAA GTAACGATAA AGGRAGTGAA AATCTYCCTC GCCGTAARCM CAAGGTTTCC AGGGTCAAGC
                         *                                                     *            *              *

>CPU68419 2751 bp DNA.---------- ---------- ---------- -C-----AC- -A-------- ---------- A--------- --------T- --------A- --T----A-T
>CTU68420 2762 bp DNA.---------- ---------- ---------- -T-----GT- -C-------- ---------- G--------- --------C- --------G- --A----G-A
 #2201                .............................................................................................................
                      TCGTCTTCCC TGGGTTAGTC GGCCCCTAAG TYGAGGCRYA AMTGCGTAGA CGATGGAGCA RCAGGTTAAA TATTCCTGYA CCACCTAARA CTWTAGCRAW
                                                        *    **   *                    *                  *          *    *    * *

>CPU68419 2751 bp DNA.---------- ----C----- ---------- --------A- -------TCA -A------C- ---------- ---------- ----T---G- T----T-T-G
>CTU68420 2762 bp DNA.---------- ----A----- ---------- --------G- -------GAG -G------A- ---------- ---------- ----G---A- C----C-C-A
 #2301                .............................................................................................................
                      GGAATGACGG AGTAMGTTAA GCACGCGGAC GATTGGAART GTCCGTAKMR CRATGAGAMC GGTTAGTAGG CAAATCCGCT AACAKAAGRT YAGGTYGYGR
                                     *                        *         *                            *   *  *    * * *

>CPU68419 2751 bp DNA.-T-----A-- ---------- ---T---A-- ---GC--A-- ---------- ---------- ---------- ---------- --T------- --------T-
>CTU68420 2762 bp DNA.-C-----G-- ---------- ---C---G-- ---TA--G-- ---------- ---------- ---------- ---------- --A------- --------G-
 #2401                .............................................................................................................
                      TYAAGGGRAA TCTTCGGAGG AACYGATRGT GTGKMGCRAG GCTTTCAAGA AATAATTTCT AGCTGTTGAT GGTGACCGTA CCWAAACCGA CACAGGTGKG
                       *     *                 *   *      **  *                                                 *                *

>CPU68419 2751 bp DNA.---------- ---------- ---------- ---------- ---------- ---------- ---------- --A-G----- ------C--- ------T-GC
>CTU68420 2762 bp DNA.---------- ---------- ---------- ---------- ---------- ---------- ---------- --G-T----- ------T--- ------C-AT
 #2501                .............................................................................................................
                      CGAGATGAGT ATTCTAAGGC GCGCGAGATA ACTTTCGTTA AGGAACTCGG CAAATTATCC CCGTAACTTC GGRAKAAGGG GAGCCTYTTA GGGTGAYTRY
                                                                                             * *            *          * **

>CPU68419 2751 bp DNA.CTT----GC- T----T---- ---------- ---------- ---------- ----A----- ---------- ---------- -T-------- ----------
>CTU68420 2762 bp DNA.GGA:---AT- G----C---- ---------- ---------- ---------- ----G----- ---------- ---------- -G-------- ----------
 #2601                .............................................................................................................
                      SKWTACGRYA KGAGCYCCGG GGGGCCGCAG AGAAATGGCC CAGGCGACTG TTTARCAAAA ACACAGCACT ATGCAAACCT CKAAGGGGAA GTATATGGTG
                      ****   **  *    *                                          *                             *

>CPU68419 2751 bp DNA.---------- ---------- ---------- ---------- --C----G-- A--------- ---C------ ---------- ---------- ----------
>CTU68420 2762 bp DNA.---------- ---------- ---------- ---------- --T----A-- G--------- ---T------ ---------- ---------- ----------
 #2701                .............................................................................................................
                      TGACGCCTGC CCAATGCCAA AAGGTTAAAG GGATATGTCA GCYGCAARGC RAAGCATTGA ACCYAAGCCC TGGTGAATGG CCGCC
```

TABLE I-continued

| Alignment of Intergenic Spacers for 43 Chlamydia Strains |
|---|
| * * * * |

?

TABLE IA

| Concordance of Chlamydia Accessions and SEQ ID NOs | |
|---|---|
| CPU68419 | SEQ ID NO 6 |
| CTU68420 | SEQ ID NO 37 |
| CPU68432 | SEQ ID NO 20 |
| CPU68454 | SEQ ID NO 3 |
| CPU68424 | SEQ ID NO 28 |
| CPU68439 | SEQ ID NO 24 |
| CTU68440 | SEQ ID NO 33 |
| CTU68428 | SEQ ID NO 38 |
| CPU68434 | SEQ ID NO 22 |
| CPU68448 | SEQ ID NO 1 |
| CPU68433 | SEQ ID NO 21 |
| CTU68442 | SEQ ID NO 35 |
| CTU68437 | SEQ ID NO 43 |
| CTU68441 | SEQ ID NO 34 |
| CPU68431 | SEQ ID NO 19 |
| CTU68436 | SEQ ID NO 42 |
| CTU68430 | SEQ ID NO 41 |
| CTU68429 | SEQ ID NO 39 |
| CTU68443 | SEQ ID NO 36 |
| CPU68435 | SEQ ID NO 23 |
| CTU68427 | SEQ ID NO 40 |
| CPU68445 | SEQ ID NO 13 |
| CPU68452 | SEQ ID NO 5 |
| CPU68444 | SEQ ID NO 12 |
| CPU68456 | SEQ ID NO 10 |
| CPU76710 | SEQ ID NO 11 |
| CPU68455 | SEQ ID NO 9 |
| CTU68438 | SEQ ID NO 32 |
| CPU68457 | SEQ ID NO 15 |
| CPU68446 | SEQ ID NO 14 |
| CPU68447 | SEQ ID NO 4 |
| CPU68449 | SEQ ID NO 7 |
| CPU68453 | SEQ ID NO 2 |
| CPU76711 | SEQ ID NO 31 |
| CPU68422 | SEQ ID NO 26 |

TABLE IA-continued

| Concordance of Chlamydia Accessions and SEQ ID NOs | |
|---|---|
| CPU68426 | SEQ ID NO 30 |
| CPU68425 | SEQ ID NO 29 |
| CPU68421 | SEQ ID NO 25 |
| CPU68458 | SEQ ID NO 16 |
| CPU68451 | SEQ ID NO 18 |
| CPU68423 | SEQ ID NO 27 |
| CPU68450 | SEQ ID NO 8 |
| CPU68459 | SEQ ID NO 17 |

TABLE II

Strains, Hosts, Sources, aud Origins

| Strain[a] | Source[b] | Serovar | Apparent Host | Site of Isolation | Associated Disease(s) | Geographic Origin | Date[c] |
|---|---|---|---|---|---|---|---|
| *Chlamydia psittaci* | | | | | | | |
| CP3(VR 574) | NADC | B | pigeon | air sacs | systemic | California | 1958 |
| MN(VR 122) | NADC | E | (epizootic)human | throat washings | systemic | California | 1934/6 |
| MN Zhang | Caldwell | E | (epizootic)human | throat washings | systemic | California | 1934/6 |
| $6BC^T$(VR $125^T$) | NADC | A | parakeet | — | systemic | California | 1941 |
| M56 | NADC | M56 | (epizootic)muskrat/hare | blood, spleen | systemic | Canada | 1961 |
| NJI | NADC | D | turkey | muscle | systemic | New Jersey | 1954 |
| CT1 | NADC | C | turkey | — | systemic | California | 1954 |
| GD | NADC | C | duck | eggs | systemic | Germany | 1960 |
| Parl | Storey | | partridge | nasal discharge | — | North England | 1983 |
| WC | NADC | WC | (epizootic)cattle | intestine | enteritis | California | 1963 |
| EBA | NADC | | | | | | |
| A22 | Herring | I1 | sheep | fetal membranes | abortion | Scotland | 1949 |
| B577(VR 656) | NADC | I1 | sheep | fetal kidney | abortion | Idaho | 1962 |
| OSP | NADC | I1 | sheep | placenta | abortion | Oregon | 1985 |
| FP(VR 120) | NADC | I7 | feline | lung, upper respiratory | pneumonitis, rhinitis | Baker, New Jersey | 1944 |
| FP Cello | NVSL | I7 | feline | conjunctiva, upper respiratory | conjunctivitis, rhinitis | California | 1967 |
| FP Vaccine | Solvay | I7 | feline | — | vaccine strain | Baker(Solvay) | |
| GPIC(VR 813) | NADC | I8 | guinea pig | conjunctiva | conjunctivitis | Massachusetts | 1964 |
| *Chlamydia pecorum* | | | | | | | |
| 1710S | Kaltenboeck | I6 | swine | fetus | abortion | Austria | 1960's |
| BP-1 | NADC | BP1 | cattle | nasal discharge | respiratory, acute | Wisconsin | 1961 |
| $E58^T$(VR $628^T$) | NADC | I2 | cattle | brain | encephalomyelitis | Iowa | 1940 |
| IPA | NADC | I2 | sheep | joint fluid | polyarthritis | Iowa | 1968 |
| L71 | Herring | I4 | swine | joints | polyarthritis | Austria | 1960's |
| Z | NADC | Z | cattle | nasal discharge | respiratory, chronic | Minnesota | 1972 |
| *Chlamydia pneumoniae* | | | | | | | |

TABLE II-continued

Strains, Hosts, Sources, and Origins

| Strain[a] | Source[b] | Serovar | Apparent Host | Site of Isolation | Associated Disease(s) | Geographic Origin | Date[c] |
|---|---|---|---|---|---|---|---|
| CM-1 | Black | | human | sputum | pneumonia | Atlanta | 1990 |
| CWL-029 | Black | | human | throat | pneumonia | Atlanta | 1987 |
| CWL-1011 | Black | | human | throat | pneumonia | Atlanta | 1987 |
| FML-12 | Black | | human | throat | pneumonia | Norway | 1989 |
| FML-16 | Black | | | | | | |
| N16 | Storey | | horse | nasal discharge | upper respiratory | Great Britain | 1990 |
| TW-183[T] | Campbell | | human | conjunctiva | pneumonia | Taiwan | 1965 |
| *Chlamydia trachomatis*[d] | | | | | | | |
| A/Har-13[T] | Caldwell | A | human | conjunctiva | conjunctivitis | Egypt | 1958 |
| B/TW-5/OT | Caldwell | B | human | conjunctiva | conjunctivitis | Taiwan | 1959 |
| D/UW-3/CX | Caldwell | D | human | cervix | STD | USA | 1967 |
| F/IC/CAL3 | Caldwell | F | human | cervix | STD | USA | 1962 |
| L2/434/BU | Caldwell | LGV | human | lymph nodes | lymphogranuloma | USA | 1967 |
| R22 | NADC | Gp1 | swine | conjunctiva | conjunctivitis | Nebraska | 1992 |
| R24 | NADC | Gp2 | swine | nasal mucosa | upper respiratory | Nebraska | 1992 |
| R27 | NADC | Gp4 | swine | colon | enteritis | Nebraska | 1993 |
| H5 | NADC | Gp5 | swine | conjunctiva | conjunctivitis | Iowa | 1994 |
| S45 | Kaltenboeck | 15 | swine | feces | asymtomatic | Austria | 1960's |
| MoPn(VR 123) | Caldwell | | mouse | lung | pneumonitis | Minnesota | 1942 |
| SFPD Fox | | | hamster | intestine | proliferative iletis | — | 1991 |

[a]Strain M56 is a yolk sac passage of the original preparation and is not VR 630, the isolate available from ATCC. VR 630 is a mixed culture which in Vero cells grow out as strain M56 and in McCoy host cells grows out as FP(4)[e]. CT1 is sometimes referred to as C1. Strain FML-16 was identical to TW-183[T]. Strain EBA was identical to A22 and OSP. Serovars are generally host or disease specific; established serovars are indicated with letters, as immunotypes (I), or as groups (Gp).

[b]NADC: Avian and Swine Respiratory Diseases Research Unit, USDA, Agricultural Research Service, National Animal Disease Center, Ames, IA; Caldwell, H. D. Caldwell; Herring, A. J. Herring; NVSL, Diagnostic Virology Laboratory, National Veterinary Services Laboratory, Animal and Plant Health Inspection Service, USDA, Ames, IA; Solvay, Solvay Animal Health, Inc. Mendota Heights, MN; Kaltenboeck, B. Kaltenboeck: Black, C. M. Black; Campbell, L. A. Campbell; Fox, J. G. Fox; Kahane, S. Kahane.

[c]The dates are dates of isolation or earliest publication.

[d]Strains R22, R24, and R27 were isolated from multiple sites associated with respiratory disease, conjunctivitis, and enteritis, STD, sexually transmitted disease.

[T]Type strain for this species.

TABLE III

Order: Chlamydiales
Family I: Chlamydiaceae:

| proposed species | clade | current species |
|---|---|---|
| *Chlamydia muridarum* | mouse/hamster | *Chlamydia trachomatis* |
| *Chlamydia suis* | swine, trachomatis-like | *Chlamydia trachomatis* |
| *Chlamydia trachomatis* | human trachoma/STD | *Chlamydia trachomatis* |
| *Chlamydophila abortus* | mammalian abortion | *Chlamydia psittaci* |
| *Chlamydophila caviae* | guinea pig | *Chlamydia psittaci* |
| *Chlamydophila felis* | feline pneumonitis | *Chlamydia psittaci* |
| *Chlamydophila pecorum* | ruminant | *Chlamydia pecorum* |
| *Chlamydophila pneumoniae* | human pneumonia | *Chlamydia pneumoniae* |
| *Chlamydophila psittaci* | avian psittacosis | *Chlamydia psittaci* |

TABLE IV

| Strain | Accession No. | SEQ ID No. | Map Position for Region A | Map Position for Region B |
|---|---|---|---|---|
| *C. psittaci* CP3 (VR 574) | U68448 | 1 | 1–535 | 957–1086 |
| *C. psittaci* MN (VR 122) | U68453 | 2 | 1–535 | 957–1086 |
| *C. psittaci* MN Zhang | U68454 | 3 | 1–535 | 957–1086 |
| *C. psittaci* 6BC (VR 125) | U68447 | 4 | 1–536 | 958–1087 |
| *C. psittaci* M56 | U68452 | 5 | 1–536 | 958–1087 |

TABLE IV-continued

| Strain | Accession No. | SEQ ID No. | Map Position for Region A | Map Position for Region B |
|---|---|---|---|---|
| *C. psittaci* NJ1 | U68419 | 6 | 346–881 | 1303–1432 |
| *C. psittaci* CT1 | U68449 | 7 | 1–536 | 958–1087 |
| *C. paittaci* GD | U68450 | 8 | 1–536 | 958–1087 |
| *C. psittaci* Parl | U68455 | 9 | 1–536 | 958–1087 |
| *C. psittaci* WC | U68456 | 10 | 1–536 | 958–1087 |
| *C. psittaci* EBA | U76710 | 11 | 1–534 | 956–1085 |
| *C. psittaci* A22 | U68444 | 12 | 1–534 | 956–1085 |
| *C. psittaci* B577 (VR 656) | U68445 | 13 | 1–534 | 956–1085 |
| *C. psittaci* OSP | U68446 | 14 | 1–534 | 956–1085 |
| *C. paittaci* FP (VR 120) | U68457 | 15 | 1–536 | 958–1088 |
| *C. psittaci* FP Cello | U68458 | 16 | 1–536 | 958–1088 |
| *C. psittaci* FP Vaccine | U68459 | 17 | 1–536 | 958–1088 |
| *C. psittaci* GPIC (VR 183) | U68451 | 18 | 1–536 | 958–1087 |
| *C. pecorum* 1710S | U68431 | 19 | 1–539 | 961–1088 |
| *C. pecorum* BP-1 | U68432 | 20 | 1–539 | 961–1088 |
| *C. pecorum* | U68433 | 21 | 1–539 | 961–1088 |

TABLE IV-continued

| Strain | Accession No. | SEQ ID No. | Map Position for Region A | Map Position for Region B |
|---|---|---|---|---|
| E58 (VR 628) | | | | |
| *C. pecorum* IPA | U68434 | 22 | 1–539 | 961–1088 |
| *C. pecorum* L71 | U68435 | 23 | 1–539 | 961–1088 |
| *C. pecorum* Z | U68439 | 24 | 1–539 | 961–1088 |
| *C. pneumoniae* CM-1 | U68421 | 25 | 1–535 | 957–1084 |
| *C. pneumoniae* CWL-029 | U68422 | 26 | 1–537 | 959–1086 |
| *C. pneumoniae* CWL-1011 | U68423 | 27 | 1–537 | 959–1086 |
| *C. pneumoniae* FML-12 | U68424 | 28 | 1–537 | 959–1086 |
| *C. pneumoniae* FML-16 | U68425 | 29 | 1–537 | 959–1086 |
| *C. pneumoniae* N-16 | U68426 | 30 | 1–537 | 959–1086 |
| *C. pneumoniae* TW-183 | U76711 | 31 | 1–537 | 959–1086 |
| *C. trachomatis* A/Har-13 | U68438 | 32 | 1–555 | 980–1107 |
| *C. trachomatis* B/Tw-5/OT | U68440 | 33 | 1–555 | 980–1107 |
| *C. trachomatis* D/UW-3/CX | U68441 | 34 | 1–555 | 980–1107 |
| *C. trachomatis* F/IC/CAL3 | U68442 | 35 | 1–555 | 980–1107 |
| *C. trachomatis* L2/434/BU | U68443 | 36 | 1–555 | 980–1107 |
| *C. trachomatis* R22 | U68420 | 37 | 346–895 | 1320–1447 |

TABLE IV-continued

| Strain | Accession No. | SEQ ID No. | Map Position for Region A | Map Position for Region B |
|---|---|---|---|---|
| *C. trachomatis* R24 | U68428 | 39 | 1–550 | 975–1102 |
| *C. trachomatis* R27 | U68429 | 39 | 1–550 | 975–1101 |
| *C. trachomatis* H5 | U68427 | 40 | 1–550 | 975–1102 |
| *C. trachotnatis* S45 | U68430 | 41 | 1–553 | 978–1105 |
| *C. trachomatis* MoPn (VR 123) | U68436 | 42 | 1–553 | 976–1106 |
| *C. trachomatis* SFPD Fox | U68437 | 43 | 1–553 | 976–1106 |

TABLE V

| Specificity | Test | Source Region for Primers | | Source Region for |
|---|---|---|---|---|
| | | Forward | Reverse | Probes |
| All Chlamydiales, including Chlamydiaceae, Simkaniaceae, Parachlamydiaceae, etc. | 1 | A | B | |
| All Chlamydiaceae spp. | 2 | A | A | |
| All Chlamydiaceae spp. | 2B | | | A |
| All Chlamydiaceae spp. | 3 | B | B | B |
| Genus or species | 4 | A | A | |

We claim:

1. An isolated oligonucleotide useful as a primer wherein the oligonucleotide consists of a sequence selected from the group consisting of SEQ ID NO: 55, SEQ ID NO: 61 and SEQ ID NO: 67, the complement of SEQ ID NO: 55, SEQ ID NO: 61 and SEQ ID NO: 67, and the RNA equivalent of SEQ ID NO: 55, SEQ ID NO: 61 and SEQ ID NO: 67.

2. An isolated oligonucleotide from 15–100 nucleotides in length comprising a sequence selected from the group consisting of SEQ ID NOs. 56 and 59–60, 62–66, and 68–73, the complement of each of said sequences, and the RNA equivalent of each of said sequences.

3. An isolated oligonucleotide of claim 2, wherein said oligonucleotide is a primer having SEQ ID No. 56.

4. An isolated oligonucleotide of claim 2, wherein said oligonucleotide is a primer having SEQ ID No. 59.

5. An isolated oligonucleotide of claim 2, wherein said oligonucleotide is a primer selected from the group consisting of SEQ ID Nos. 60 and 62.

6. An isolated oligonucleotide of claim 2, wherein said oligonucleotide is a primer selected from the group consisting of SEQ ID Nos. 63–66.

7. An isolated oligonucleotide of claim 2, wherein said oligonucleotide is a primer selected from the group consisting of SEQ ID Nos. 68–70.

8. An isolated oligonucleotide of claim 2, wherein said oligonucleotide is a primer selected from the group consisting of SEQ ID Nos. 71–72.

9. An isolated oligonucleotide of claim 2, wherein said oligonucleotide is a probe having SEQ ID No. 73.

10. A method for distinguishing in a sample a first species or strain of Chlamydiaceae set forth in Table IV from all other species or strains of Chlamydiaceae set forth in Table IV, said method comprising:

a. amplifying nucleic acid contained in said sample with at least one species-specific or strain-specific primer having a length of about 15–30 nucleotides that hybridizes under high stringency conditions to a nucleic acid segment selected from the group consisting of Region A of chlamydial rDNA as defined in Table IV, Region B of chlamydial rDNA as defined in Table IV, the complement of said Region A, the complement of said Region B, the RNA equivalent of said Region A, and the RNA equivalent of said Region B, and thereby producing an amplified nucleic acid segment wherein said segment is specific to said first species or strain; and b. detecting the presence of said amplified segment as indicative of said first species or strain of Chlamydiaceae distinguished from all other species or strains of Chlamydiaceae.

11. A method for distinguishing in a sample a first species or strain of Chlamydiaceae set forth in Table IV from all other species or strains of Chlamydiaceae set forth in Table IV, said method comprising:

a. contacting said sample with a labeled, single-stranded species-specific or strain-specific probe having a length of at least about 15 nucleotides and up to about 100 nucleotides that will hybridize with a nucleic acid segment selected from the group consisting of Region A of chlamydial rDNA as defined in Table IV, Region B of chlamydial rDNA as defined in Table IV, the complement of said Region A, the complement of said Region B, the RNA equivalent of said Region A, and the RNA equivalent of said Region B, and thereby producing a species-specific or strain-specific hybridization product; and b. detecting said hybridization product as indicative of said first species or strain of Chlamydiaceae distinguished from all other species or strains of Chlamydiaceae.

12. The method of claim 10 wherein said primer is selected from the group consisting of SEQ ID NOs. 60–70.

* * * * *